US012760275B2

(12) United States Patent
Machlenkin et al.

(10) Patent No.: US 12,760,275 B2
(45) Date of Patent: Oct. 13, 2026

(54) GENETICALLY ENGINEERED PLACENTAL MUCOSALASSOCIATED INVARIANT T (MAIT) CELLS AND USES THEREOF

(71) Applicant: PLURI BIOTECH LTD., Haifa (IL)

(72) Inventors: Arthur Machlenkin, Gedera (IL); Adi Sharbi-Yunger, Shoham (IL); Eliran Ish Shalom, Tel Yosef (IL); Helena Lea Shaked, Raanana (IL)

(73) Assignee: PLURI BIOTECH LTD., Haifa (IL)

( * ) Notice: Subject to any disclaimer, the term of this patent is extended or adjusted under 35 U.S.C. 154(b) by 0 days.

(21) Appl. No.: 18/842,400

(22) PCT Filed: Jul. 9, 2024

(86) PCT No.: PCT/IL2024/050675

§ 371 (c)(1),
(2) Date: Aug. 29, 2024

(87) PCT Pub. No.: WO2025/012904

PCT Pub. Date: Jan. 16, 2025

(65) Prior Publication Data

US 2025/0290039 A1 Sep. 18, 2025

Related U.S. Application Data

(60) Provisional application No. 63/525,836, filed on Jul. 10, 2023.

(51) Int. Cl.

| | |
|---|---|
| ***C12N 5/0783*** | (2010.01) |
| ***A61K 40/11*** | (2025.01) |
| ***A61K 40/31*** | (2025.01) |
| ***A61K 40/32*** | (2025.01) |
| ***A61K 40/42*** | (2025.01) |
| ***A61P 35/00*** | (2006.01) |
| ***C07K 16/30*** | (2006.01) |

(52) U.S. Cl.

CPC ............ *C12N 5/0636* (2013.01); *A61K 40/11* (2025.01); *A61K 40/31* (2025.01); *A61K 40/32* (2025.01); *A61K 40/4255* (2025.01); *A61K 40/4267* (2025.01); *A61K 40/4269* (2025.01); *A61P 35/00* (2018.01); *C07K 16/30* (2013.01); *C12N 2510/00* (2013.01)

(58) Field of Classification Search

CPC ............................ A61K 40/31; A61K 40/4255
See application file for complete search history.

(56) References Cited

FOREIGN PATENT DOCUMENTS

| | | | | |
|---|---|---|---|---|
| WO | WO-2018023025 A1 * | 2/2018 | ....... | G01N 33/57407 |
| WO | WO-2020113234 A1 * | 6/2020 | ............. | A61K 40/11 |
| WO | WO-2022223975 A1 * | 10/2022 | ......... | C07K 14/7051 |
| WO | WO-2023228182 A1 * | 11/2023 | ........... | C12N 5/0637 |

OTHER PUBLICATIONS

Solders ('Isolation of Immune Cells from Placental Tissues and Phenotypic and Functional Analysis of MAIT Cells', In: MAIT Cells, Methods and Protocols, Kaipe and Magalhaes, Ed.s, 2020, vol. 2098, pp. 55-70) (Year: 2020).*
The abstract of Solders et al (European Journal of Immunology, 2016, vol. 46, suppl. 1, p. 50, abstract No. 4101) (Year: 2016).*
The abstract of Lee et al (Blood, 2013, vol. 122, abstract No. 68) (Year: 2013).*
Klampatsa and Albelda (Journal of Cellular Immunology, 2020, vol. 2, pp. 192-200) (Year: 2020).*
Dusseaux et al (Blood, 2011, vol. 117, pp. 1250-1259). (Year: 2011).*

* cited by examiner

*Primary Examiner* — Karen A. Canella
(74) *Attorney, Agent, or Firm* — Maxwell Minch; Maxwell L Minch Esq. PA

(57) ABSTRACT

This invention is directed in one main aspect to a cell composition comprising a population of engineered mucosal-associated invariant T (MAIT) cells derived from placental tissue expressing an exogenous chimeric antigen receptor (CAR). The invention further discloses a unique placental MAIT cell population, cell compositions comprising the MAIT cell population, and methods of use.

24 Claims, 52 Drawing Sheets

Day 0
FIG. 2A
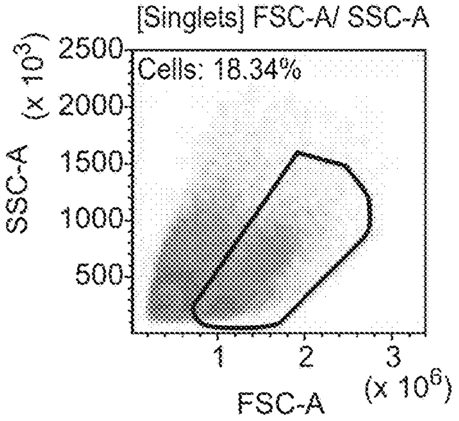
FIG. 2B
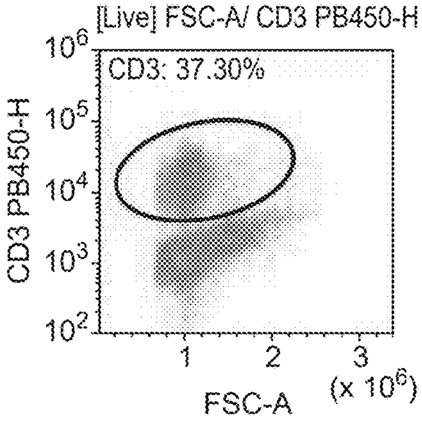
FIG. 2C
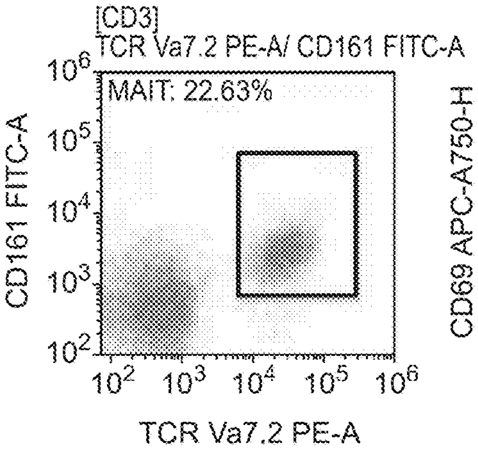
FIG. 2D
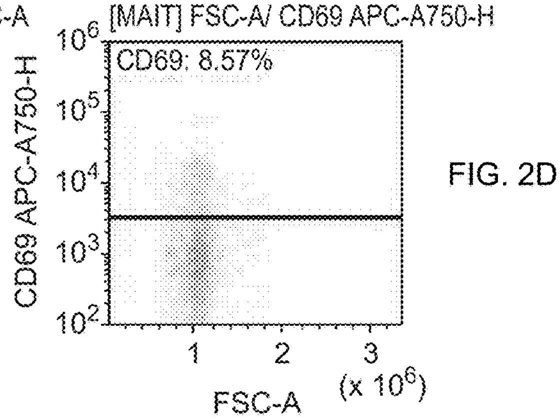
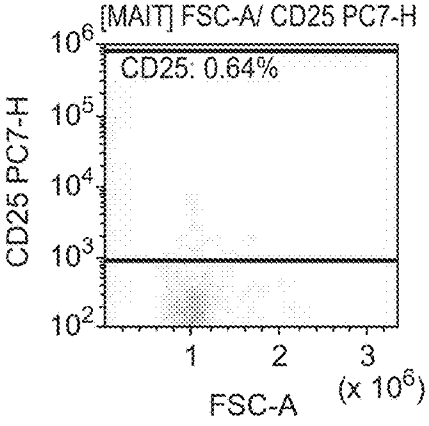
FIG. 2E Day 5

Day 7

Day 10

Day 10 Post Harvest

Day 12

Day 14

Day 17
FIG. 2AJ
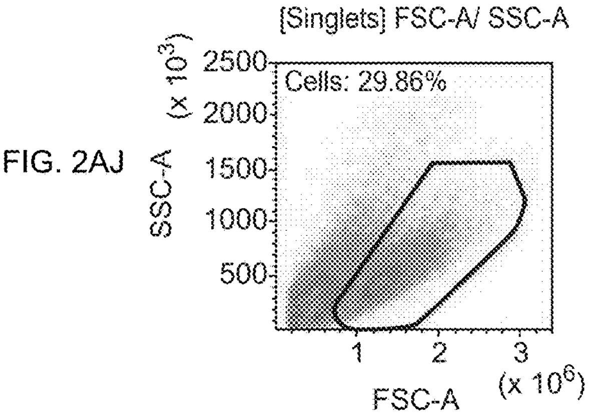
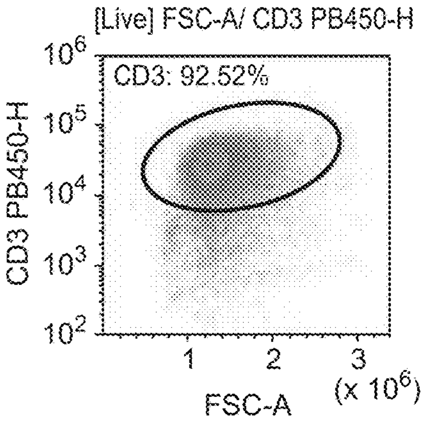
FIG. 2AK
FIG. 2AL
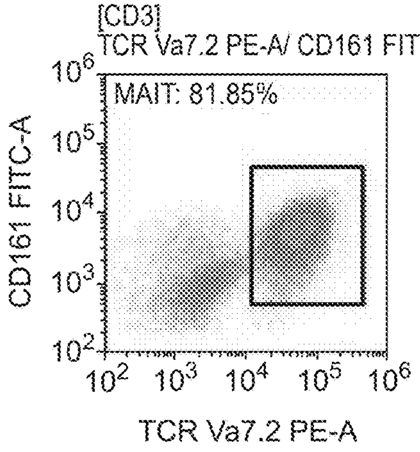
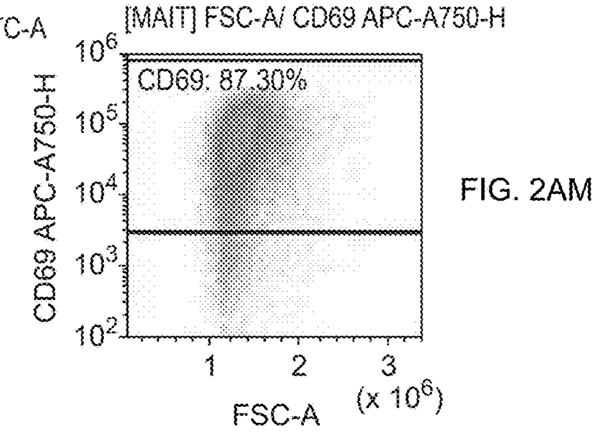
FIG. 2AM
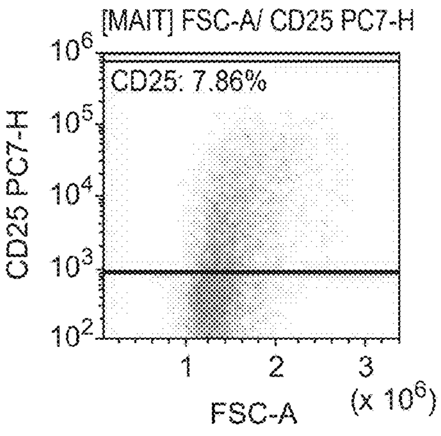
FIG. 2AN

IVB MAIT

PB MAIT

IVB MAIT

PB MAIT
FIG. 6G
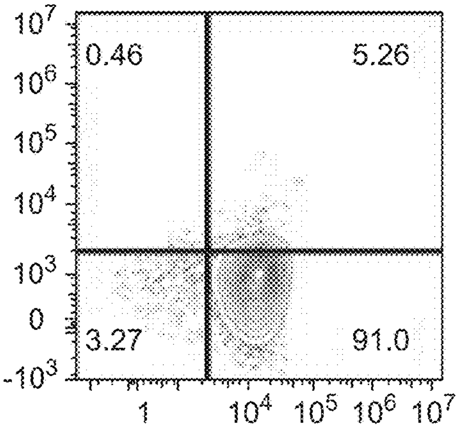
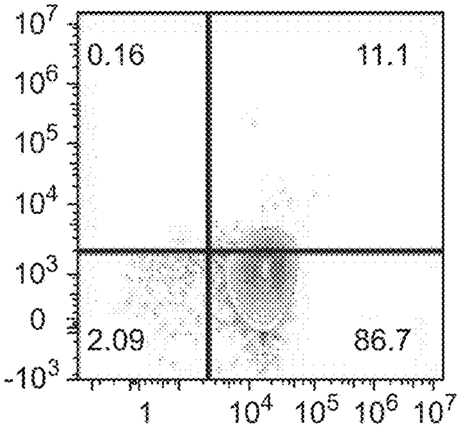
FIG. 6H
FIG. 6H
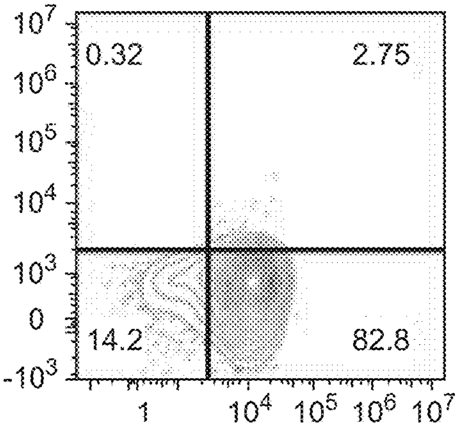
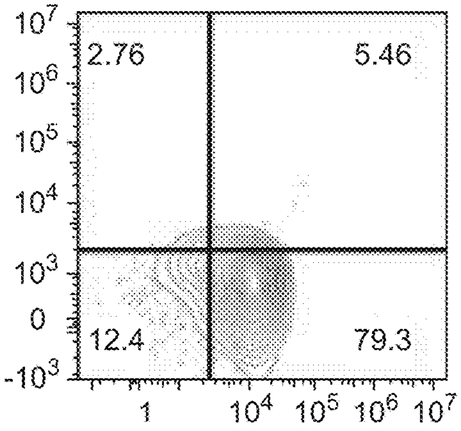
FIG. 6I
FIG. 6I
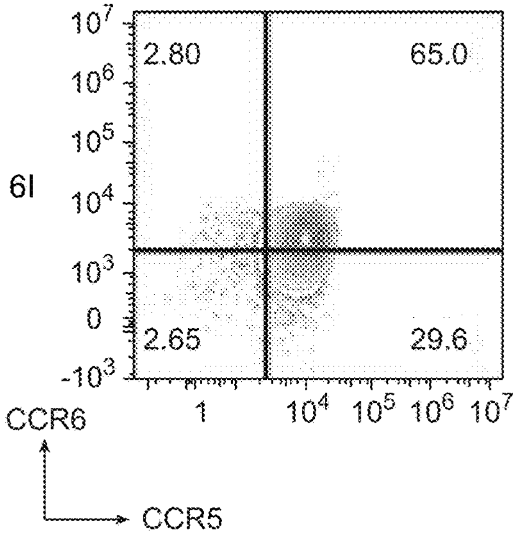
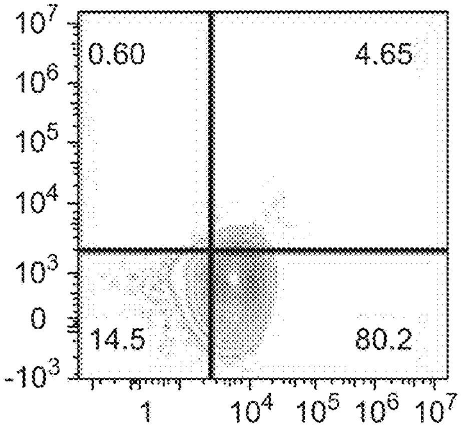
FIG. 6J

PB MAIT

FIG. 6X
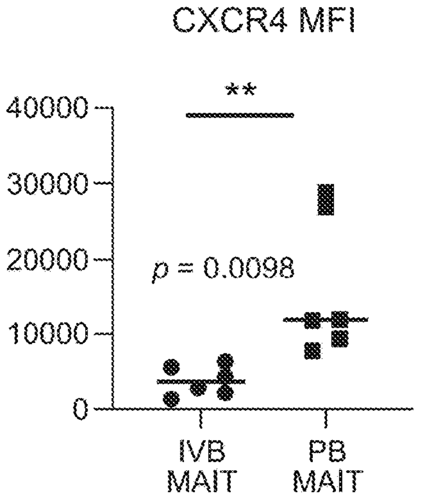
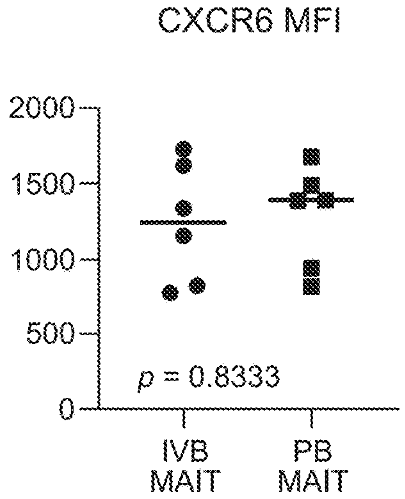
FIG. 6Y
FIG. 6Z
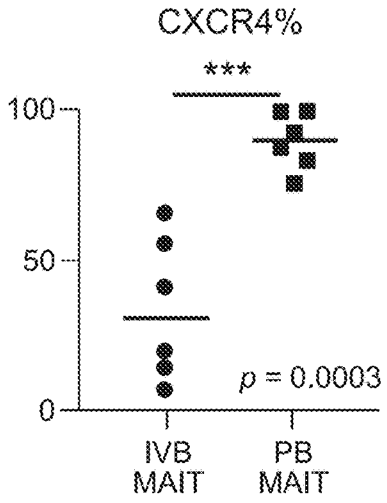
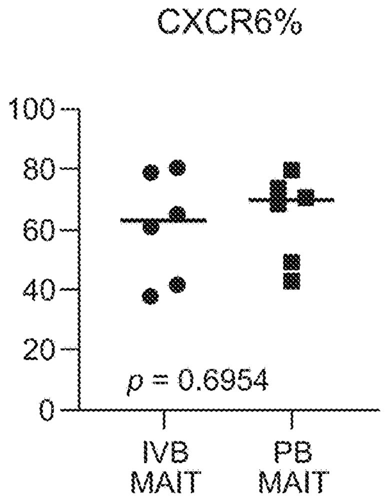
FIG. 6AA

| | Time 0 | | | Day 6/7 | | |
|---|---|---|---|---|---|---|
| | Cell No. ($x10^6$) | %CD3 | %MAIT | Cell No. ($x10^6$) | %CD3 | %MAIT |
| PDM120623-IVB | 2 | 81.9 | 4.61 | 56 | 95.3 | 52.1 |
| PDM120623-CB | 4 | 75.7 | 0.15 | 5.1 | 72.6 | 0.28 |
| PDM140623-IVB | 2 | 91.5 | 13.5 | 7.5 | 96.5 | 67.3 |
| PDM140623-CB | 2 | 83.4 | 0.17 | 3 | 81.3 | 1.16 |
| PDM190623-IVB | 13 | 77.8 | 1.28 | 3.6 | 93.2 | 13.2 |
| PDM190623-CB | 2 | 79.5 | 0.064 | 1.5 | 83.8 | 0.34 |

FIG. 8C

GENETICALLY ENGINEERED PLACENTAL MUCOSALASSOCIATED INVARIANT T (MAIT) CELLS AND USES THEREOF

CROSS-REFERENCE TO RELATED APPLICATIONS

This application is a 35 USC 371 national stage filing of, and claims priority to, PCT/IL2024/050675, having a filing date of Jul. 9, 2024, which is currently pending and claims priority to U.S. Provisional Application No. 63/525,836, having a filing date of Jul. 10, 2023, the disclosure of the foregoing is hereby incorporated by reference in its entirety and all commonly owned.

FIELD OF THE INVENTION

The present disclosure relates in general to the field of genetic engineering of immune cells. More specifically, the present disclosure provides genetically engineered mucosal-associated invariant T (MAIT) cells from Placenta having chimeric antigen receptor (CAR) and uses thereof.

BACKGROUND

Mucosal-associated invariant T (MAIT) cells were first identified in humans, mice, and cattle as a population of αβ T cells enriched in the double-negative ($CD4^-CD8^-$) subset expressing an invariant Vα7.2-Jα33 T cell receptor (TCR) in humans. The term MAIT was established due to the relative enrichment of these T cells within mucosal tissues. The restricting element of MAIT cells is the MHC-1b molecule MR1 (MHC-related 1), which presents intermediates of the vitamin B (both riboflavin (vitamin B2) and folic acid (vitamin B9)) synthesis pathway to MAIT cells. Potent stimulatory ligands in the riboflavin synthesis pathway include 5-(2-oxopropylideneamino)-6-D-ribitylaminouracil (5-OP-RU) and 5-(2-oxoethylideneamino)-6-D-ribitylaminouracil (5-OERU) that are produced by a wide variety of bacteria, mycobacteria and yeasts during riboflavin (vitamin B2) synthesis. This pathway is absent from mammals; therefore, its immune detection allows effective host-pathogen discrimination.

In more detail, T cells that express αβ and γδ T cell receptors (TCRs) develop in the thymus from common T cell progenitors and can mature into one of several functionally distinct T cell lineages. The best-studied of these are conventional T cells, which express an αβ TCR that recognizes peptide antigens presented by MHC molecules. However, there are several 'unconventional' T cell lineages that also develop in the thymus. Unconventional T cells include CD1-restricted T cells, MHC-related 1 (MR1)-restricted T cells and γδ T cells, which recognize non-peptide antigens such as lipids, vitamin B metabolites and phosphor-antigens, respectively. These lineages typically express TCRs that are of limited diversity compared to the TCRs of conventional T cells, and they are often described as cells that bridge the gap between innate and adaptive immunity. Most unconventional T cells co-express surface antigens associated with natural killer (NK) cells and mount potent cytokine responses very rapidly after activation. Their distinctive phenotypes are established during their development, and they represent critically important subpopulations of peripheral T cells with unique effector and regulatory roles (Godfrey, D., Uldrich, A., Mccluskey, J. et al. The burgeoning family of unconventional T cells. Nat Immunol 16, 1114-1123 (2015).

Mucosal-associated invariant T (MAIT) cells are innate-like T cells defined by their semi-invariant αβ T cell receptor (TCR) which recognizes small-molecule biosynthetic derivatives of riboflavin synthesis presented on the restriction molecule major histocompatibility complex (MHC)-related protein-1 (MR1). As mentioned above, MAIT cells TCR comprising a semi-invariant TCR-αchain—usually Vα7.2-Jα33/12/20 in humans, —predominantly associated with the β-chains Vβ2/Vβ13 in humans.

MAIT cells contrast with conventional T cells which have highly variable TCRs, capable of targeting a vast array of peptide epitopes produced by viruses, bacteria and malignant cells. Conventional T cells therefore have exquisite specificity for individual peptides, and individual clones may undergo massive expansion, to provide T cell memory. However, at the first encounter with a pathogen the frequency of any individual peptide-specific T cell will be very low. In contrast, the MAIT cell TCR provides an innate capacity to respond to a specific set of ligands without the need for expansion. A key discovery was the identification of these ligands presented on MR1, which include the potent MAIT cell ligands 5-(2-oxopropylideneamino)-6-D-ribitylaminouracil (5-OP-RU) and 5-(2-oxoethylideneamino)-6-D-ribitylaminouracil (5-OE-RU) produced by a wide variety of bacteria, mycobacteria and yeasts during riboflavin (vitamin B2) synthesis (MINI REVIEW article, Front. Immunol., 27 May 2020, Sec. Mucosal Immunity, Volume 11-2020.

It has been found that MAIT cells can recognize cells infected by bacteria and produce IFN-γ in response. It has been demonstrated that MAIT cells can protect mice from bacterial infection. Early phenotypic work established that human MAIT cells are CD8+ or double negative, have a primarily CCR7 effector memory phenotype, and express high levels of CD161. Detailed phenotyping of MAIT cells also demonstrated that they share several characteristics with invariant natural killer T (iNKT) cells, including the expression of Promyelocytic leukemia zinc finger (PLZF), a transcription factor that governs the innate-like functionality of iNKT cells. Expression of PLZF similarly imparts MAIT cells with innate-like functionality, as evidenced by the ability of cytokines to induce Interferon-g (IFN-γ) production in the absence of TCR stimulation.

Subsequent studies found that human MAIT cells do not express a single invariant TCR, but restricted TCRs comprising Vα7.2-Jα33, Vα7.2-Jα12, or Vα7.2-Jα20, which are predominantly associated with the human □ chains V□2/V□13. Thus, current understanding views MAIT cells as T cells that (a) express a semi-invariant Vα7.2-Jα33/12/20 TCR, (b) are activated by microbial vitamin B antigens presented by MR1 to execute both type 1 and type 17 effector functions, and (c) exhibit innate-like characteristics, governed by expression of PLZF, including the ability to be activated by cytokines independent of their TCR.

Several properties of MAIT cells imply fundamental roles in mammalian immunity. First, MAIT cells have an intrinsic effector-memory phenotype, usually $CD45RA^-CD45RO^+$ $CD95^{Hi}CD62L^{Lo}CD44^{Hi}$, with capacity for rapid secretion of several pro-inflammatory cytokines. Second, MAIT cells are remarkably abundant in human tissues, typically comprising 1-4% of all T cells in peripheral blood and up to 10% of airway T cells and 20-40% of liver T cells. Moreover, as each TCR recognizes the same ligand, early in an immune response, MAIT cells will markedly exceed the numbers of conventional antigen-specific T cells responding to cognate antigens.

The conservation and abundance of MAIT cells is likely explained by their broad range of functionality attributable to different modes of activation, each triggering a distinct transcriptomic program. Because of their capability for diverse functional responses in diverse immunological contexts, these intriguing cells now appear to be multifunctional effectors central to the interface of innate and adaptive immunity.

Chimeric antigen receptor (CAR) is a type of genetically engineered receptor that is added to immune cells, typically T cells, in cancer therapy. These receptors allow the T cells to recognize and target specific antigens on cancer cells. CAR T-cell therapy has shown promising results in treating certain types of cancer.

Chimeric antigen receptors (CARs), also known as chimeric immunoreceptors, chimeric T cell receptors or artificial T cell receptors are receptor proteins that have been engineered to give T cells the new ability to target a specific antigen. The receptors are chimeric in that they combine both antigen-binding and T cell activating functions into a single receptor.

CAR T cell therapy is well known in the art and uses T cells engineered with CARs to treat cancer. T cells are modified to recognize cancer cells and destroy them. The standard approach is to harvest T cells from patients, genetically alter them, then infuse the resulting CAR T cells into patients to attack their tumors (Fox M (Jul. 12, 2017. "New Gene Therapy for Cancer Offers Hope to Those With No Options Left" *NBC News*.

CAR T cells can be derived either autologously from T cells in a patient's own blood or allogeneically from those of a donor. Once isolated, the T cells are genetically engineered to express a specific CAR that programs the T cells to target an antigen present on the tumor cell surface. The CAR helps the T cells recognize a specific cancer cell antigen and activate the T cells to kill these cancer cells.

There are substantial differences between CAR-T cell therapy and TCR-T cell therapy as described in: "CAR T-Cell Therapy vs. TCR-T Therapy: The Differences and Applications-Atlantis Bioscience Pte Ltd.".

Structurally, CAR T-cells and TCR-engineered T-cells are different. CAR-T cells are composed of engineered intracellular and extracellular domains. The extracellular domain is composed of a single-chain variable fragment (consisting of antigen binding domain of the antibody) to recognize specific antigens on the surface of cells to trigger intracellular signaling leading to T-cell activation. The maintenance of T-cell activation and survival of CAR T-cells are further enhanced by the addition of costimulatory domains to the intracellular portion of the CAR T-cell.

Use of CAR T Cells was previously described in the art. For example, U.S. application Ser. No. 17/309,451 disclose a population of T cells expressing a chimeric antigen receptor (CAR), wherein the T cells are placental T cells derived from cord blood, placental perfusate T cells, or a mixture of both. This application further discloses a method of treating cancer or a symptom in a patient in need thereof by administering to the patient an amount of the population of the T cells described above.

In addition, attempts have been made in the art to use MAIT cells for allogeneic adoptive immunotherapy. U.S. patent application Ser. No. 17/414,689 disclose mucosa associated invariant T (MATT) cell expressing a chimeric antigen receptor (CAR) for treatment of a cancer, an immune disease or an infectious disease in a subject, wherein the MAIT cell is allogenic with respect to the subject. In this disclosure the MAIT cells are acquired from blood samples (including peripheral blood and cord blood.

The present invention take the usage of CAR and the usage of MAIT cells and raise it one step forward by providing unique placental CAR-MAIT cells that have an improved effector activity and a higher survivability in the hosting body compared to peripheral blood and cord blood MAIT cells, and compared to conventional T cells as disclosed in the prior art. Engineering these placental MAIT cells to express CAR allows for various therapeutic uses.

SUMMARY OF THE INVENTION

In one main aspect, the present invention is directed to a cell composition comprising a population of engineered mucosal-associated invariant T (MAIT) cells expressing an exogenous chimeric antigen receptor (CAR), wherein said MAIT cells are derived from placental tissue, optionally, the composition further comprising a pharmaceutically acceptable carrier. In some optional embodiments, the population of the placental MAIT cells is obtained from intervillous blood (IVB).

In accordance with embodiments of the invention, the cell composition provided herein is adapted for cell therapy. Preferably but not necessarily, at least 90% of the placental MAIT cells are characterized by the expression of TCRV$\alpha$7.2+ and a high level of CD161 (CD161$^{high}$). In some embodiments, the cell composition of the invention comprises $10^9$ to $10^{11}$ viable cells of the engineered placental CAR-MAIT cell population.

In accordance with the present invention, the exogenous CAR expressed by the placental MAIT cells of the cell composition recognizes a tumor antigen. In one embodiment, the tumor antigen is Mesothelin (MSLN). Yet, in other optional embodiments the tumor antigen is selected from the group consisting of CD19, B7-H6, CD20, CD22, CD33, CD38, CD70, CD123, BCMA, CLL1, CD7, CS1, CEA, AFP, PSMA, GPC3, GD2, EGFRVIII, CXCR5, NKG2D, HER2, Mesothelin, Claudin 3, Claudin 4, Claudin 6, Claudin 18.2, ROR1, ROR3, Muc1, or Muc16. In some optional embodiments, the exogenous CAR expressed by the placental MAIT cells of the cell composition provided herein recognizes a microbial antigen and/or a viral antigen. Yet, in some other optional embodiments, the exogenous CAR expressed by the placental MAIT cells of the cell composition provided herein recognizes a target molecule expressed on regulatory T cells. In a specific non-limiting embodiment, the target molecule is CCR8. Yet, in further embodiments of the invention, the exogenous CAR expressed by the placental MAIT cells of the cell composition specifically recognizes a target molecule expressed on alloreactive lymphocytes. In a specific non-limiting embodiment, the target molecule is CD70. In further options, the exogenous CAR expressed by the placental MAIT cells of the cell composition described herein recognizes a target molecule expressed on senescent cells. In a specific non-limiting example, the target molecule is urokinase plasminogen activator (uPAR). In further optional embodiments of the invention, the exogenous CAR expressed by the placental MAIT cells of the cell composition recognizes a target molecule expressed on cells associated with a fibrotic disease or condition. A specific none-limiting example of such target molecule is fibroblast activation protein (FAP). Optionally, the exogenous CAR expressed by the placental MAIT cells of the cell composition recognizes a target molecule expressed on cells associated with an autoimmune disease or disorder. In a specific non-limiting example, the target molecule is expressed on B cells, such as but not limited to CD19, CD20, CD21. In some other optional embodiments of the invention, the target molecule comprises a pathogenic MHC class II: peptide complex associated with the autoimmune disease, an autoantibody, a B cell antibody targeted by B cell antibody receptors (BAR), carboxypeptidase H, chromogranin A, glutamate decarboxylase, imogen-38, insulin, insulinoma antigen-2 and 2β, islet-specific glucose-6-phosphatase catalytic subunit related protein (IGRP), proinsulin, citrullinated protein, collagen II, heat shock proteins, human cartilage glycoprotein, double-stranded DNA, La antigen, nucleosomal histones and ribonucleoproteins (snRNP), phospholipid-β-2 glycoprotein I complex poly (ADP-ribose) polymerase, Sm antigens of U-1 small ribonucleoprotein complex, a enolase, aquaporin-4, β-arrestin, myelin basic protein, myelin oligodendrocytic glycoprotein, proteolipid protein S100-β, R1-type reticulin, gastric H+/K+-ATPase, 21-hydroxylase, 17-hydroxylase, cytochrome P450 side-chain cleavage enzyme, CD19, and said engineered MAIT cells bind said pathogenic MHC class II: peptide complex associated with said autoimmune disease, an autoantibody, a B cell antibody targeted by B cell antibody receptors (BAR), carboxypeptidase H, chromogranin A, glutamate decarboxylase, imogen-38, insulin, insulinoma antigen-2, 2β, islet-specific glucose-6-phosphatase catalytic subunit related protein (IGRP), proinsulin, citrullinated protein, collagen II, heat shock proteins, human cartilage glycoprotein, double-stranded DNA, La antigen, nucleosomal histones, ribonucleoproteins (snRNP), phospholipid-β-2 glycoprotein I complex poly (ADP-ribose) polymerase, Sm antigens of U-1 small ribonucleoprotein complex, a enolase, aquaporin-4, β-arrestin, myelin basic protein, myelin oligodendrocytic glycoprotein, proteolipid protein S100-β, R1-type reticulin, gastric H+/K+-ATPase, 21-hydroxylase, 17-hydroxylase, cytochrome P450 side-chain cleavage enzyme, or CD19. Yet, in some optional embodiments of the invention, the autoantibody that the cell composition is used for is DSG3.

In some optional embodiments of the invention, the exogenous chimeric antigen receptor (CAR) expressed by the placental MAIT cells of the cell composition provided herein comprises: an antigen-binding domain configured to specifically recognize a tumor antigen; a transmembrane domain that anchors the CAR in the cell membrane; at least one costimulatory domain that enhances cell signaling and T-cell activation; and an intracellular signaling domain responsible for initiating T-cell activation upon antigen recognition. In further embodiments, the antigen-binding domain of the chimeric antigen receptor (CAR) may comprise either one of: a single-chain antibody, a single-chain variable fragment (scFv), a VHH fragment, wherein each is configured to recognize a designated tumor antigen. Yet, in some optional embodiments, the antigen binding domain of the CAR of the cell composition of the invention may specifically binds to one or more antigens selected from the group consisting of: CD19, B7-H6, CD20, CD22, CD33, CD38, CD70, CD123, BCMA, CLL1, CD7, CS1, CEA, AFP, PSMA, GPC3, GD2, EGFRVIII, CXCR5, NKG2D, HER2, Mesothelin, Claudin 3, Claudin 4, Claudin 6, Claudin 18.2, ROR1, ROR3, Muc1, or Muc16. In some additional optional embodiment, the costimulatory domain of the CAR of the cell composition of the invention comprises one or more functional signaling domain derived from OX40, CD2, CD27, CD28, CDS, ICAM-1, LFA-1 (CD11a/CD18), ICOS (CD278), or 4-1BB (CD137). In some additional optional embodiment, the intracellular signaling domain of the CAR comprises either the intracellular signaling domain of CD3 zeta, FcR gamma, or a functional fragment thereof, each configured to initiate or maintain T-cell activation upon antigen recognition.

Yet, in some further embodiments of the invention, the CAR expressed by the placental MAIT cells of the cell composition provided herein is encoded by a genetic construct selected from the group consisting of: a monocistronic construct, a bicistronic construct, or a tricistronic construct; wherein at least one additional element in the bicistronic or tricistronic construct is selected from the group consisting of cytokines (e.g. IL15, IL18), constitutively active tyrosine kinases (e.g. c-kit or other genetic elements that enhance survival, proliferation, or effector function of the MAIT cells), wherein the cytokines are either unmodified or modified, and/or secreted, conditionally active, constitutively active, or expressed in a membrane-bound form.

In some embodiments, pre-expanded population of the placental MAIT cells of the cell composition provided herein, exhibits a higher percentage of cells expressing low levels of CD45RA and low levels of CD62L compared to a pre-expanded population of MAIT cells derived from peripheral blood, indicative of an effector memory phenotype of the placental MAIT cells. In some additional embodiments, pre-expanded population of the placental MAIT cells of the cell composition demonstrates a higher percentage of cells expressing CCR5 and/or CCR6 chemokine receptors and a lower percentage of cells expressing CXCR4, compared to a pre-expanded population of MAIT cells derived from peripheral blood. In further embodiments, the population of placental MAIT cells of the cell composition of the invention exhibits a higher percentage of cells expressing Granzyme B compared to a population of MAIT cells derived from peripheral blood, indicative of an enhanced effector and lytic functions of the placental MAIT cells. Yet, in additional embodiments, pre-expanded population of said placental MAIT cells of the cell composition of the invention, exhibits a higher percentage of cells expressing Perforin compared to a pre-expanded population of MAIT cells derived from peripheral blood, indicative of an enhanced effector and lytic functions of the placental MAIT cells. In additional embodiment, pre-expanded population of the placental MAIT cells of the cell composition exhibits a higher percentage of cells expressing Perforin and/or Granzyme B compared to a pre-expanded population of conventional T cells derived from peripheral blood, indicative of enhanced effector and lytic functions of the placental MAIT cells. Yet, in further embodiments, pre-expanded population of the placental MAIT cells of the cell composition disclosed exhibits a higher percentage of cells expressing Perforin and/or Granzyme B compared to a pre-expanded population of conventional T cells derived from cord blood, indicative of enhanced effector and lytic functions of the placental MAIT cells. In additional embodiments, pre-expanded population of the placental MAIT cells of the cell composition exhibits a higher percentage of cells expressing TNFa compared to a pre-expanded population of conventional T cells derived from cord blood, indicative of enhanced effector functions of the placental MAIT cells. In additional embodiments, pre-expanded population of the placental MAIT cells of the cell composition exhibits a higher percentage of cells expressing TNFa compared to a pre-expanded population of conventional T cells derived from peripheral blood conventional T cells, indicative of enhanced effector functions of the placental MAIT cells. Yet, in additional embodiments the population of placental MAIT cells of the cell composition exhibits a higher percentage of cells expressing one or more of: Perforin, Granzyme B, Granzyme B and Perforin, TNFa, and TNFa and INFg compared to a population of placental T cells indicative of enhanced effector and lytic function. In accordance with further embodiments of the invention, pre-expanded population of the placental MAIT cells of the cell composition exhibits a higher percentage of cells expressing CD8αα+ compared to a pre-expanded population of cord blood MAIT cells indicative of a mature phenotype of the placental MAIT cells.

In some aspects of the invention, the cell composition disclosed herein is for use in therapy. In some optional embodiments, the cell composition may be used for treating a subject having a tumor or malignancy. Exemplifying use of the cell composition of the invention is for a subject afflicted with a tumor such as, but not limited to: blood cancer, melanoma, breast cancer, colon cancer, kidney cancer, liver cancer, lung cancer, ovary cancer, pancreatic cancer, prostate cancer, uterine cancer, cervical cancer, bladder cancer, stomach cancer, head and neck cancer, brain cancer, skin cancer and sarcoma.

In some aspects of the invention a method of treating a subject having a tumor or malignancy is provided, wherein the method comprises administering to the subject a cell composition according to any optional embodiment as defined above. The tumor treated may be for example, blood cancer, melanoma, breast cancer, colon cancer, kidney cancer, liver cancer, lung cancer, ovary cancer, pancreatic cancer, prostate cancer, uterine cancer, cervical cancer, bladder cancer, stomach cancer, head and neck cancer, brain cancer, skin cancer and sarcoma. Preferably, but not necessarily, the cell composition for treating the subject is adapted for cell therapy and the population comprises at least $10^9$ viable cells, of which at least 90% are TCR Vα7.2$^+$ CD161$^{high}$.

In some embodiments, the engineered placental MAIT cells used for treating the subject are allogeneic to said subject. In other options, the engineered placental MAIT cells are partly histocompatible with the subject, or the engineered placental MAIT cells are not histocompatible with the subject.

In some aspects of the invention, a method of treating a subject infected with a pathogen is provided. The pathogen may be either one of a bacterial pathogen, viral pathogen, or a fungal pathogen, and the method comprises administering to the subject a cell composition according to any suitable optional embodiment as defined above.

In some additional aspects of the invention, method of treating a subject suffering from a fibrotic disease or condition, method of treating a subject suffering from a senescence-associated disease or condition, method of treating a subject having an allogeneic transplantation, method of treating a subject suffering from an autoimmune disease or disorder, are provided, wherein all methods above comprising administering to the subject in need a cell composition according to any suitable optional embodiment as defined above.

Yet, in accordance with additional aspects of the invention, a method of treating a subject infected with a pathogen is provided, the method comprising administering to the subject a composition comprising a population of MAIT cells derived from placenta. The population of MAIT cells according to this embodiment is not engineered MAIT cells, and the cells do not express exogenous CAR. The pathogen may be for example, a bacterial pathogen, a viral pathogen, or a fungal pathogen. In some specific examples the bacterial pathogen may comprise a *Mycobacterium tuberculosis* bacteria. In some embodiments, the bacterial pathogen comprises an antibiotic resistant bacteria or bacterial treatment resistant bacteria. In some other specific examples, the fungal pathogen may comprise an invasive *Aspergillus*. In some further examples, the viral pathogen may comprise a cytomegalovirus, a hepatitis B virus, or a hepatitis C optionally the infection is as a result of a post-surgical infection. Preferably, but not necessarily, the MAIT cells used for treating the subject according to this aspect of the invention are allogeneic to said subject.

Yet, in accordance with additional aspects of the invention, a population of placental mucosal-associated invariant T (MAIT) cells is provided, wherein the placental MAIT cells are at least 90% TCRVα7.2$^+$ CD161$^+$ and wherein majority of said placental MAIT cells are characterized by lack expression of CD45RA and CCR7 (CD45RA$^-$CCR7$^-$), indicative of an effector memory phenotype of the cells. Optionally, this population of MAIT cells are engineered placental MAIT cells expressing a chimeric antigen receptor (CAR).

In some embodiments, this population of placental MAIT cells are further characterized by high or low expression of CD62L. In some additional embodiments, this population of placental MAIT cells are further characterized by high expression of CD69. Optionally, this population of placental MAIT cells may be obtained from intervillous blood (IVB). Additionally, this population of placental MAIT cells according to any optional embodiment described above may be used for preparing a cell composition to be used for cell therapy.

In some embodiments, the present disclosure provides a population of engineered mucosal-associated invariant T (MAIT) cells comprising an exogenous chimeric antigen receptor (CAR), wherein the MAIT cells are derived from placental intervillous blood (IVB).

In some embodiments, the CAR recognizes a tumor antigen. In some embodiments, the CAR recognizes a target molecule expressed on regulatory T cells. In some embodiments, the CAR recognizes a target molecule expressed on alloreactive lymphocytes. In some embodiments, the CAR recognizes a target molecule expressed on autoimmune cells. In some embodiments, the CAR recognizes a target molecule expressed on senescence cells.

In some embodiments, the CAR of the engineered IVB MAIT cells comprises an antigen binding domain, a transmembrane domain, and a costimulatory domain. The antigen binding domain can be a single chain antibody or a single chain antibody fragment for example but not limited to a single chain variable fragment (scFv). In some embodiments, targets of the antigen binding domain include, but are not limited to: 5T4, ALK, AXL, B7-H6, CD5, CD7, CD19, CD20, CD22, CD30, CD33, CD38, CD44v6, CD70, CD80, CD89, CEA, cMET, CLEC14a, CD123, CD133, CDH17, BCMA, CLL1, CXCR5, CS1, CEA, AFP, PSMA, PSCA, FAP, FHSR, GPC3, GD2, EGFR, EGFRVIII, EpCAM, NKG2D, HER2, IL13Rα2, TEM8, TGF, Mesothelin, Claudin 3, Claudin 4, Claudin 6, Claudin 18.2, ROR1, ROR2, ROR3, or Muc1, Muc16, Muc-CD.

In some embodiments, the costimulatory domain of the CAR comprises a functional signaling domain derived from OX40, CD2, CD27, CD28, CDS, ICAM-1, LFA-1 (CD11a/CD18), ICOS (CD278), or 4-1BB (CD137). In some embodiments, the intracellular signaling domain of the CAR comprises an intracellular signaling domain of CD3 zeta, or FcR gamma, or a functional fragment thereof.

In some embodiments, there is provided a pharmaceutical composition comprising a pharmaceutical acceptable carrier and the population of engineered IVB CAR-MAIT cells disclosed herein.

In some embodiments, there is provided a method of treating a subject having a tumor or malignancy, comprising administering to the subject a composition comprising the population of engineered IVB CAR-MAIT cells disclosed herein. In some embodiments, the engineered IVB CAR-MAIT cells are allogeneic to the subject.

In some other embodiments, the engineered IVB CAR-MAIT cells bind Mesothelin (MSLN) and said engineered IVB CAR-MAIT cells bind MSLN.

In some embodiments, there is provided a method of treating a subject suffering from a fibrotic disease or condition, comprising administering to the subject a composition comprising the population of engineered IVB CAR-MAIT cells disclosed herein. In some embodiments, the fibrotic disease or condition comprises cardiac fibrosis. In some embodiments, when the subject is suffering from cardiac fibrosis the engineered IVB CAR-MAIT cells bind to fibroblast activation protein (FAP). In some embodiments, the engineered IVB CAR-MAIT cells are allogeneic to the subject.

In another embodiment, there is provided a method of treating a subject having an allogeneic transplantation, comprising administering to the subject a composition comprising the population of engineered IVB CAR-MAIT cells disclosed herein, wherein the IVB CAR-MAIT cells bind to a target molecule expressed on alloreactive lymphocytes. Examples of target molecules expressed on alloreactive lymphocytes include, but are not limited to CD70, CD19, CD20.

In some embodiments, there is provided a method of treating a subject suffering from a senescence-associated disease or condition comprising administering to the subject a composition comprising the population of engineered IVB CAR-MAIT cells disclosed herein. In certain embodiments, the engineered MAIT cells are allogeneic to said subject. In some embodiments, the senescence-associated disease or condition comprises chronic inflammation, fibrotic liver disease, atherosclerosis, or diabetes, or a combination thereof. In some embodiments, the IVB CAR-MAIT cells express exogenous antigen receptors that bind to a target molecule. In some embodiments, the engineered IVB CAR-MAIT cells bind urokinase plasminogen activator receptor (uPAR) and said engineered IVB CAR-MAIT cells bind uPAR.

In some embodiments, there is provided a method for treating a subject suffering from an autoimmune disease or disorder, comprising administering to said subject a composition comprising the population of engineered IVB CAR-MAIT cells disclosed herein. In some embodiments, the engineered IVB CAR-MAIT cells are allogeneic to said subject. In some embodiments, the autoimmune disease or disorder comprises systemic lupus erythematosus (SLE), refractory SLE, pemphigus vulgaris, multiple sclerosis, type I diabetes, rheumatoid arthritis, celiac disease, pernicious anemia, inflammatory myopathies, myasthenia gravis, or adrenalitis, or a combination thereof. In some embodiments, the engineered IVB CAR-MAIT cells recognize and bind to a target antigen comprising a pathogenic MHC class II: peptide complex associated with said autoimmune disease, an autoantibody, a B cell antibody targeted by B cell antibody receptors (BAR), carboxypeptidase H, chromogranin A, glutamate decarboxylase, imogen-38, insulin, insulinoma antigen-2 and 2β, islet-specific glucose-6-phosphatase catalytic subunit related protein (IGRP), proinsulin, citrullinated protein, collagen II, heat shock proteins, human cartilage glycoprotein, double-stranded DNA, La antigen, nucleosomal histones, ribonucleoproteins (snRNP), phospholipid-β-2 glycoprotein I complex poly (ADP-ribose) polymerase, Sm antigens of U-1 small ribonucleoprotein complex, a enolase, aquaporin-4, β-arrestin, myelin basic protein, myelin oligodendrocytic glycoprotein, proteolipid protein S100-β, R1-type reticulin, gastric H+/K+-ATPase, 21-hydroxylase, 17-hydroxylase, cytochrome P450 side-chain cleavage enzyme, or CD19. In certain embodiments, an autoantibody is DSG3.

In other embodiments, there is provided a method of treating a subject infected with a pathogen, comprising administering to the subject a composition comprising a population of placental IVB CAR-MAIT cells, wherein the IVB MAIT cells are allogeneic to said subject.

In certain embodiments, these IVB MAIT cells do not comprise an exogenous antigen receptor. In some embodiments, the pathogen is a bacterial pathogen, a viral pathogen, or a fungal pathogen. In certain embodiments, a bacterial pathogen comprises an antibiotic resistant bacteria or bacterial treatment resistant bacteria. In some embodiments, a bacterial pathogen comprises a *Mycobacterium tuberculosis* bacteria. In some embodiments, a fungal pathogen comprises an invasive *Aspergillus*. In some embodiments, a viral pathogen comprises a cytomegalovirus, a hepatitis B virus, or a hepatitis C virus. In some embodiments, the infectious condition treated by a method disclosed herein, is limited to site specific infections, for example wherein an infection is limited to a specific site or organ. In some embodiments, an infection treated by a method disclosed herein comprises a post-surgical infection.

These and other aspects of the engineered placental CAR-MAIT cells and uses thereof will be appreciated from the ensuing descriptions of the figures and detailed description.

DESCRIPTION OF THE DRAWINGS

Some embodiments of the engineered IVB MAIT cells and/or IVB CAR-MAIT cells and methods of use thereof, are herein described, by way of example only, with reference to the accompanying drawings. With specific reference now to the drawings in detail, it is stressed that the particulars shown are by way of example and for purposes of illustrative discussion of embodiments of the engineered IVB CAR-MAIT cells and IVB MAIT cells lacking an exogenous antigen receptor, and therapeutic uses thereof. In this regard, the description taken with the drawings makes apparent to those skilled in the art how embodiments of the engineered IVB CAR-MAIT cells, and IVB MAIT cells lacking an exogenous antigen receptor, and therapeutic uses thereof may be practiced.

Figures FIGS. 1A-1D are schematic illustrations demonstrating collection of maternal blood from Placenta, wherein FIG. 1A illustrates both, fetal side and maternal side of the placenta; FIG. 1B illustrates maternal side after removal of a membrane; FIG. 1C illustrated incisions made in the maternal tissue; and FIG. 1D illustrates manipulations made at the Fetal part in accordance with examples of the present invention.

Figure 1A:
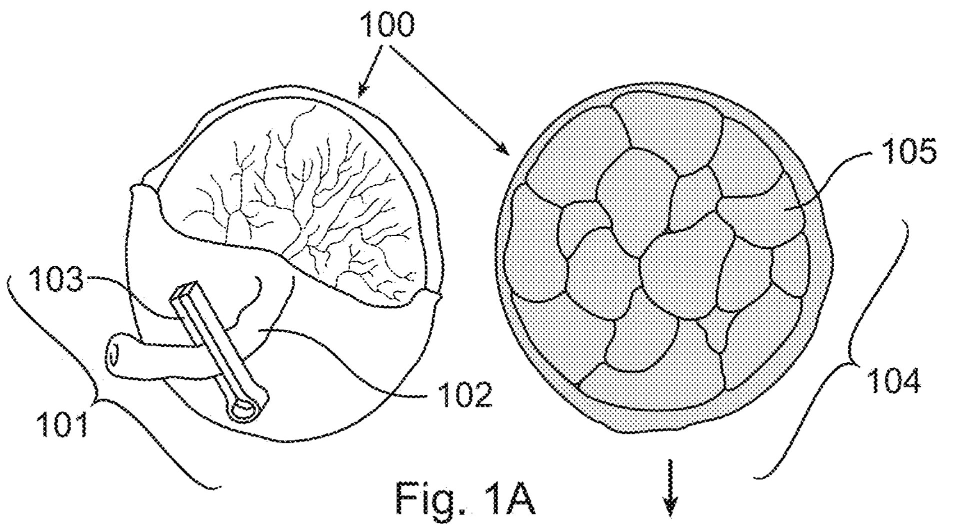
Figure 1B:
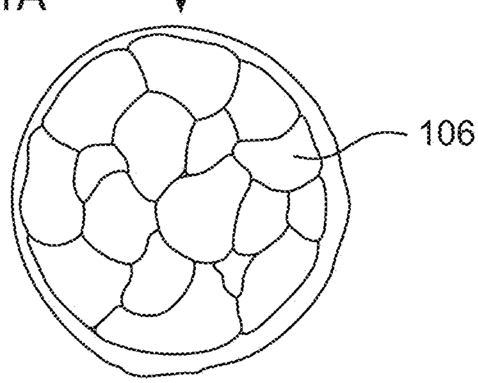
Figure 1C:
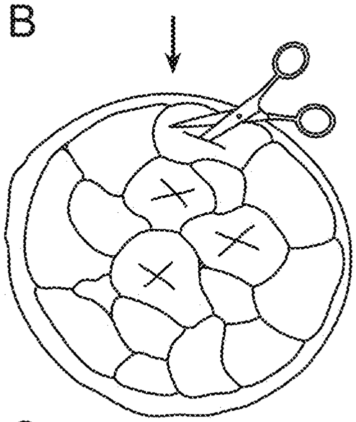
Figure 1D:
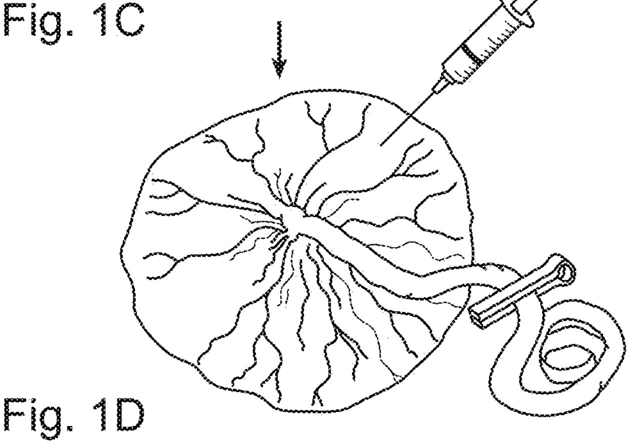

Placenta 100 comprises a placenta fetal side 101 comprises umbilical cord 102 that is clamped using a clip 103 to prevent mixing of fetal blood with mother (IVB) blood, and a placenta maternal side 104 that is covered with amnion membrane 105 (FIG. 1A). IVB collection begins with the removal of the amnion membrane surrounding the maternal side, exposing the cotyledons 106 (FIG. 1B). Superficial cuts are made in the cotyledons using scissors or any other suitable cutting tool (FIG. 1C). The placenta is then flipped so that the fetal side faces up. Phosphate buffer saline (PBS) is injected into the decidua basalis, away from the fetal blood vessels. All the maternal blood that flows out of the placenta is collected. Mononuclear cells are then isolated using Lymphoprep (a density gradient column), and an intermediate cell stock is subsequently frozen.

Figure 2F:
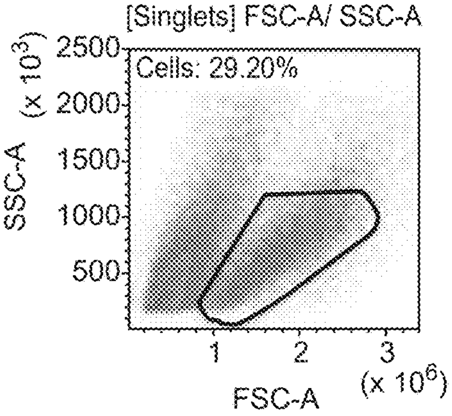
Figure 2G:
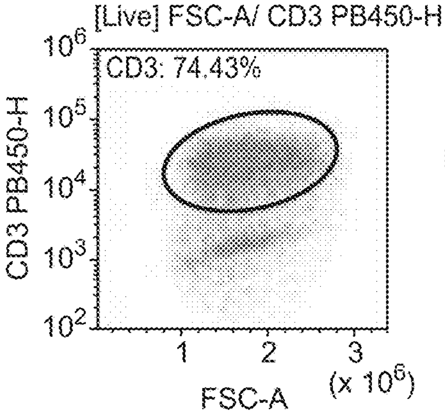
Figure 2H:
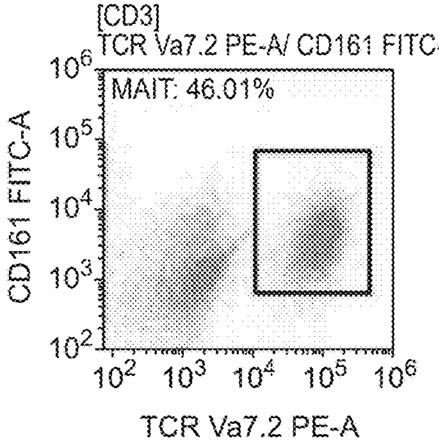
Figure 2I:
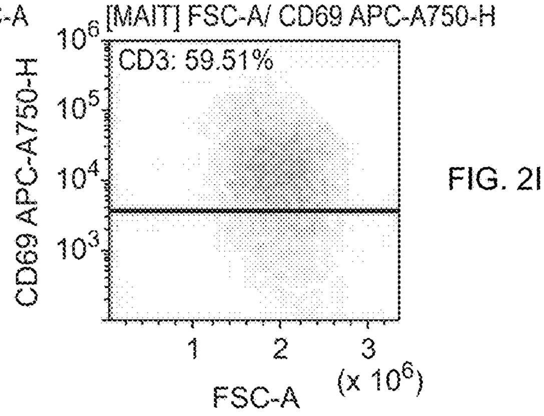
Figure 2J:
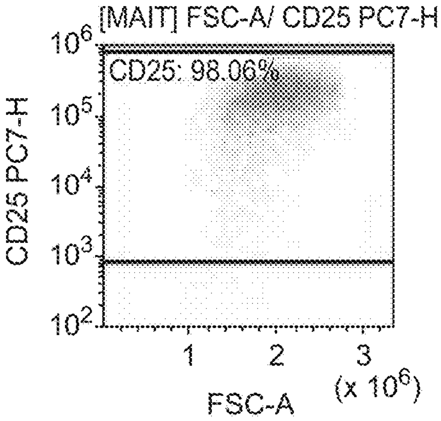
Figure 2K:
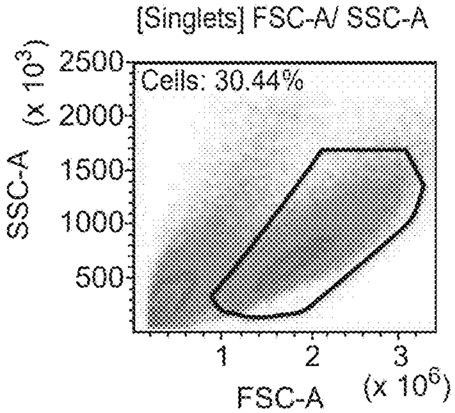
Figure 2L:
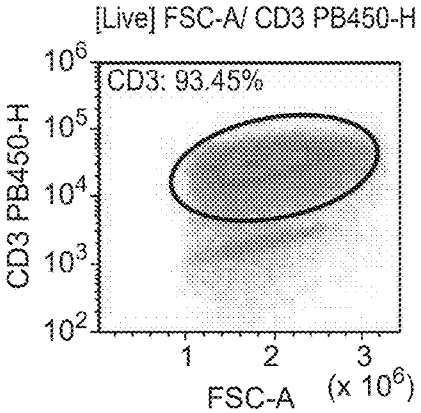
Figure 2M:
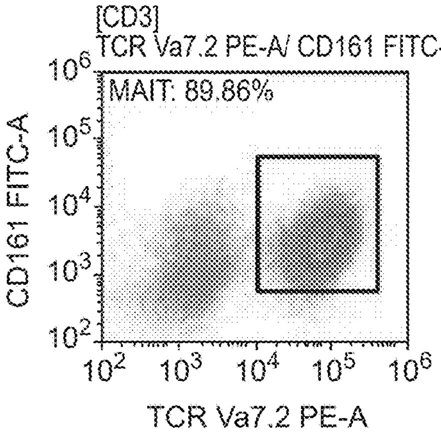
Figure 2N:
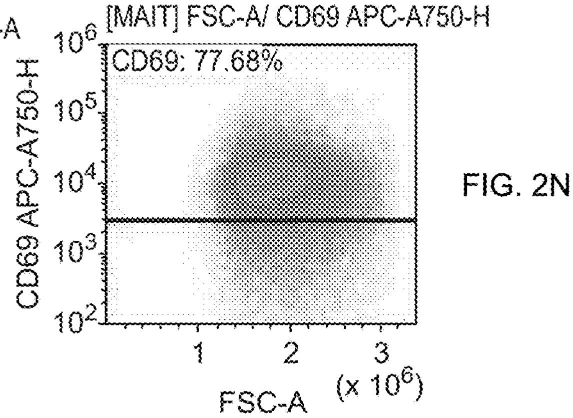
Figure 2O:
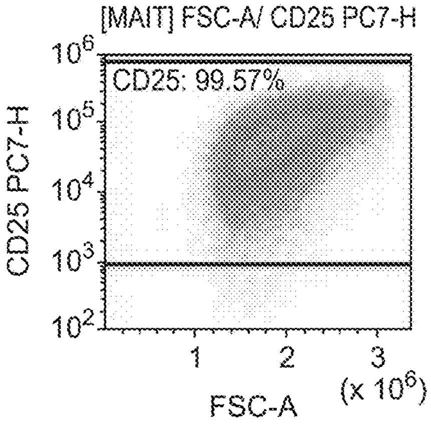
Figure 2P:
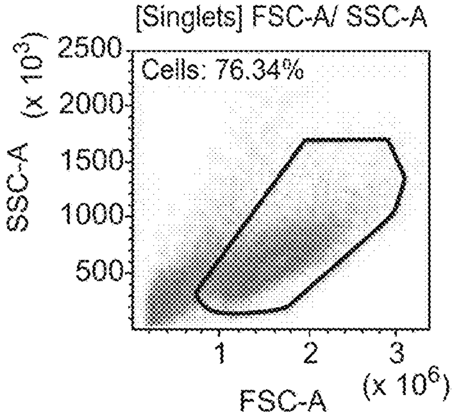
Figure 2Q:
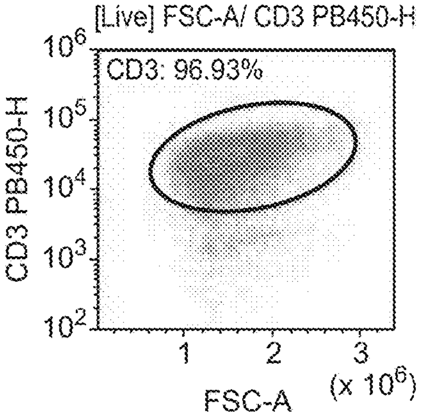
Figure 2R:
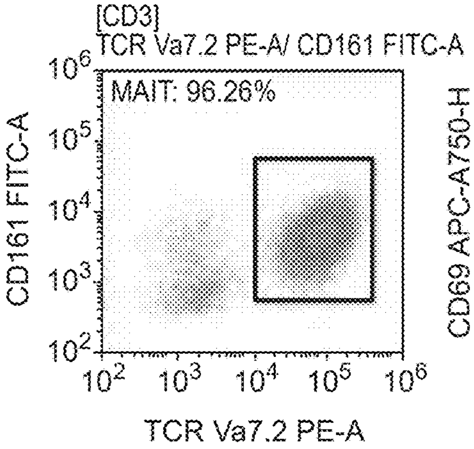
Figure 2S:
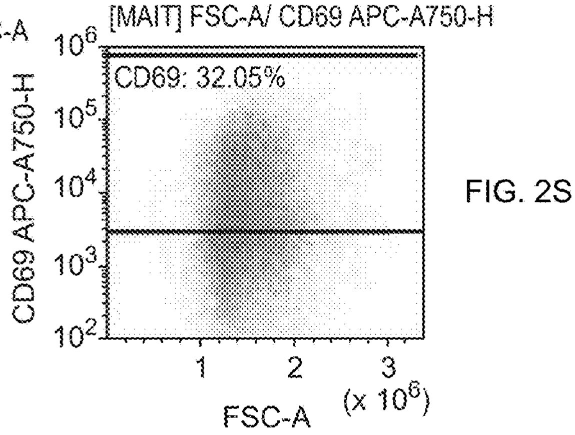
Figure 2T:
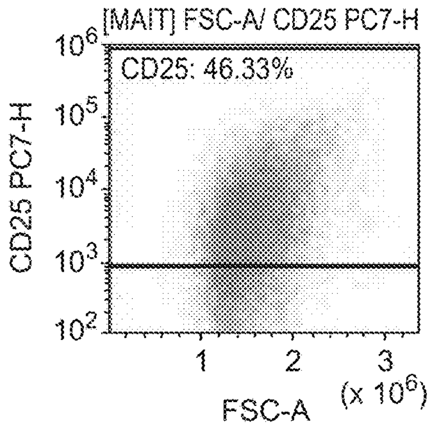
Figure 2U:
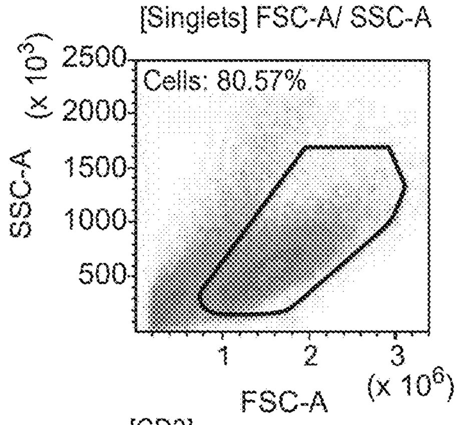
Figure 2V:
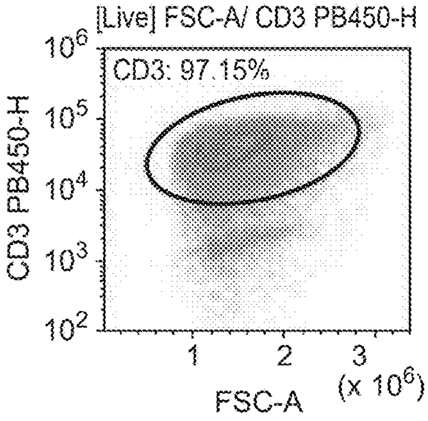
Figure 2W:
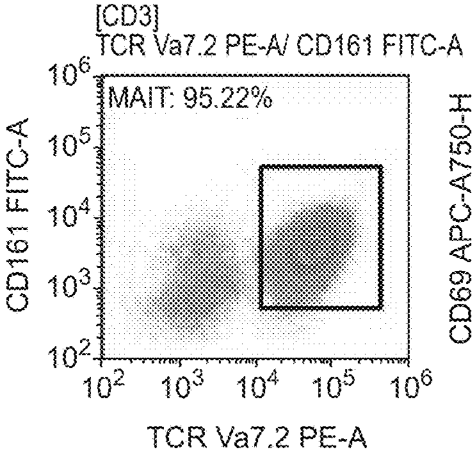
Figure 2X:
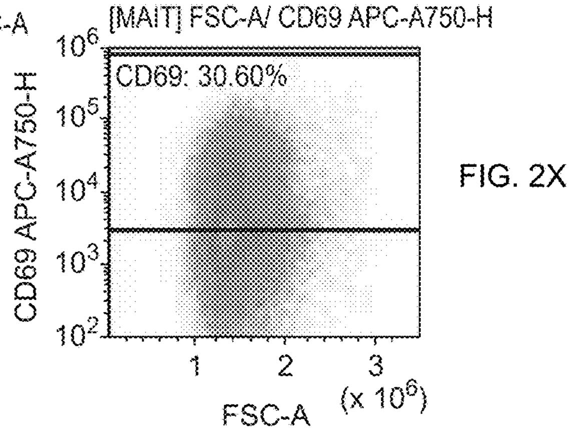
Figure 2Y:
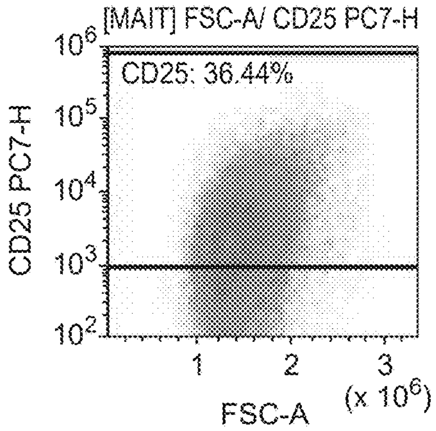
Figure 2Z:
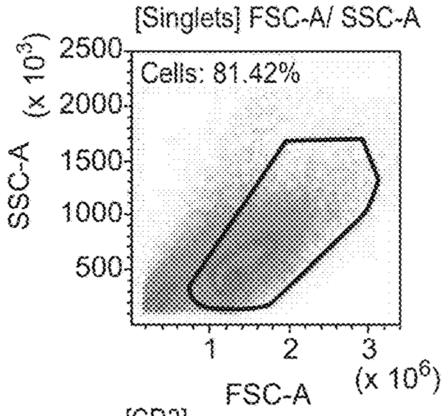
Figure 2A:
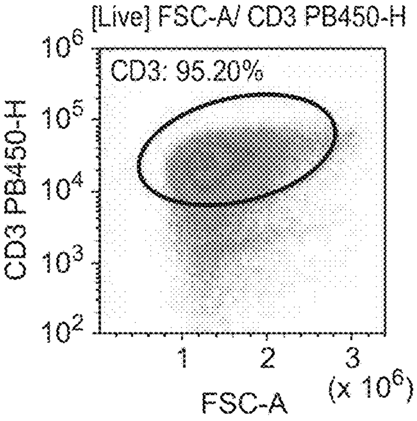
Figure 2A:
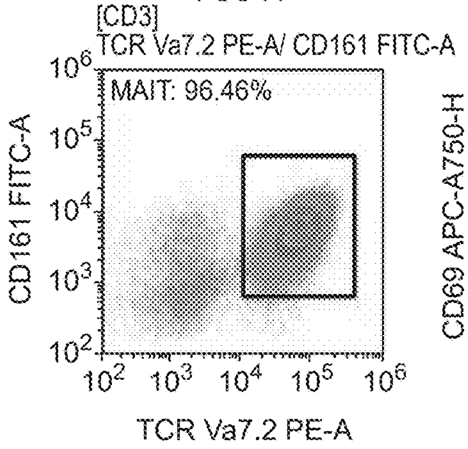
Figure 2A:
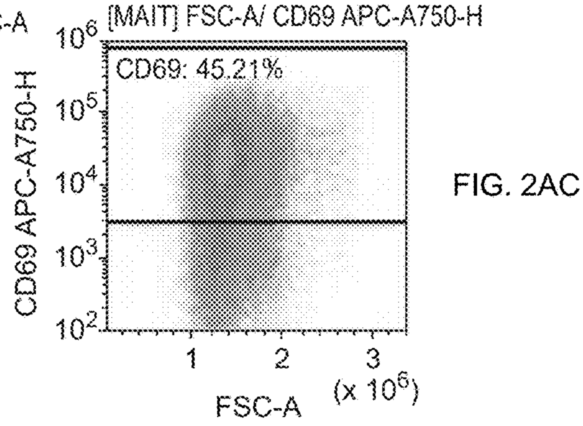
Figure 2A:
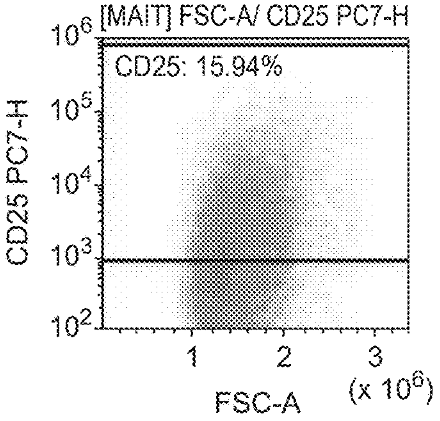
Figure 2A:
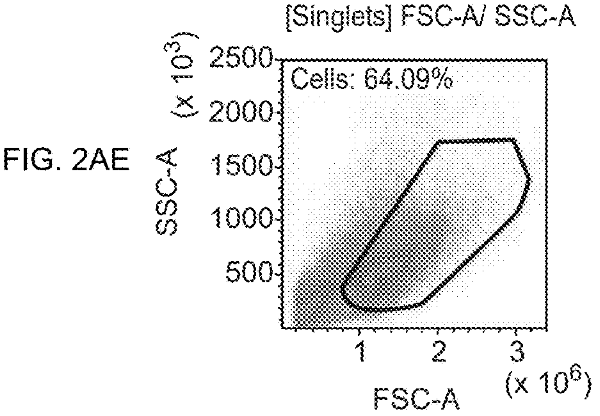
Figure 2A:
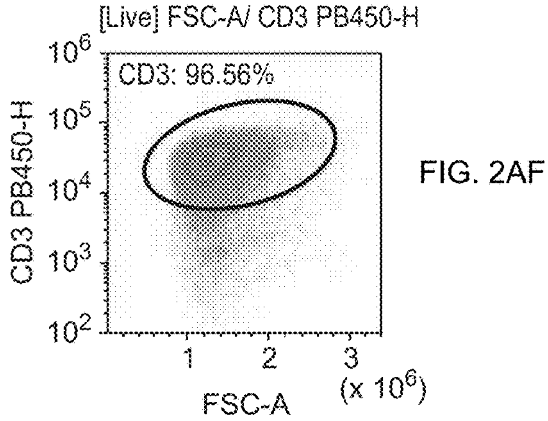
Figure 2A:
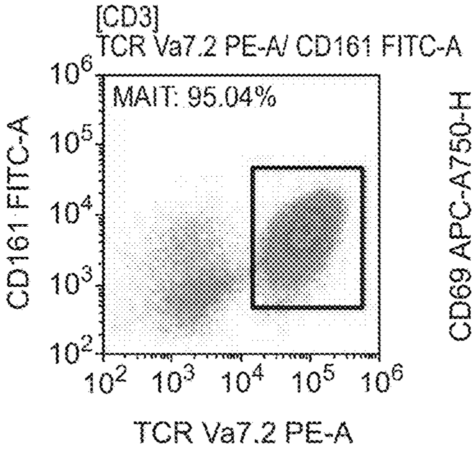
Figure 2A:
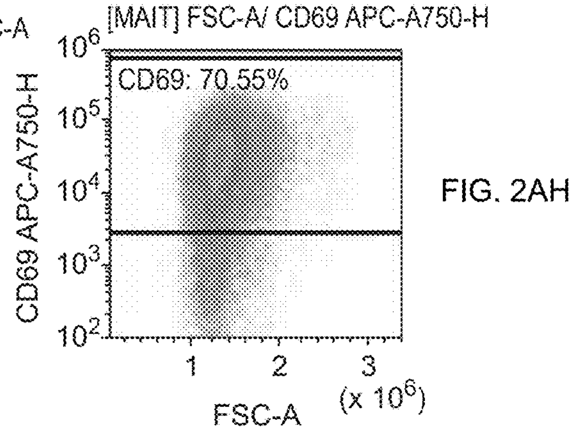
Figure 2A:
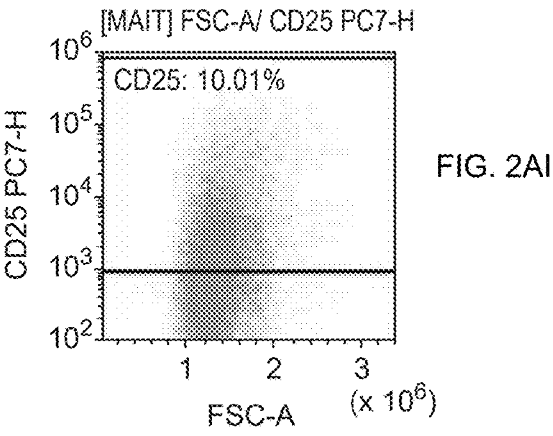

FIGS. 2A-2T present flow cytometric plots of MAIT cell's activation and proliferation for ten (10) days in a packed bed bioreactor in accordance with embodiments of the invention.

Intervillous blood (IVB)'s mononuclear cells were seeded into packed bed bioreactor containing ECM-coated Fibra-Cel® carriers which mimic the natural environment and facilitate the attachment of APCs. MAIT cells activation was induced by 5-OP-RU and IL-15. The activation and proliferation of MAIT cells were assessed at several time points: days zero (0) (FIGS. 2A-2E), five (5) (FIGS. 2F-2J), seven (7) (FIGS. 2K-2O) and ten (10) (FIGS. 2P-2T). MAIT cells population was detected by the expression of CD3, Vα7.2, and CD161 markers. The results presented an increase in the proportion of MAIT cells starting with 22.63% of the $CD3^+$ population on day zero (0) and up to 96.26% on day ten (10). Furthermore, the expression of activation markers CD69 and CD25 was elevated from day zero (0) to day seven (7) and slightly decreased by day ten (10).

FIG. 2U-2AN present flow cytometric plots of MAIT cells growth following transition of the cells from a first bioreactor to a second bioreactor on day ten (10) (FIGS. 2U-2Y) and additional seven (7) days growth in the second bioreactor in accordance with embodiments of the invention. Cells that had reached maximal growth capacity by day ten (10) in the first bioreactor were harvested, and approximately 30% of these cells were then seeded into a second bioreactor, which was similar in design to the first one. The cells were grown for an additional seven (7) days (FIGS. 2Z-2AN). Flow cytometry results demonstrated that MAIT percentages were similar during most of the time but presented a decrease from >90% at day 14 (FIGS. 2AE-2AI) to 82% at day 17 (FIGS. 2AJ-2AN). CD69 marker expression was upregulated from 30% to 87% on day 17 (FIGS. 2AJ-2AN) indicating that MAIT cells maintained their activation signal, while CD25 gradually reduced as expected, indicating that the MAIT cells have recently been activated, but have not reached their full proliferative and functional state, suggesting their ability to be reactivated and functional upon future target encounter.

Figure 3A:
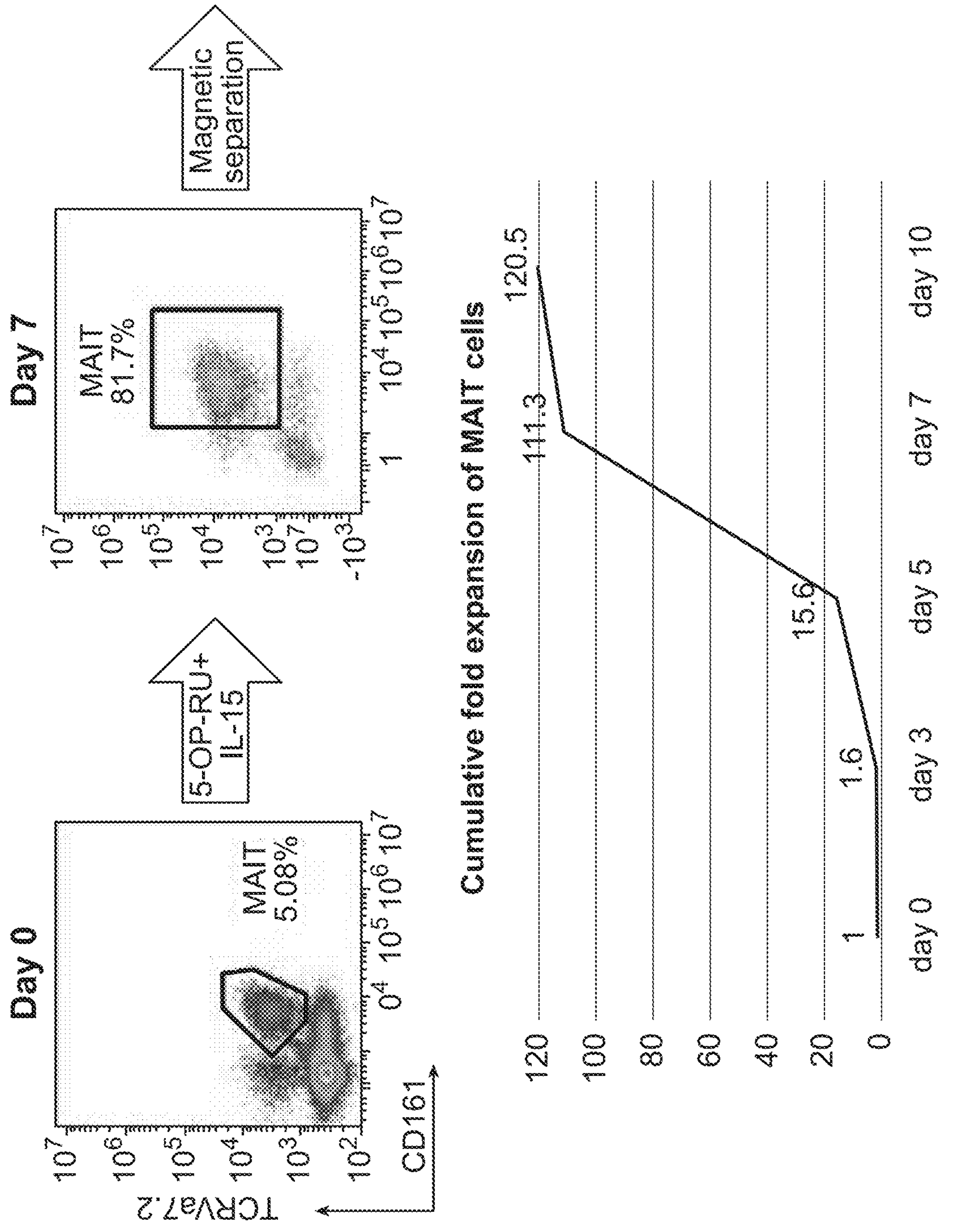
Figure 3B:
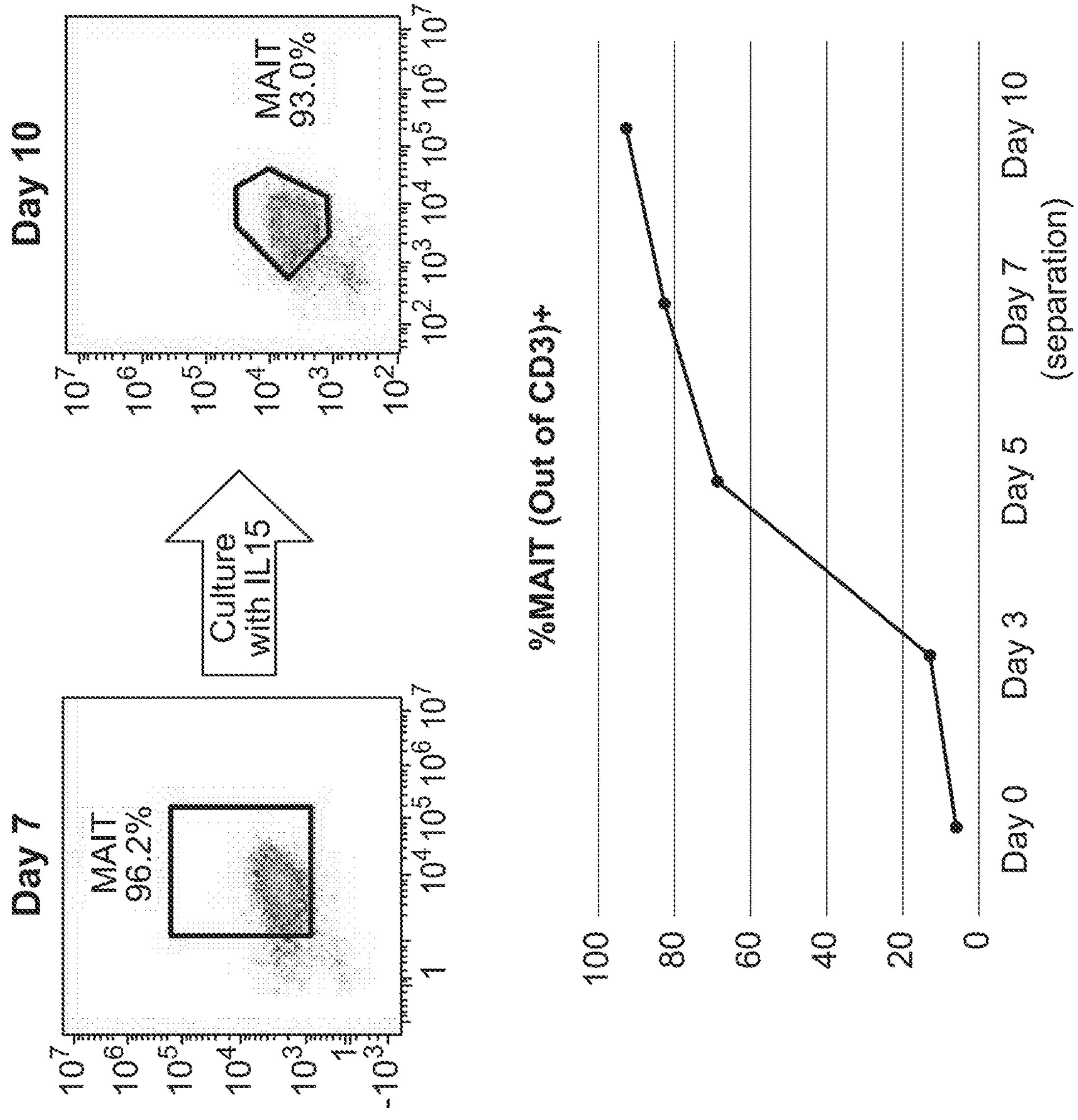

FIGS. 3A-3B show the results of placental IVB MAIT cells activation and expansion in accordance with some optional examples of the invention. IVB's mononuclear cells were seeded in tissue culture plates and MAIT cells activation was induced by 5-OP-RU and IL-15. On days three (3) and five (5) post-activation, cells were counted and analyzed by flow cytometry for MAIT percentage, and fresh medium and IL-15 was added (FIG. 3A). On day seven (7), cells were separated with magnetic beads and anti-TCR Vα7.2 antibody, to further enrich for MAIT population; cells were cultured for another three (3) days in the presence of IL-15 (FIG. 3B). The results show MAIT percentage increase and MAIT fold expansion (increase in MAIT absolute numbers relative to the starting numbers) throughout the culture period.

Figure 4A:
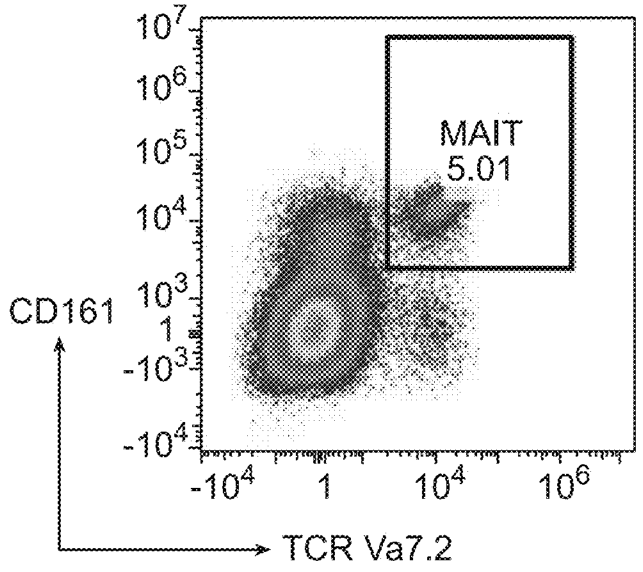
Figure 4B:
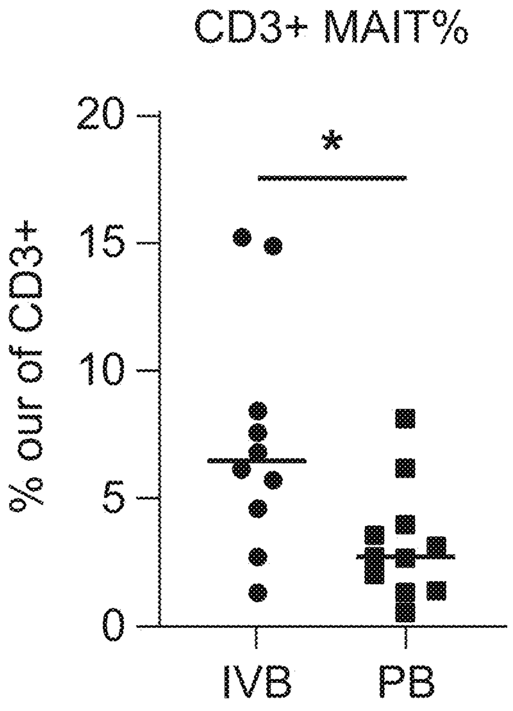

FIGS. 4A-4B show MAIT cells percentage among placenta intervillous blood (IVB) mononuclear cells and Peripheral Blood Mononuclear Cells (PBMC) gated on $CD3^+$ cells. FIG. 4A shows a representative sample of MAIT cells from placenta IVB, gated on $CD3^+$ population. FIG. 4B shows the proportion of $CD3^+$ placenta (IVB) and peripheral blood (PB) MAIT cells analyzed from thirteen (13) IVB donors and eleven (11) PB donors. $p=0.0159$.

Figures 5A, 5B, 5C, 5D, 5E, 5F:
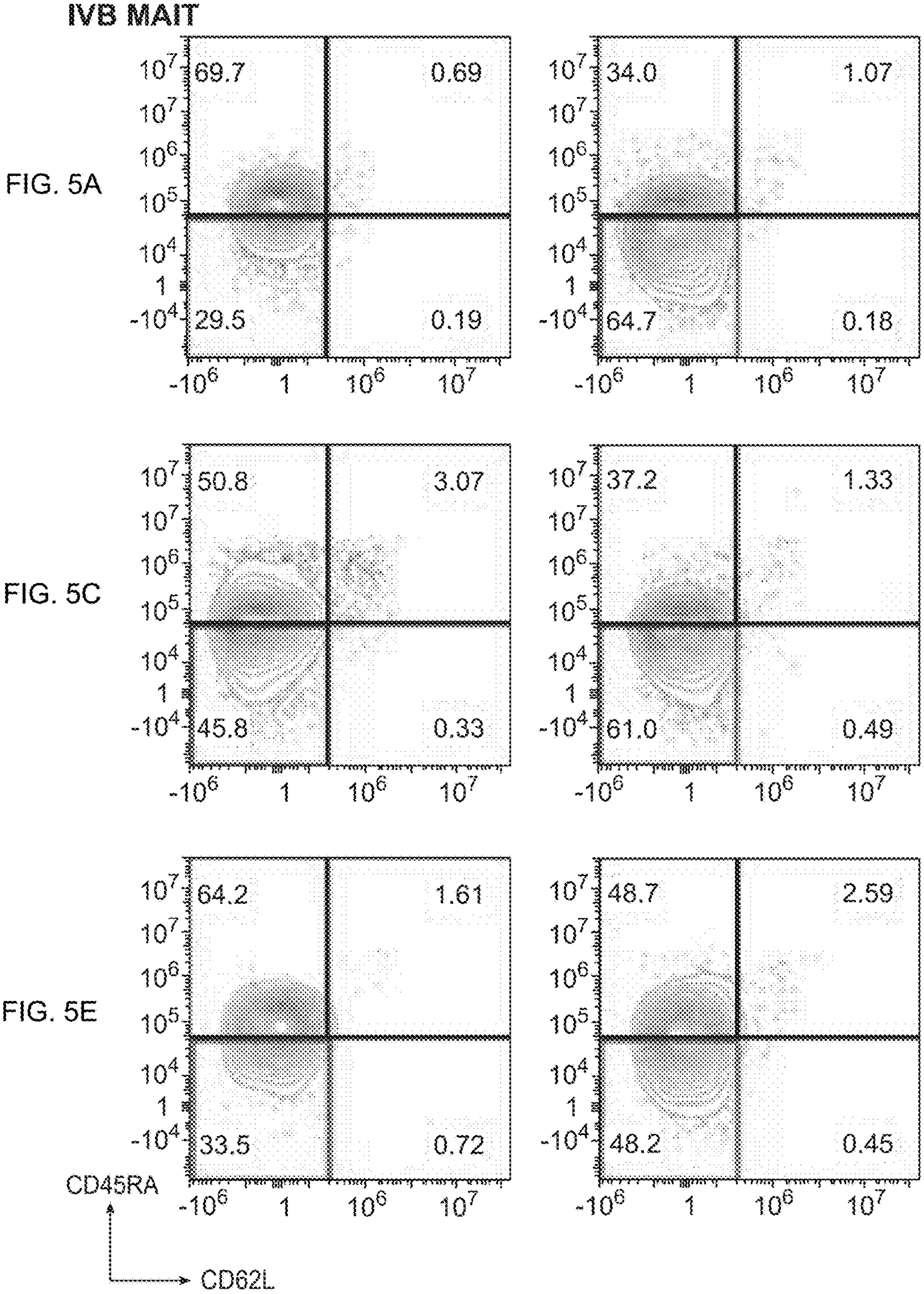
Figure 5G:
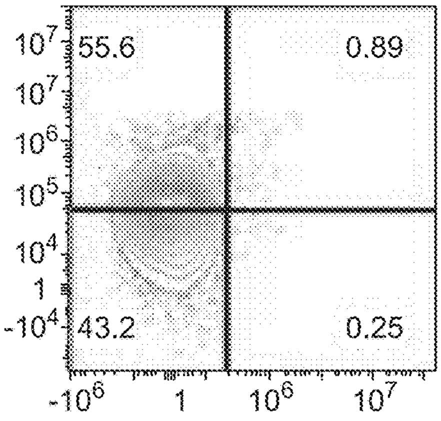
Figure 5H:
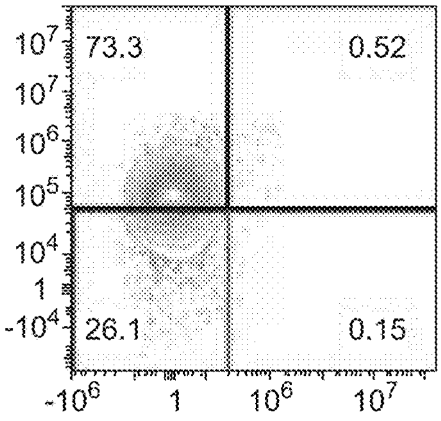
Figure 5I:
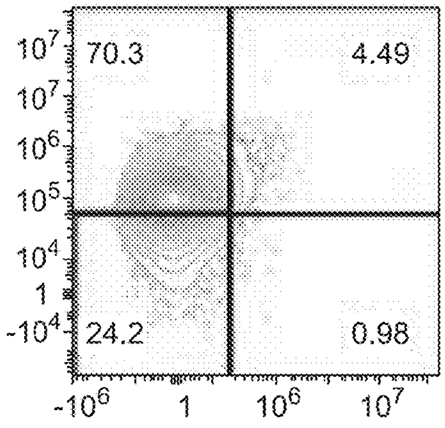
Figure 5J:
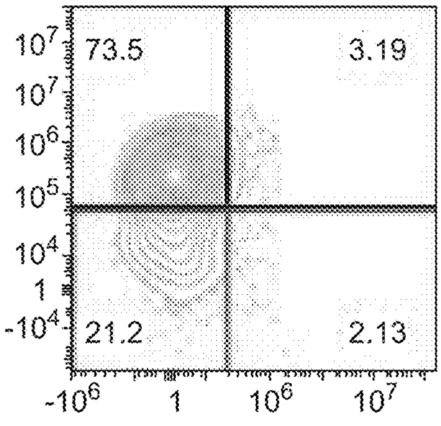
Figure 5K:
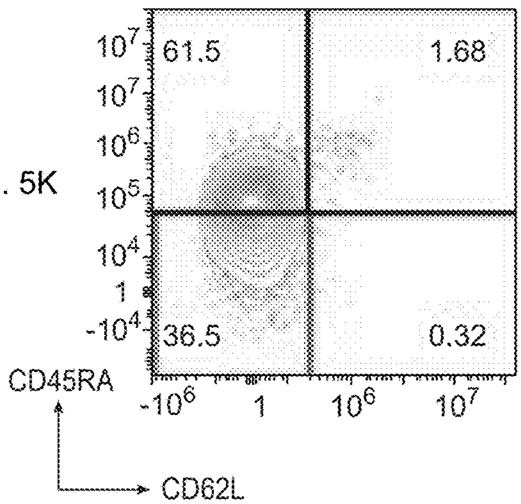
Figure 5L:
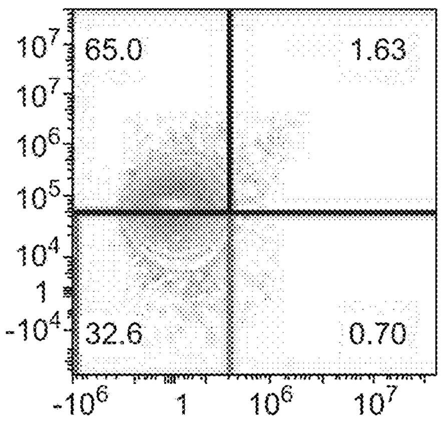
Figure 5M:
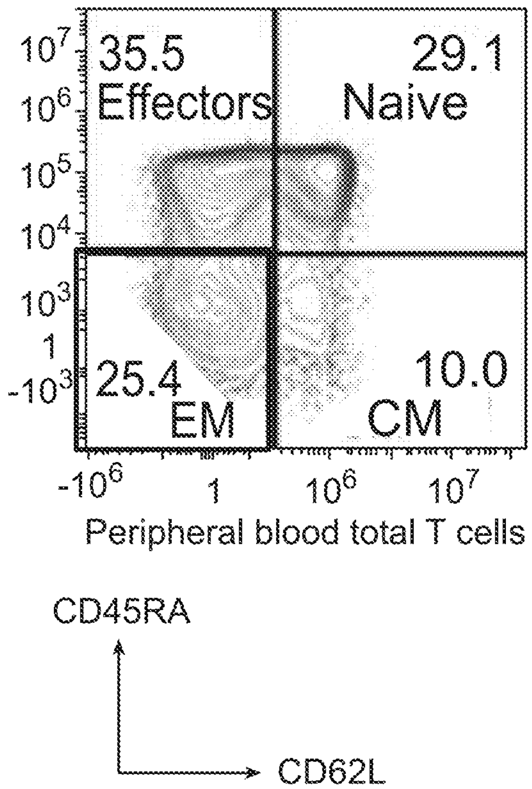
Figure 5N:
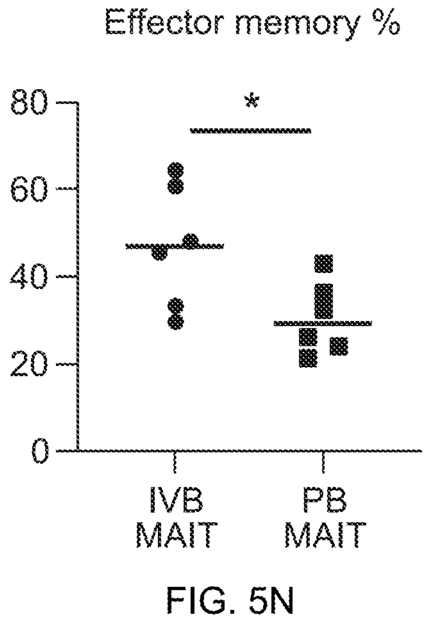
Figure 5O:
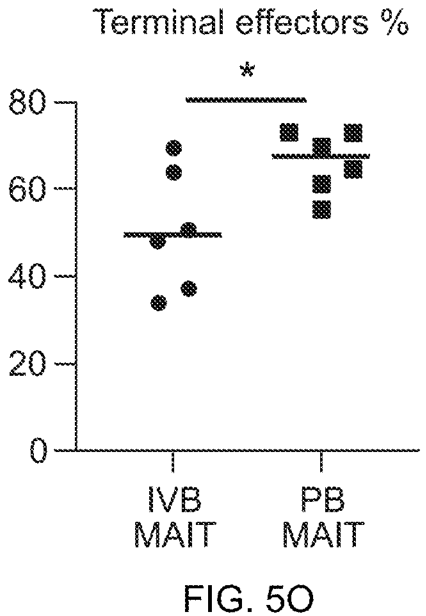

FIGS. 5A-5O show immunophenotype analysis of placental IVB MAIT cells and PB MAIT cells collected from six (6) different donors each and analyzed on day zero (0). Cells were stained according to standard cell surface marker staining protocol and analyzed by flow cytometry. Cell surface markers for CD45RA and CD62L were used to characterize the cells. As shown, Placental IVB MAIT cells have a statistically significant more "effector" memory" and less "terminally differentiated" cells compared to PB MAIT cells. Gating strategy for phenotyping is listed on the right panel. Statistical analysis was done using GP Prism, t-test comparison. *$p<0.05$, $p<0.01$, *$p<0.001$.

Figures 6A, 6B, 6C, 6D, 6E, 6F:
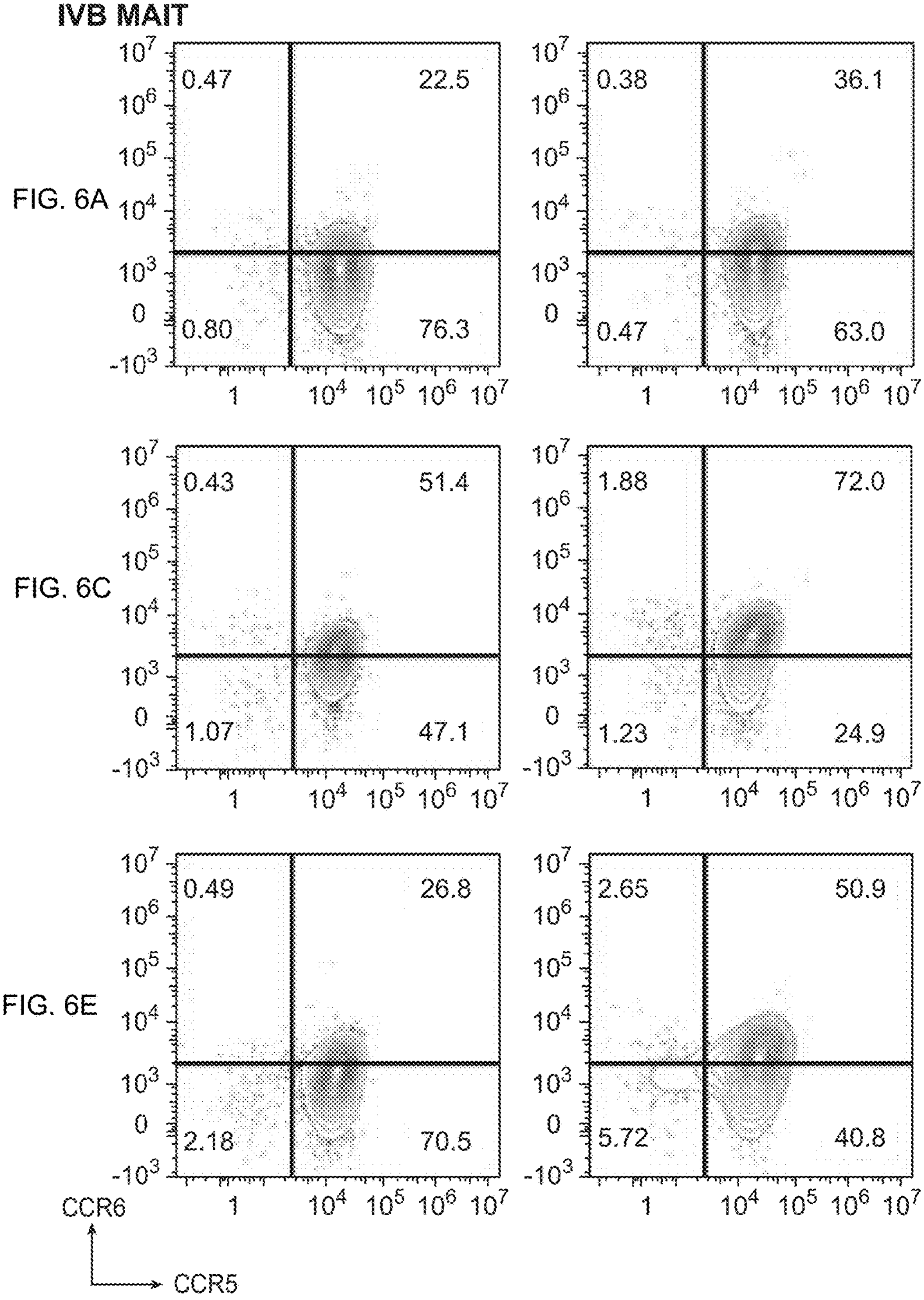
Figure 6K:
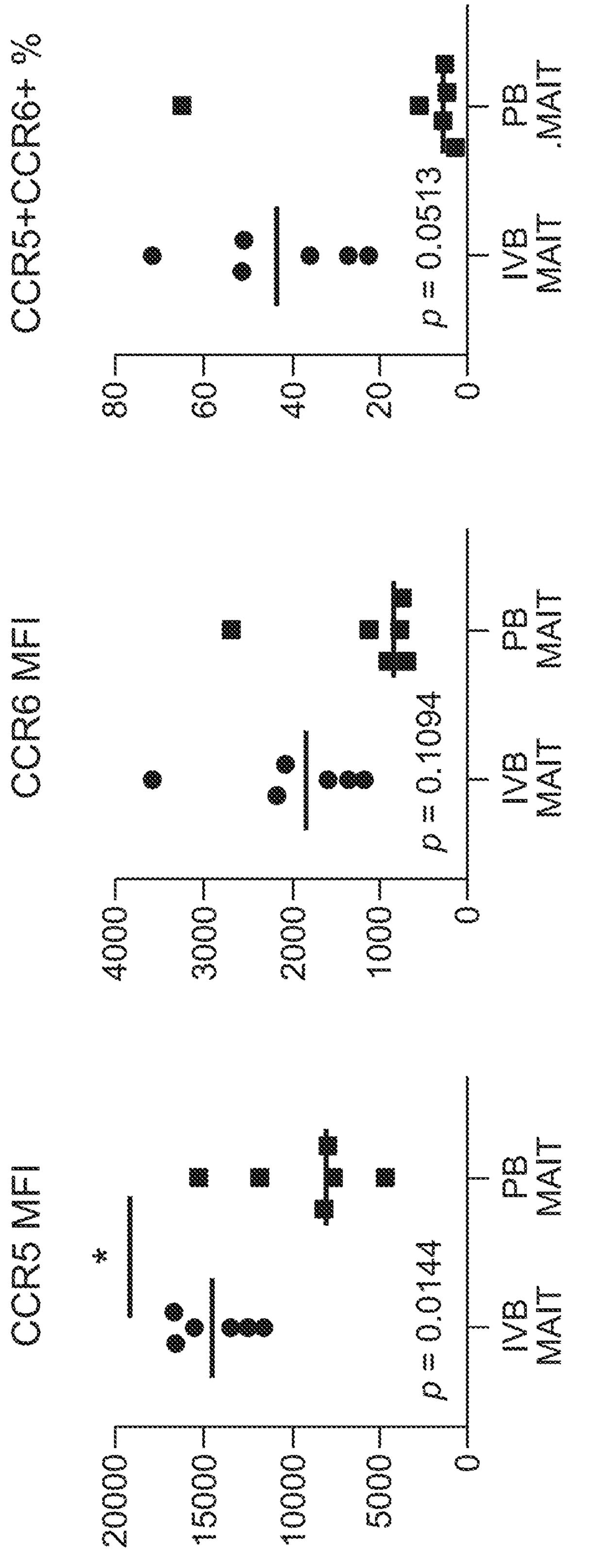
Figures 6L, 6M, 6N, 6O, 6P, 6Q:
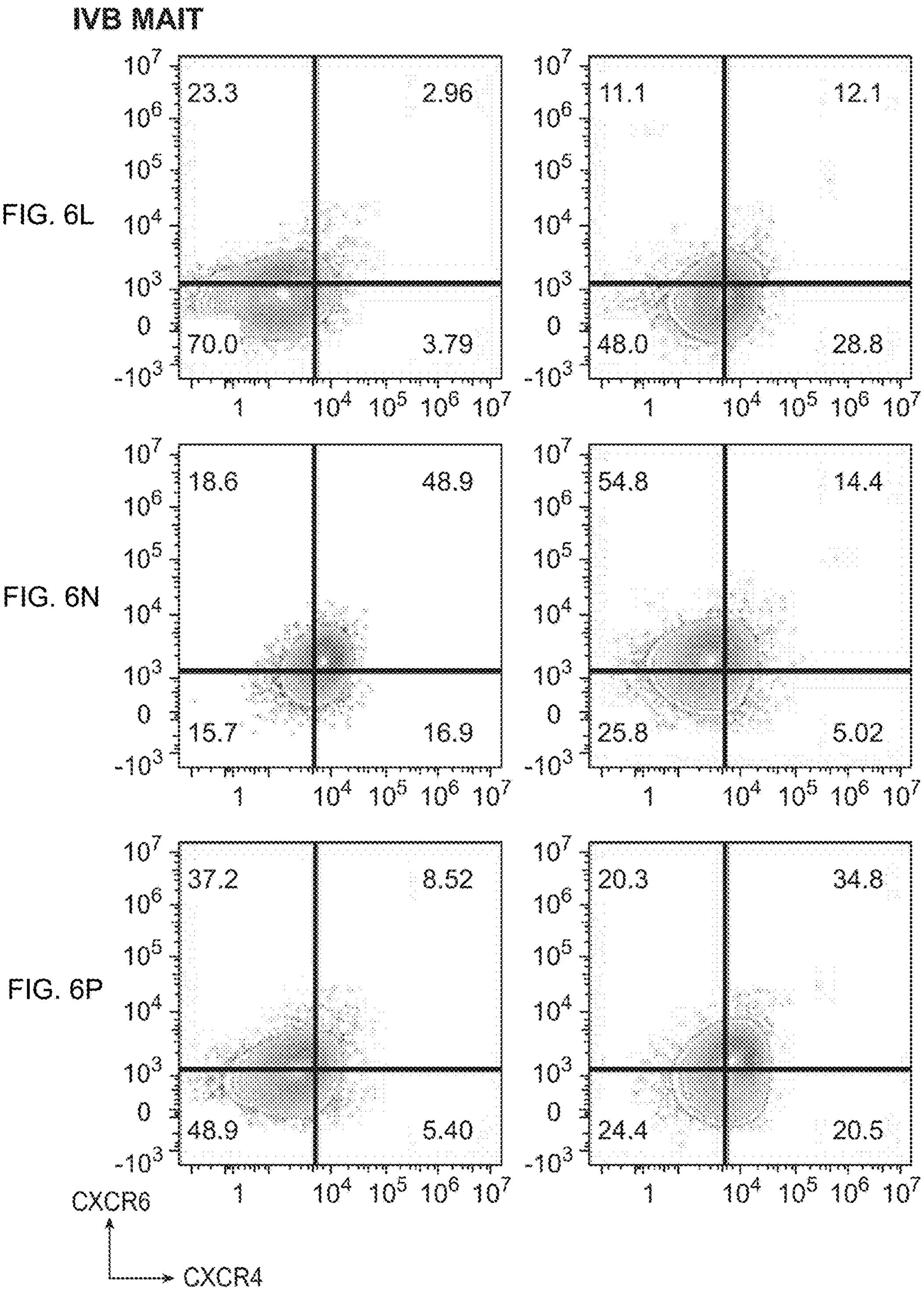
Figure 6R:
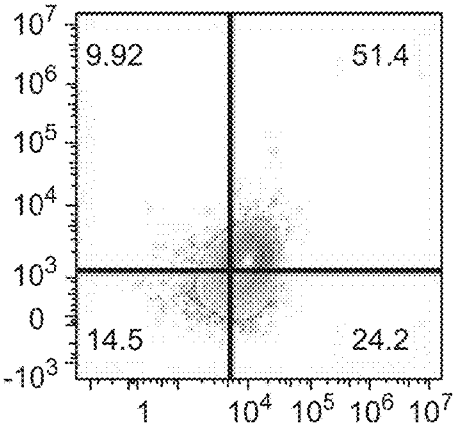
Figure 6S:
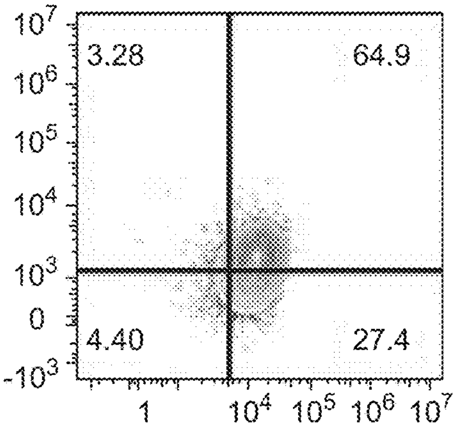
Figure 6T:
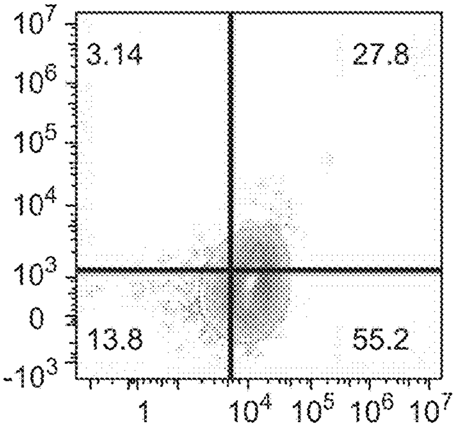
Figure 6U:
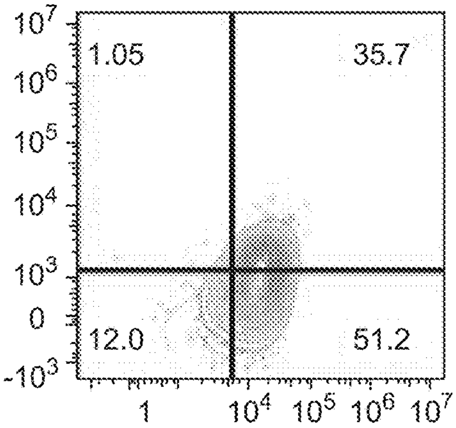
Figure 6V:
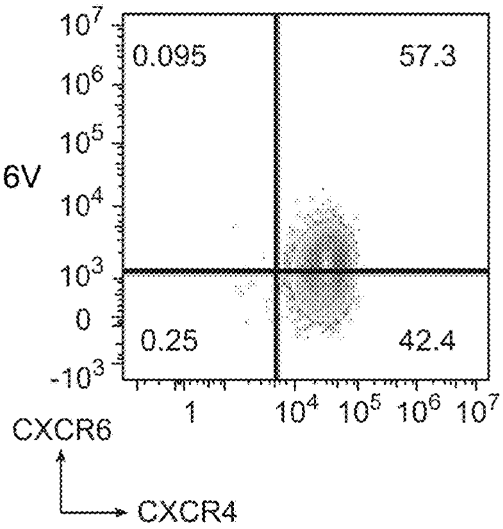
Figure 6W:
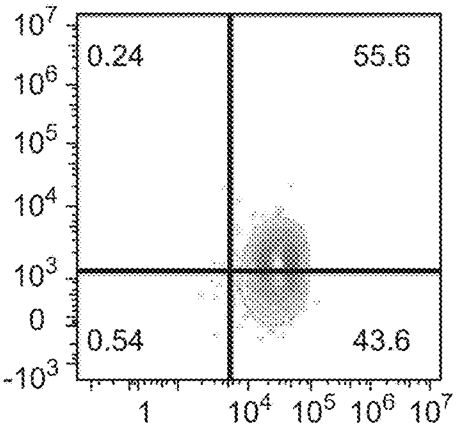

FIGS. 6A-6AA show Chemokine receptor analysis of placental IVB MAIT cells and PB MAIT cells in accordance with examples of the invention. To evaluate the chemokine receptor profile of MAIT population IVB MAIT cells and PB MAIT cells were collected from six (6) different donors each and analyzed on day zero (0) for chemokine receptor expression. Cell surface markers for CCR6, CCR5, CXCR4 and CXCR6 were used to characterize the cells. Cells were stained according to standard cell surface marker staining protocol and analyzed by flow cytometry. Statistical analysis was done using GP Prism, t-test comparison. *$p<0.05$,  $p<0.01$, * $p<0.001$. FIG. 6A-6K show that IVB MAIT cells have higher expression of CCR5 and CCR6 chemokine receptors compared to PB MAIT cells. FIG. 6L-6AA show that IVB MAIT cells have statistically significantly lower levels of CXCR4 and comparable levels of CXCR6 compared to PB MAIT cells. The results further exemplify that the two MAIT cell populations derived from IVB and from PB are different.

Figure 7A:
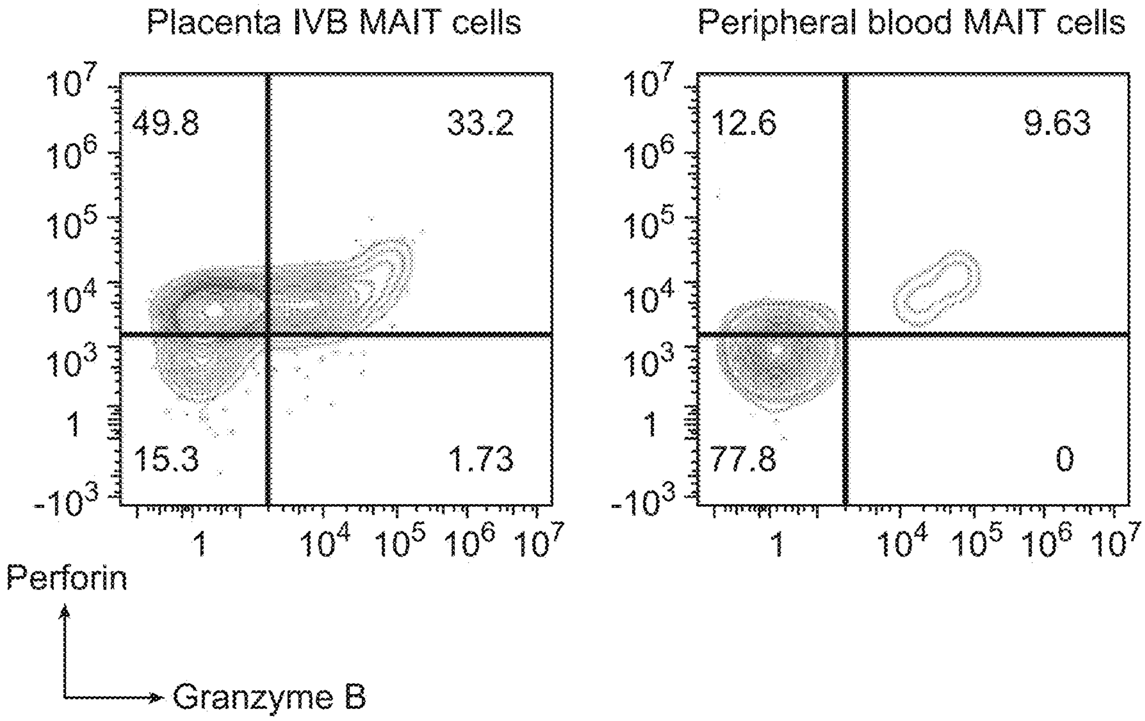
Figure 7B:
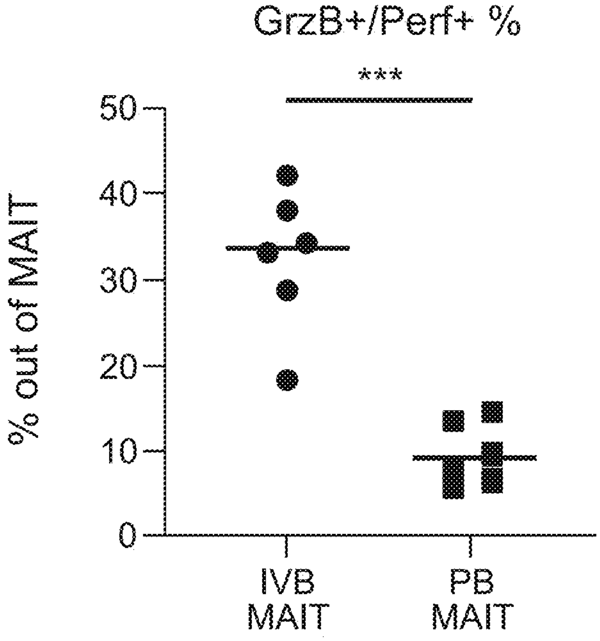

FIGS. 7A-7B show expression of Granzyme B and Perforin in placenta IVB MAIT cells and in peripheral blood MAIT cells. FIG. 7A shows a representative sample for both cell types. FIG. 7B shows MAIT cells from placenta IVB and from peripheral blood.

Cells from six (6) donors each, were stimulated with PMA/Ionomycin for four (4) hours and analyzed for intracellular expression of Granzyme B and Perforin. As shown, placental IVB MAIT cells have statistically significantly higher levels of Granzyme B compared to peripheral blood MAIT cells indicating an increased effector and lytic capacity of the placental IVB MAIT. Cells were gated on MAIT cells. $p=0.0001$.

Figure 8A:
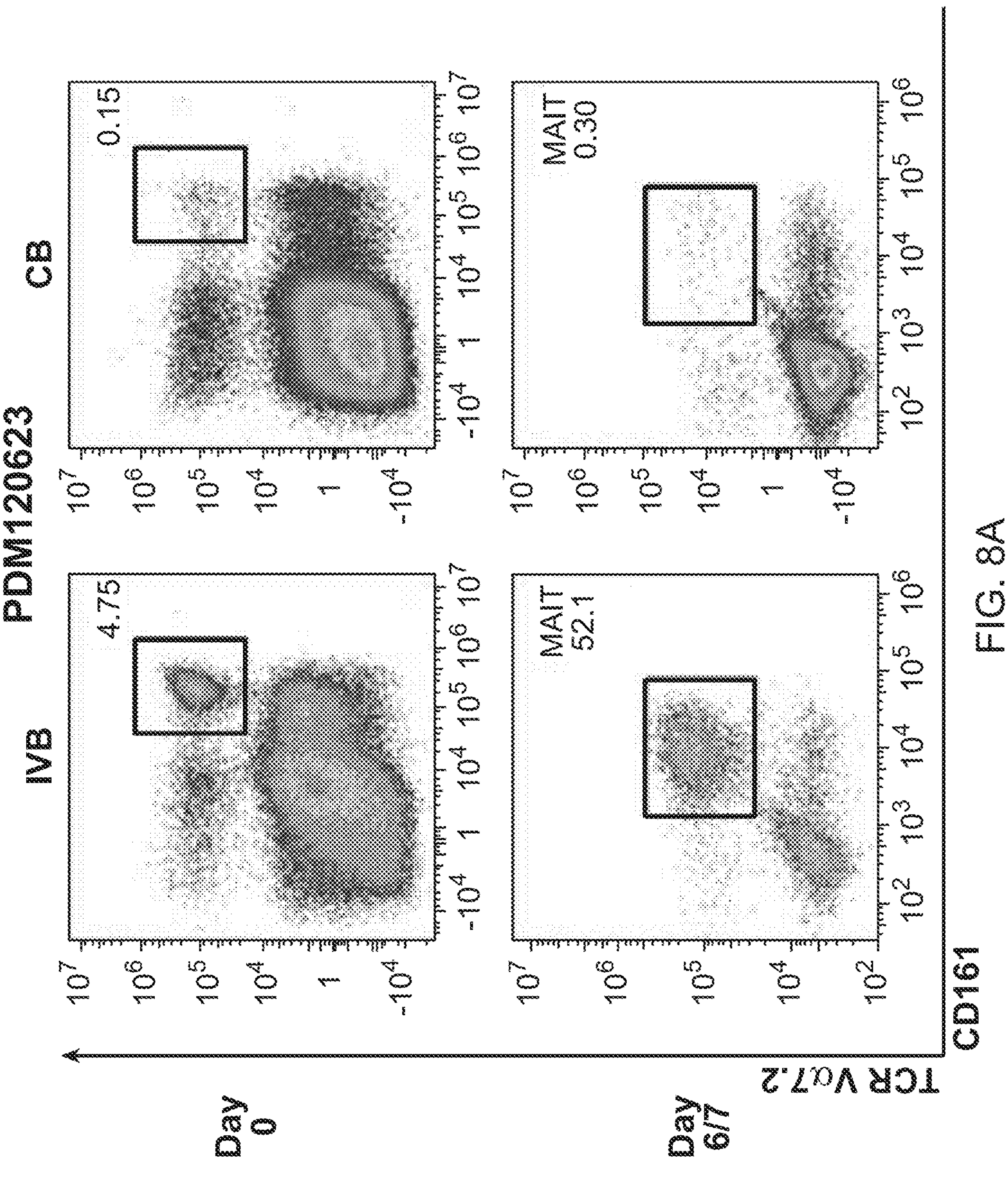
Figure 8B:
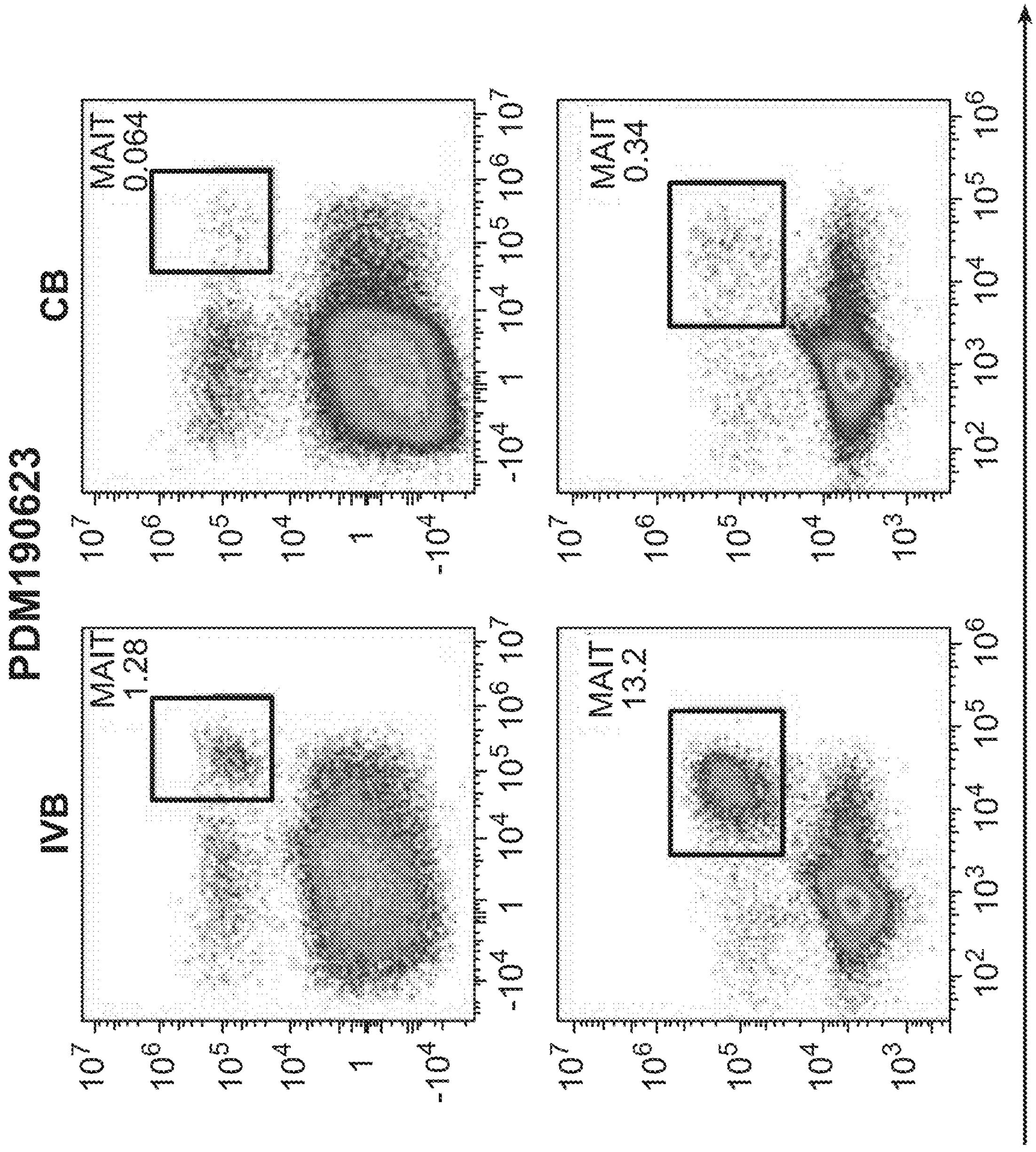

FIGS. 8A-8C present flow cytometric plots of MAIT cells percentage among placental intervillous blood (IVB) and matched (same donor) cord blood (CB) (FIGS. 8A-8B); and a table summarizing the results obtained in the flow cytometric plots (FIG. 8C).

Cells from three (3) different donors were taken as previously described. IVB cells and CB cells were activated similarly. As shown, CB has very few MAIT cells on day zero (0) compared to IVB, and their percentage is decreasing over time (days 6/7). In more detail, IVB MAIT and matched CB MAIT cells were collected according to protocols as described in the material and methods below. The cells were stained on day 0 and on days 6/7 for CD161 and TCR Vα7.2 which represent MAIT positive gating strategy. Squared gate represent the percentage of MAIT cells. The table describes the actual cell counts. As observed, Intervillous blood (IVB) has much more MAIT cells compared to cord blood (CB).

Figure 9:
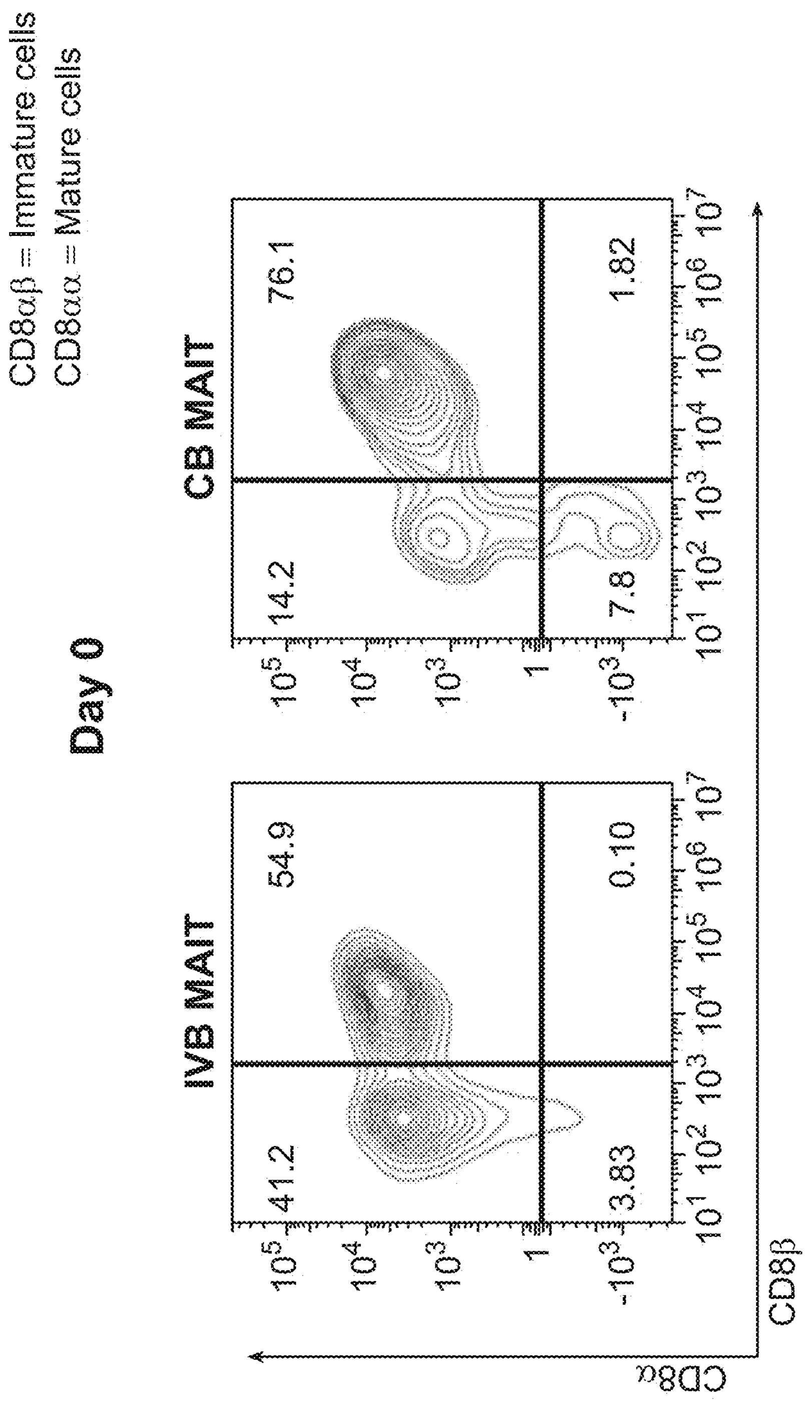

FIG. 9 shows flow cytometric plots of placental IVB MAIT cells and CB MAIT cells expression of CD8αα+ in accordance with examples of the invention.

As shows in the flow cytometric plots, the placental IVB MAIT cells express high frequency of CD8αα+ at a three (3) times higher frequency (41.2%) compared to CB MAIT cells (14.2%), indicating on a more "antigen experienced" phenotype compared to the naive state present in the CB MAIT cells.

CD8α is a cell surface glycoprotein that can be expressed either as a disulfide-linked heterodimer together with CD8β or as a homodimer. In contrast to CD8αβ, CD8αα is never expressed on naïve T cells but readily induced on strongly activated T cells. In addition, CD8αα may act like other "tuning" molecules to aid survival, in a manner analogous to expression of KIRs or other NK cell associated receptors on T. MAIT cells from IVB and CB were stained for the two CD8 subunits, CD8α and CD8β and frequency was measured by flow cytometry. The results show that IVB MAIT cells have higher frequency of CD8αα indicating on a more mature and "antigen experienced" phenotype compared to CB MAIT cells.

Figure 10A:
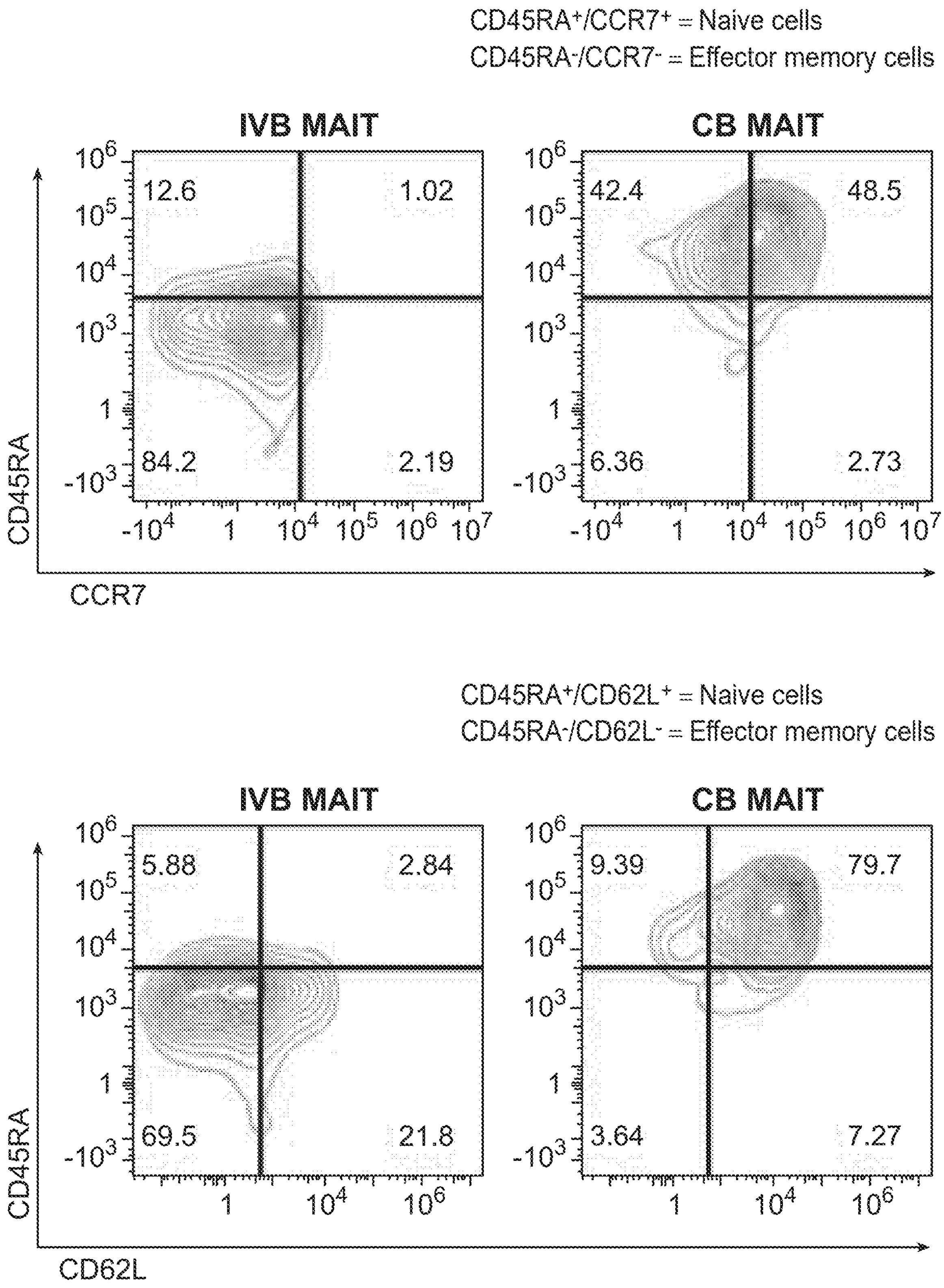
Figure 10B:
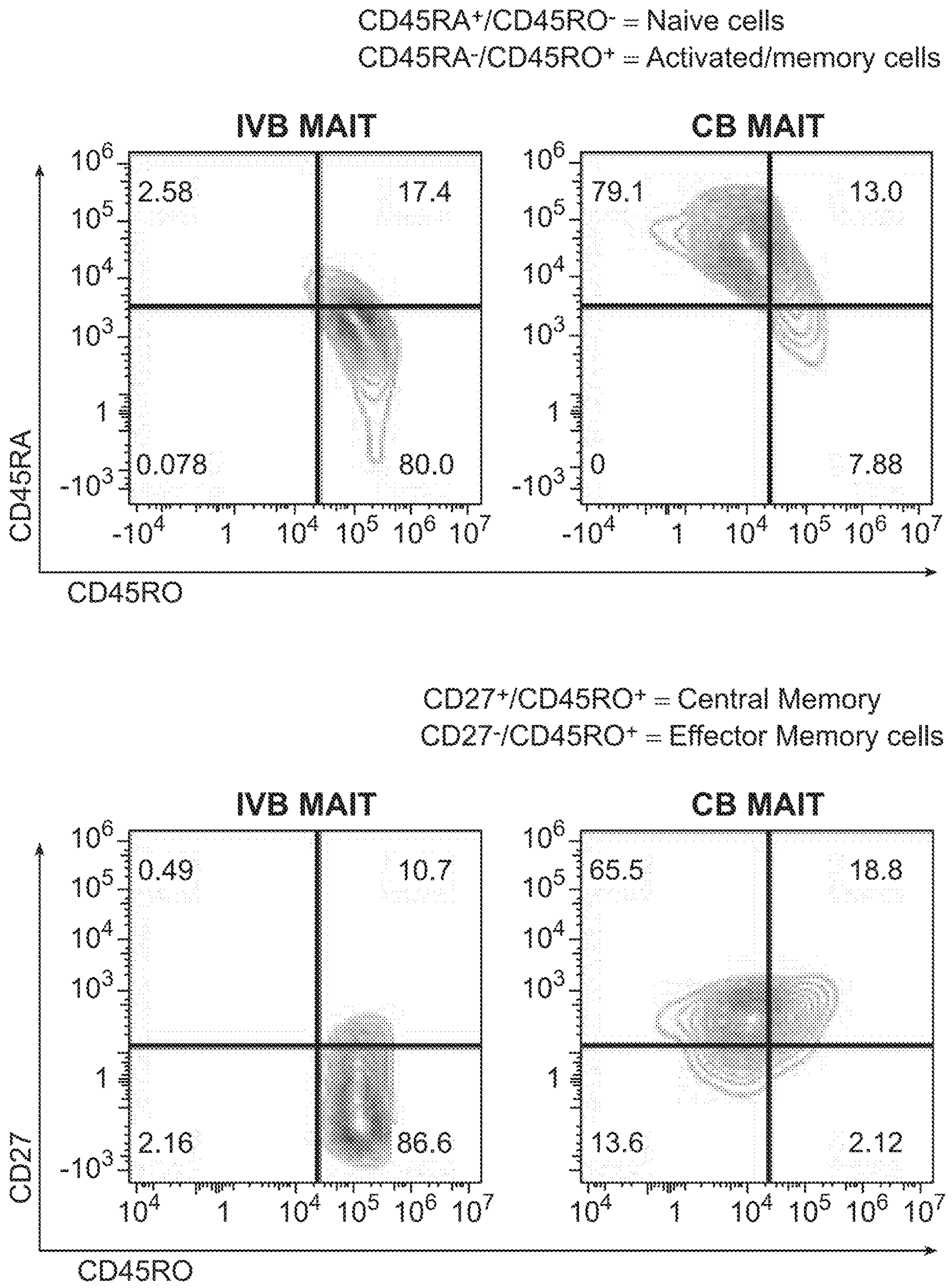

FIGS. 10A-10B show flow cytometric plots of placental IVB MAIT cells and CB MAIT cells for effector phenotype using CD45RO, CD27, CD45RA, CCR7 and CD62L.

IVB MAIT and matched CB MAIT were collected according to methods described in the material and methods below. Cell surface markers for CD45RA, CD27, CCR7 CD62L and CD45RO were used to determine the cells immunophenotyping, where $CD45RA^-/CCR7^-$ $CD45RA^-/CD62L^-$, $CD45RA^-/CD45RO^+$ and $CD27^-/CD45RO^+$ represent an effector memory cell, effector memory cell, activated memory cell and effector memory phenotype respectively. As clearly shown in the flow cytometric plots, IVB MAIT cells defer from CB MAIT cells as IVB MAIT cells possess an effector memory phenotype whereas CB MAIT cells present a naïve phenotype.

Figure 11:
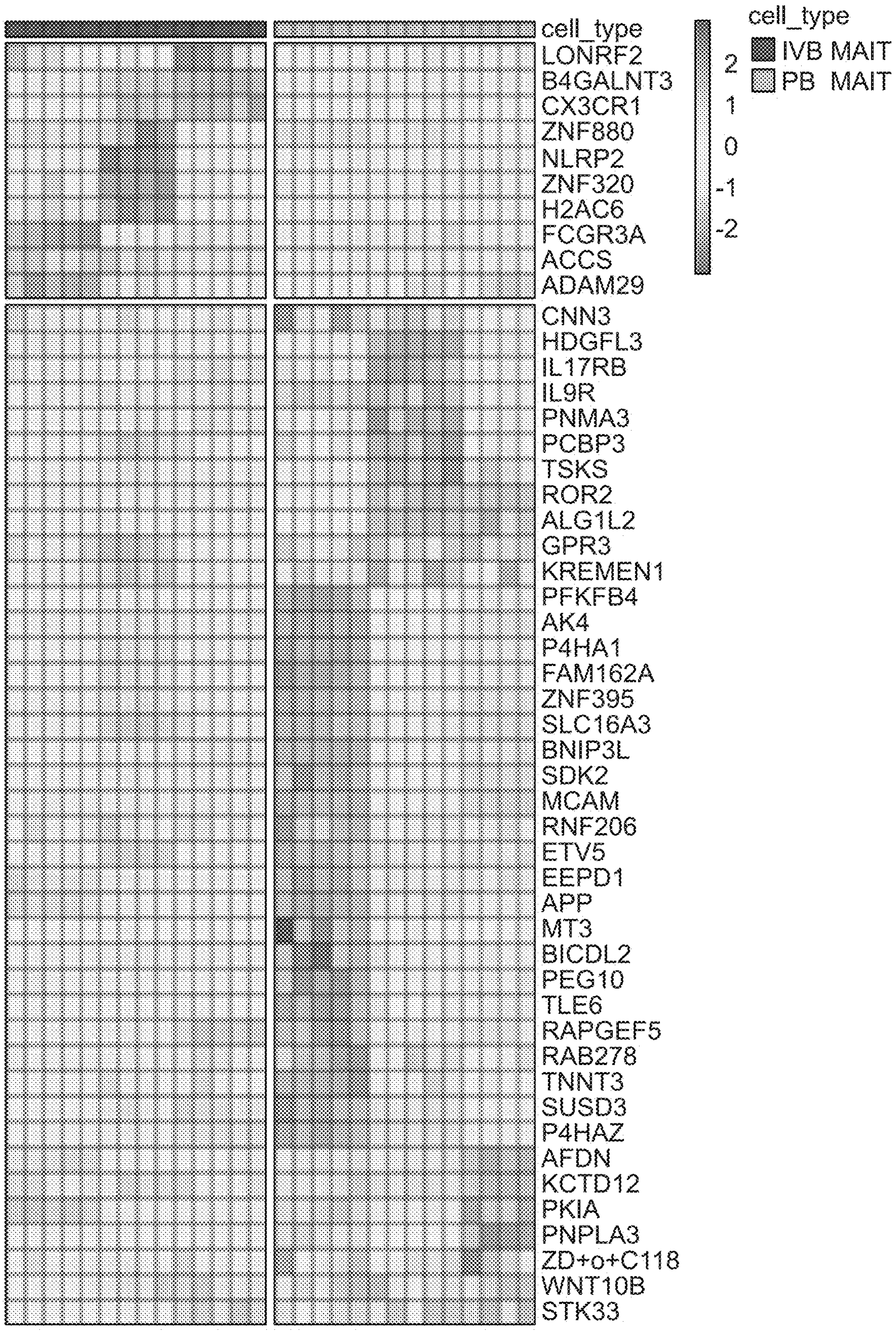
Figure 12A:
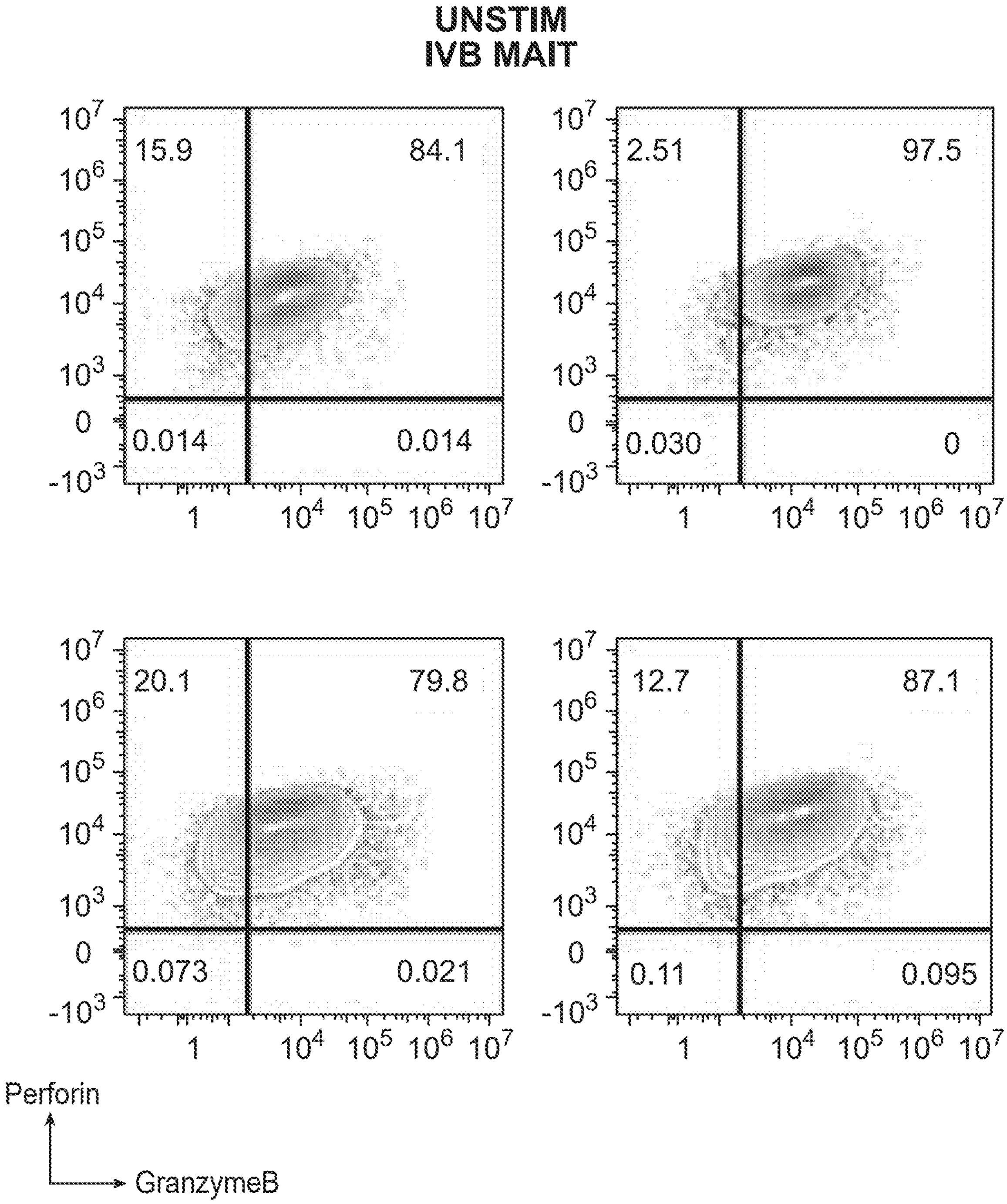
Figure 12B:
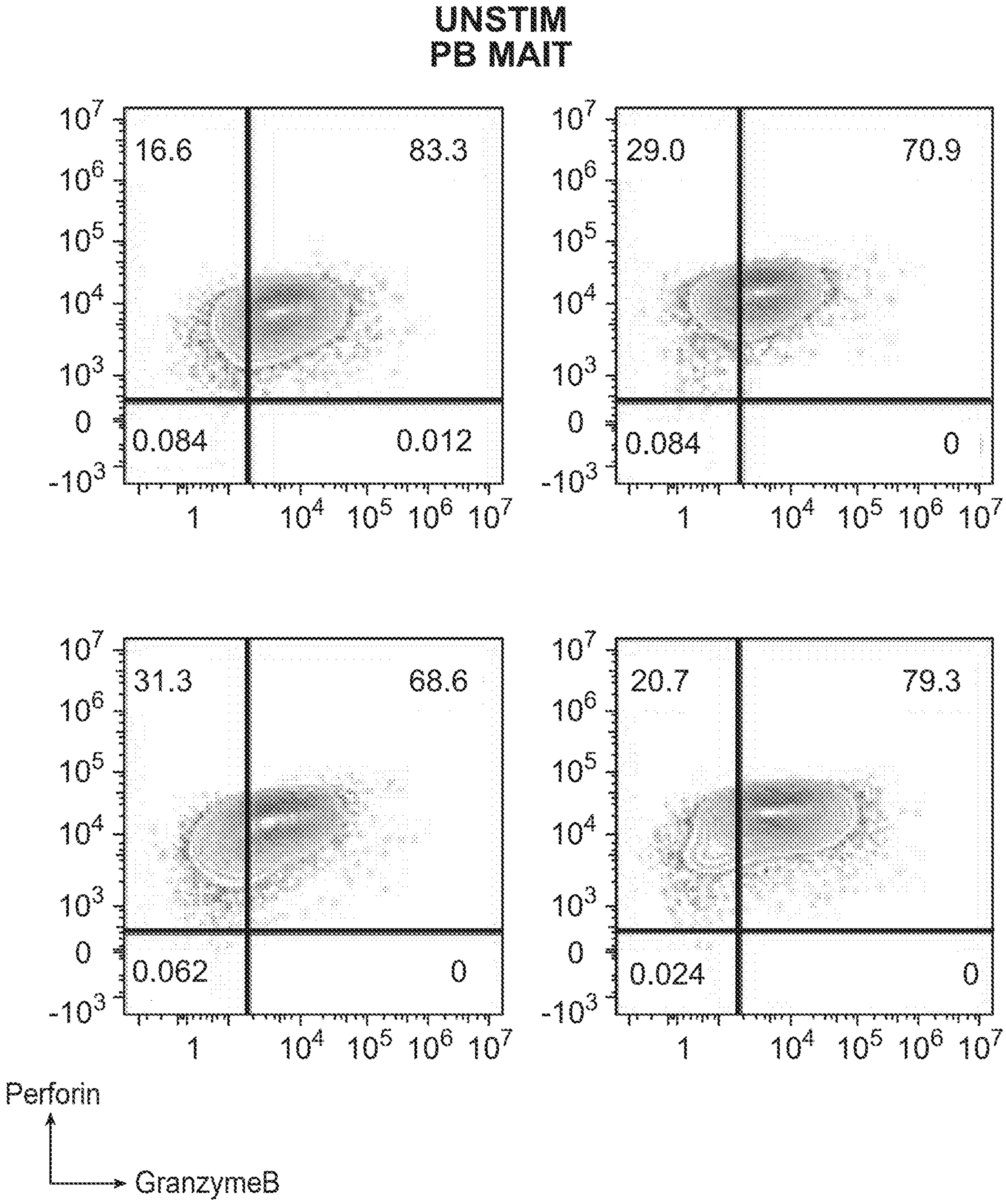
Figure 12C:
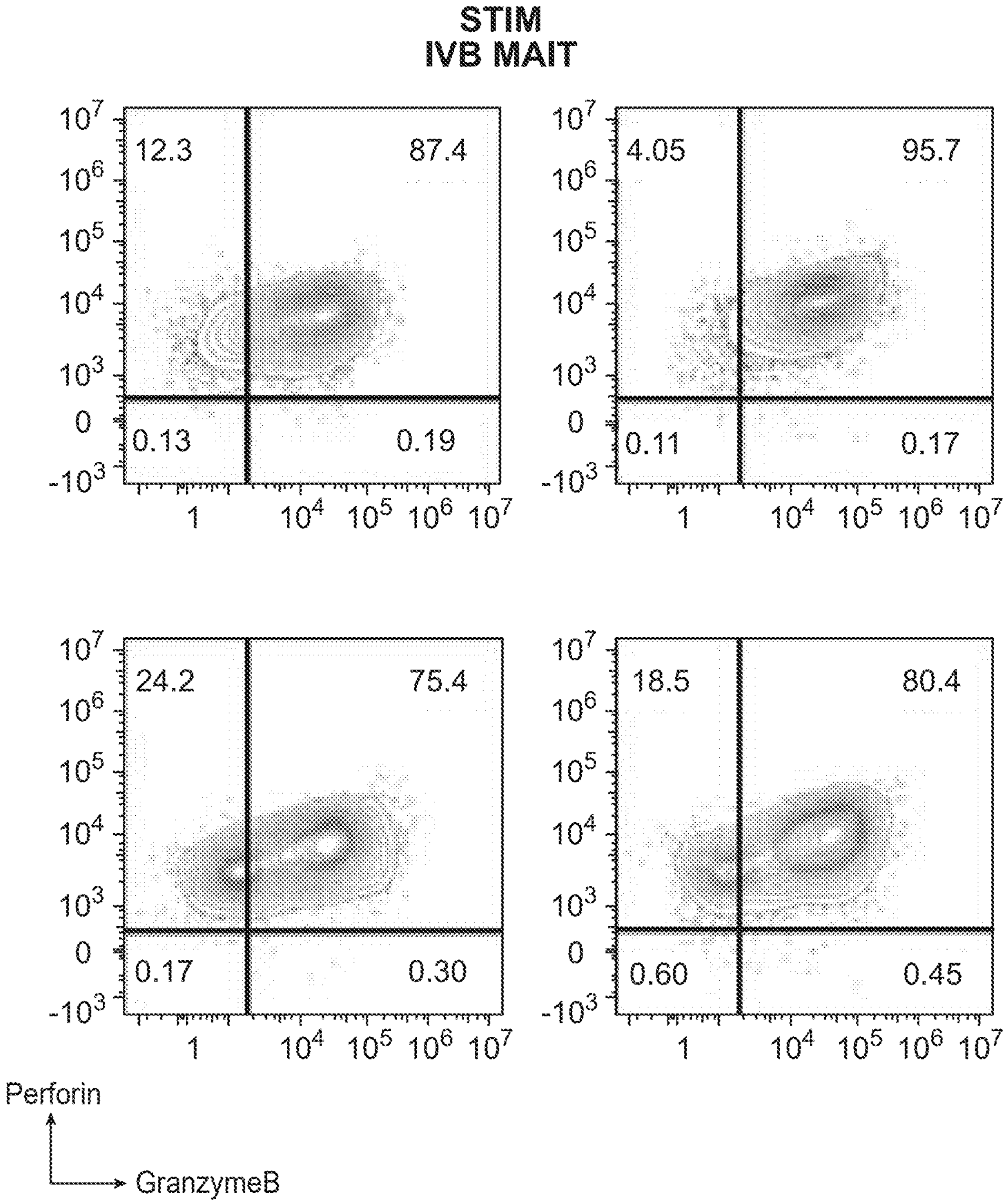
Figure 12D:
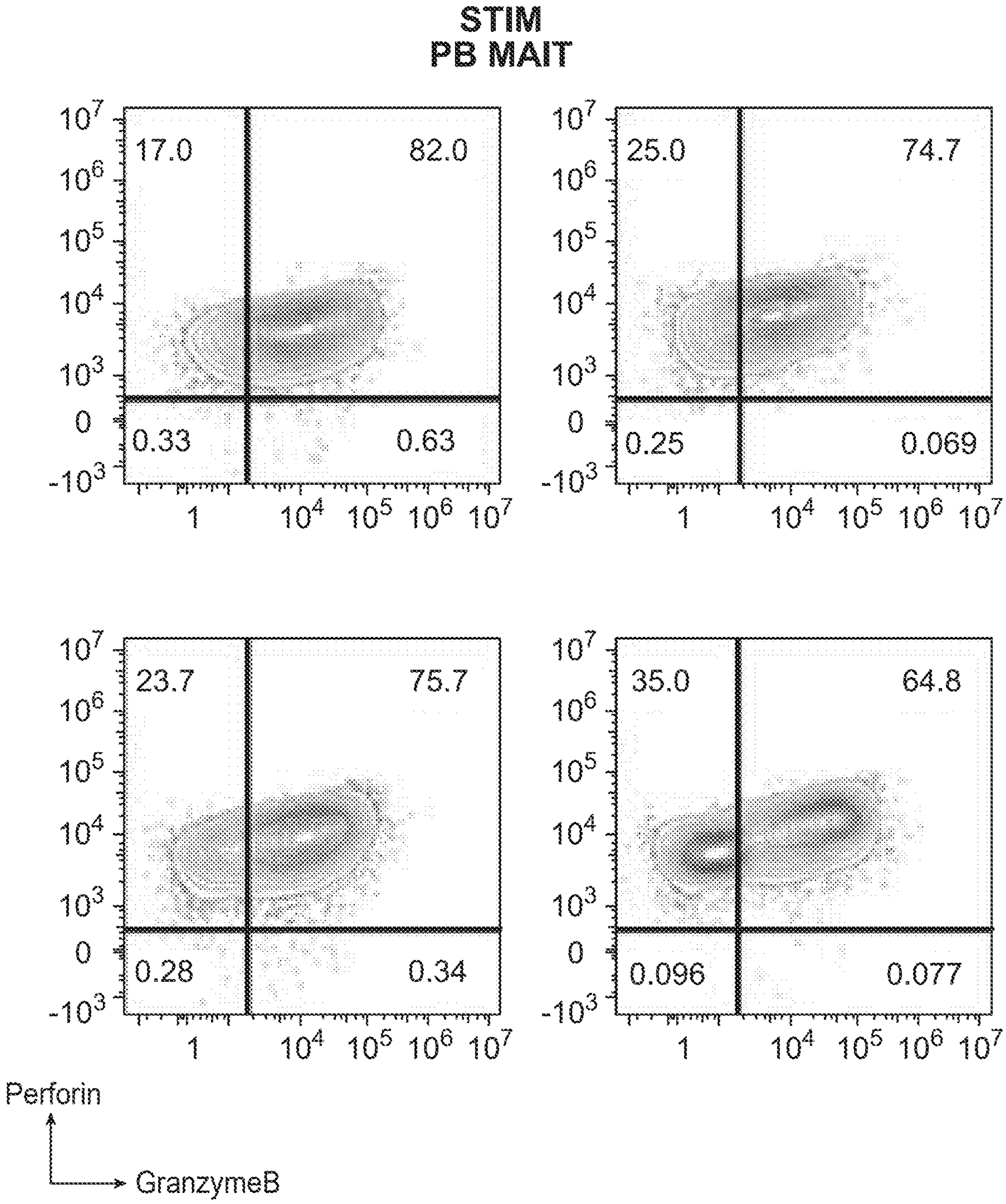
Figure 12E:
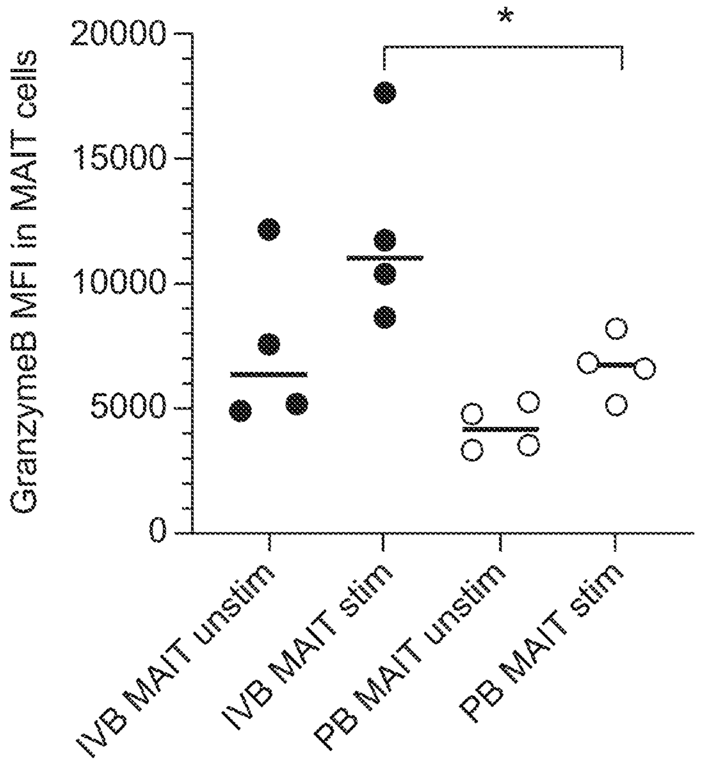

FIG. 11 is a Transcriptome analysis of IVB MAIT cells and PB MAIT cells showing a set of top 50 differentially expressed genes.

In order to understand transcriptomic differences between MAIT cells derived from different tissues, i.e. PBMCs and IVB, cells were extracted and expanded as described in methods, and an RNAseq analysis was performed. IVB and PB MAIT cells were collected from three (3) different donors each and analyzed on day seven (7) for RNAseq transcriptome analysis. Cells were harvested according to the description in methods. Heatmaps of significantly ($|\log 2FC|>1$) and BH padj<0.01) differentially expressed protein coding genes between IVB and PB cell types. The clustering was performed applying the Pearson correlation calculation on the normalized values of the count data. The color scheme represents the z-scores. As shown, MAIT originating from IVB possess a unique and distinctive transcriptome landscape compared to peripheral blood MAIT cells, meaning that the two MAIT populations are highly distinctive from one another. The names of the 50 top genes are listed in the figure.

FIG. 12A-12E show a comparison between IVB MAIT cells and PB MAIT cells for Granzyme B secretion. Placental IVB MAIT cells and PB MAIT cells were collected from four (4) donors each and expanded using a standard protocol as described in the Methods section. On day Eight (8) cells were activated with Phorbol Myristate Acetate (PMA) plus Ionomycin and analyzed for Granzyme B and Perforin secretion, using a standard intra-cellular staining protocol. Granzyme B is a serine protease found in granules of lytic cells. It is secreted along with the pore forming protein, Perforin, to mediate apoptosis of target cells.

Figure 13:
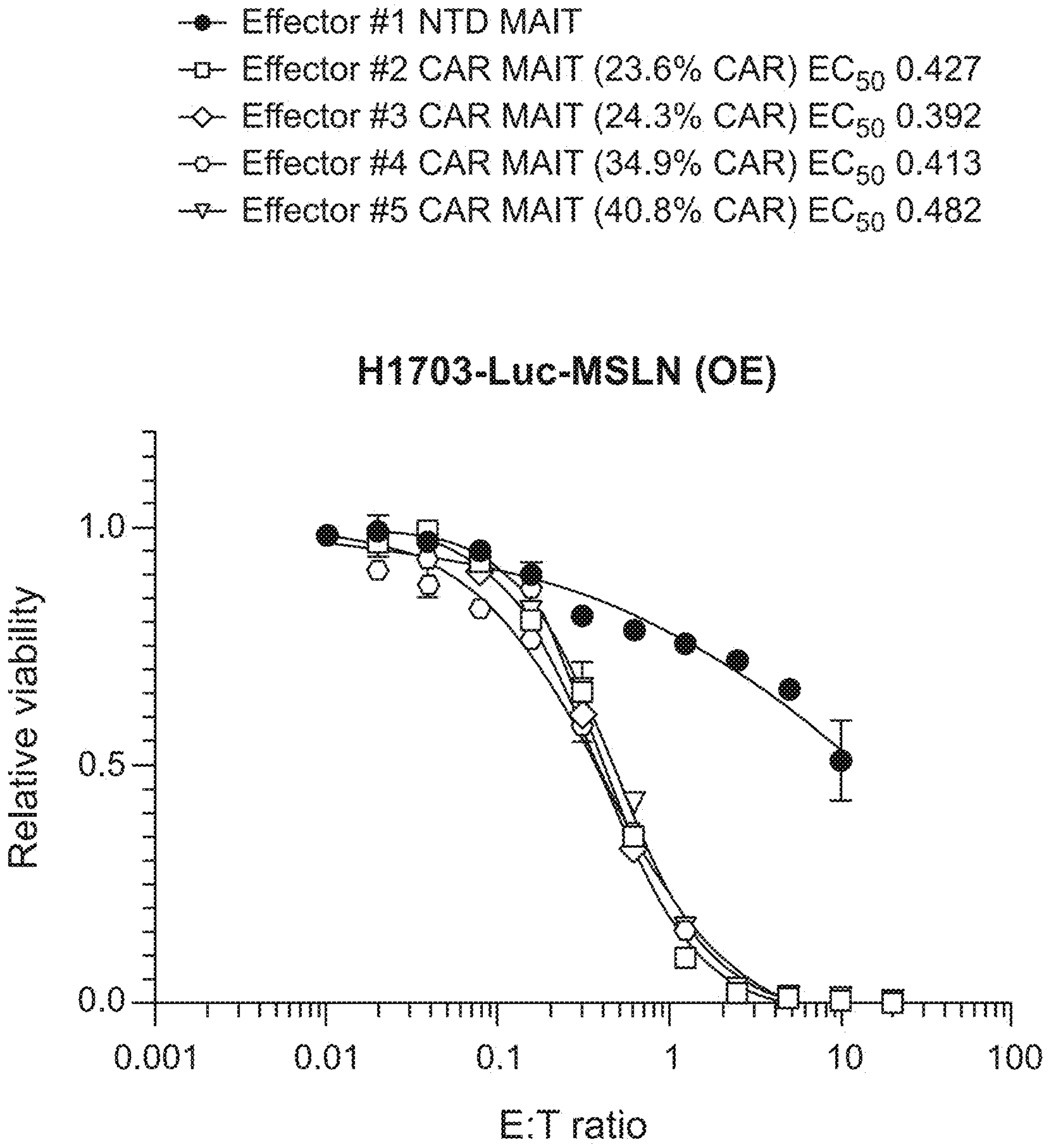

In order to evaluate the basal potential of MAIT cells originating from IVB or PB, the collected cells were stimulated with PMA and Ionomycin and stained for intracellular Granzyme B secretion. As shown, stimulated IVB MAIT cells produce significantly higher levels of Granzyme B compared to PB MAIT cells indicating on an increased effector and lytic capacity of the cells originated from IVB. Statistical analysis was done using GP Prism, t-test comparison. $*p<0.05$, $p<0.01$, $*p<0.001$ FIG. 13 is a graphic illustration of functional killing characteristics of placental IVB CAR-MAIT cells in accordance with examples of the invention.

CAR-MAIT cells were produced according to the standard protocol described in the Methods and co-cultured with NSCLC targets over expressing MSLN and Luciferase. Killing was measured by luminescence readout. The different effectors have different levels of $CAR^+$ fraction. Co-culture with target cells was at a range of effector:target (E:T) ratio determined by the $CAR^+$ fraction. All different culture conditions of CAR-MAIT cells resulted in similar efficacy against the target cells, indicating on high and dose dependent efficacy of the CAR-MAIT cells.

Figure 14A:
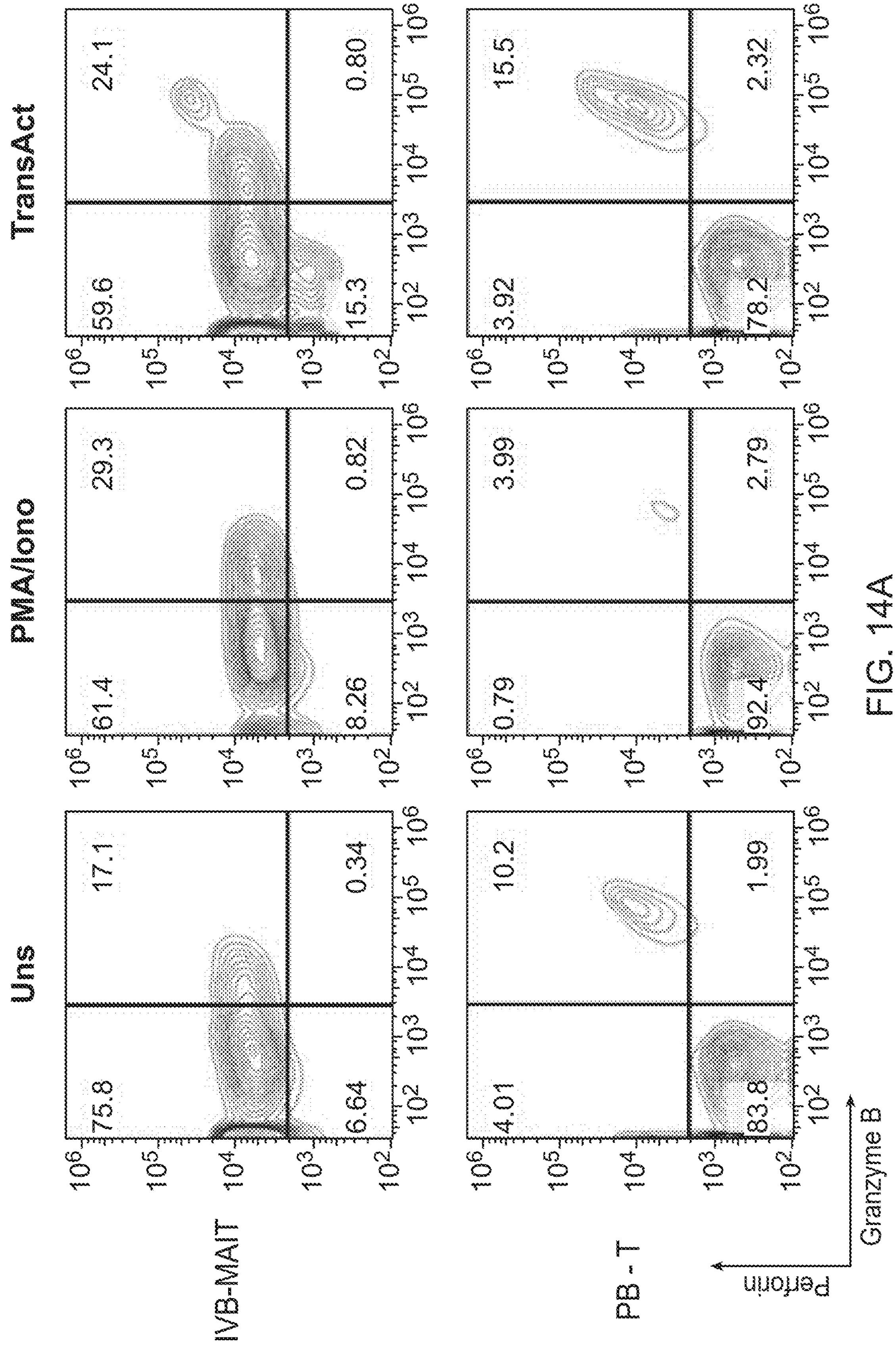
Figure 14B:
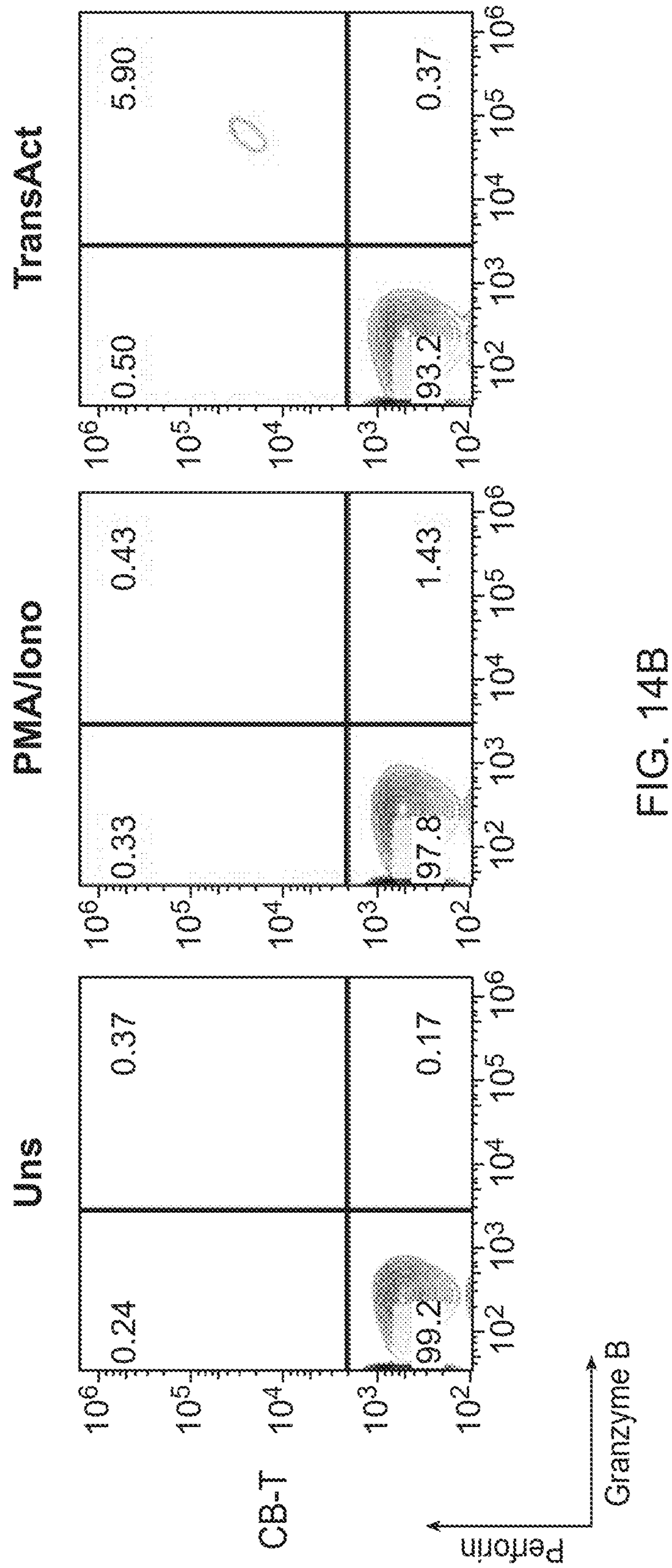
Figure 14C:
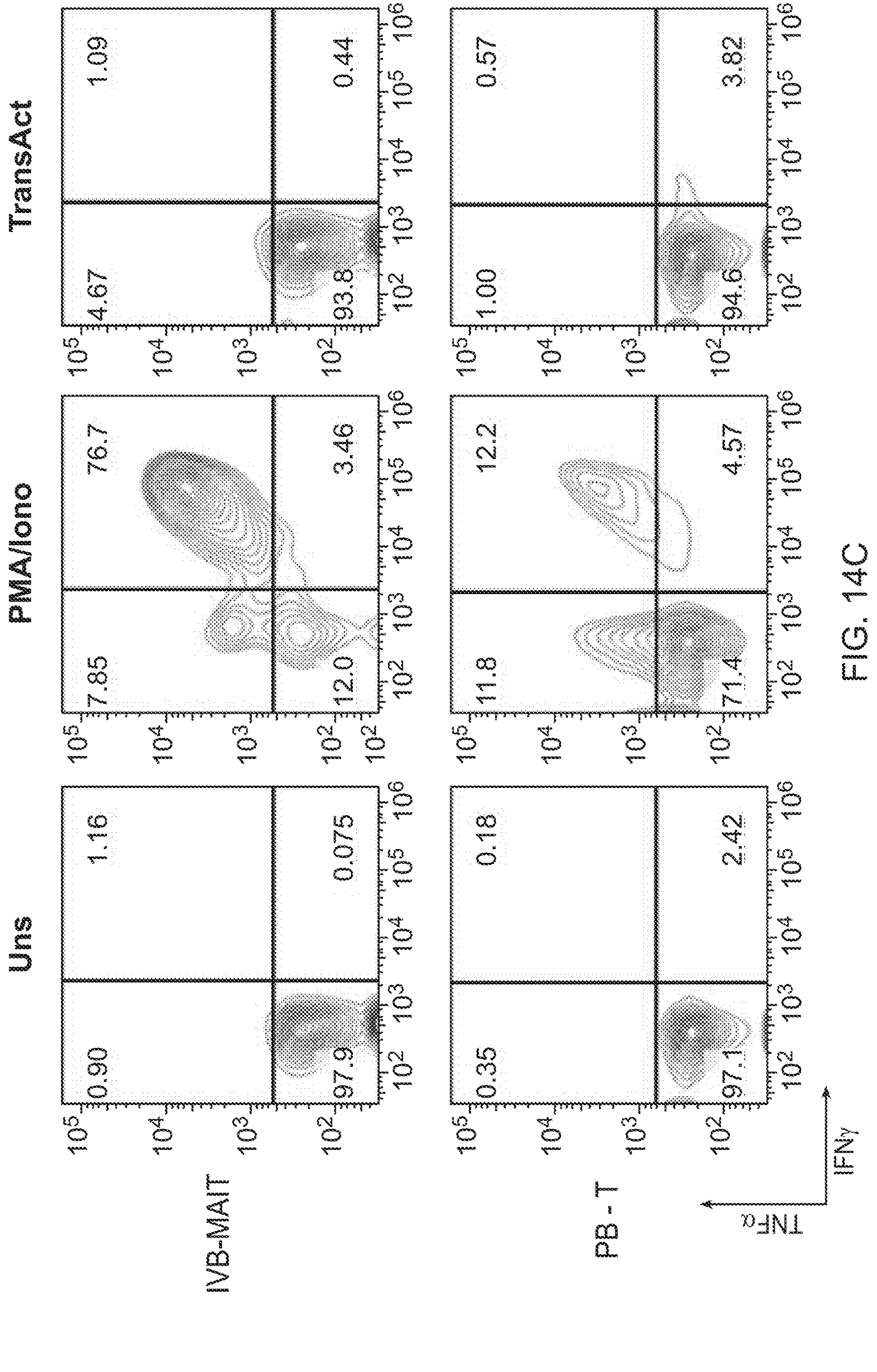
Figure 14D:
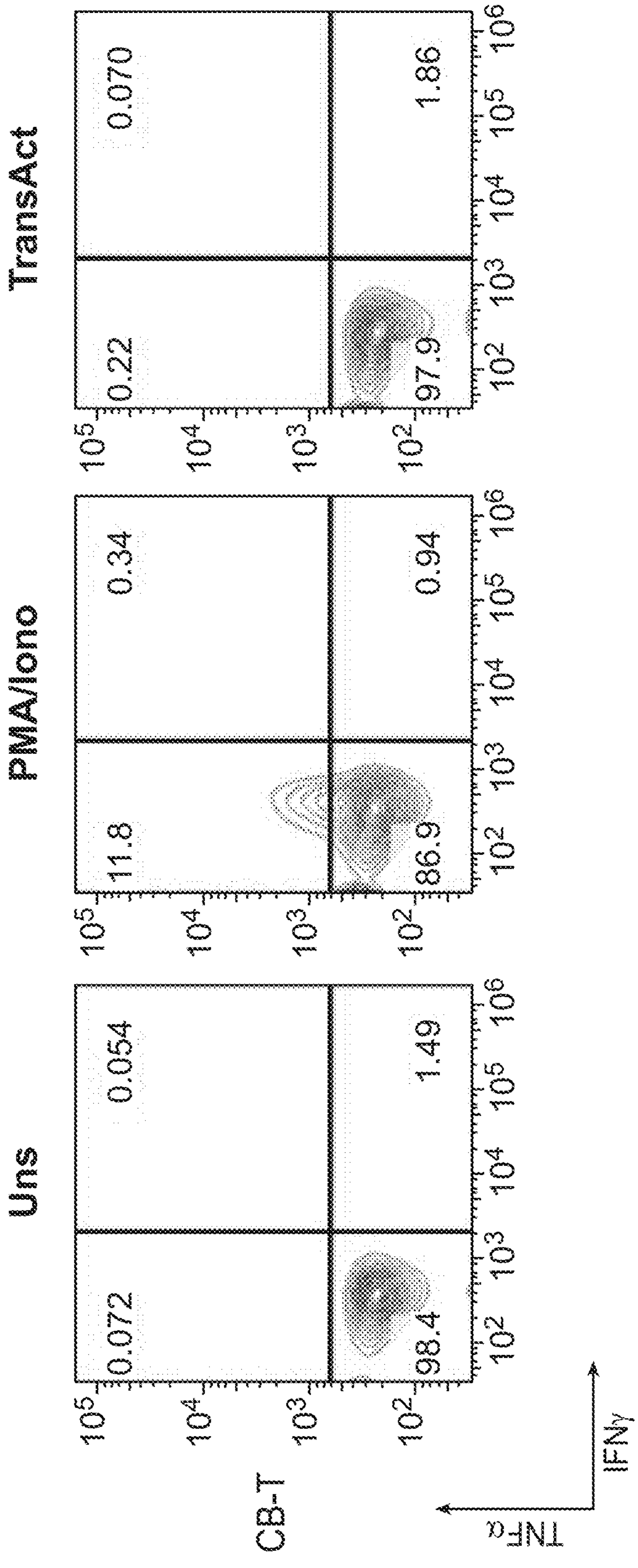
Figure 15A:
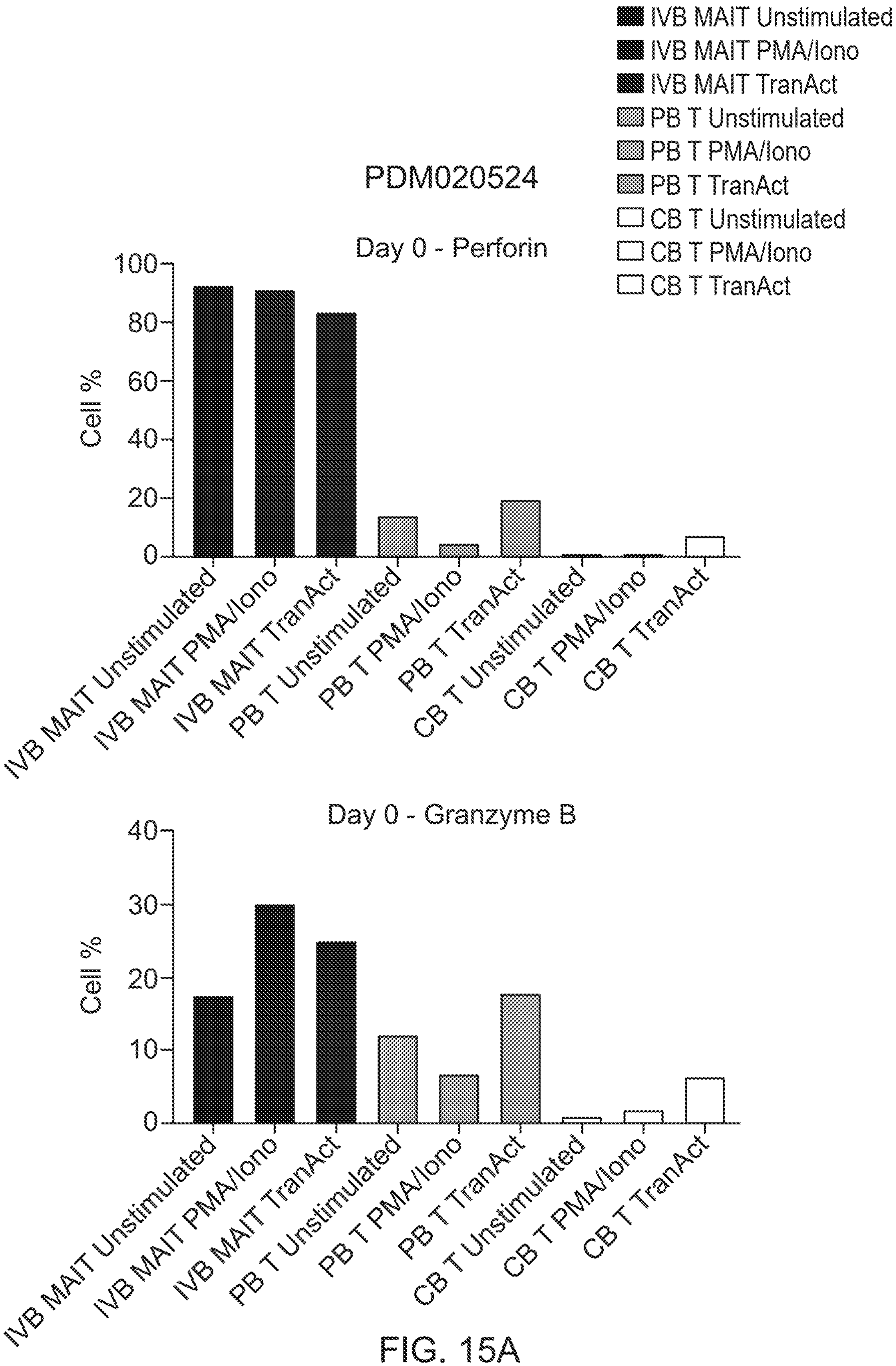
Figure 15B:
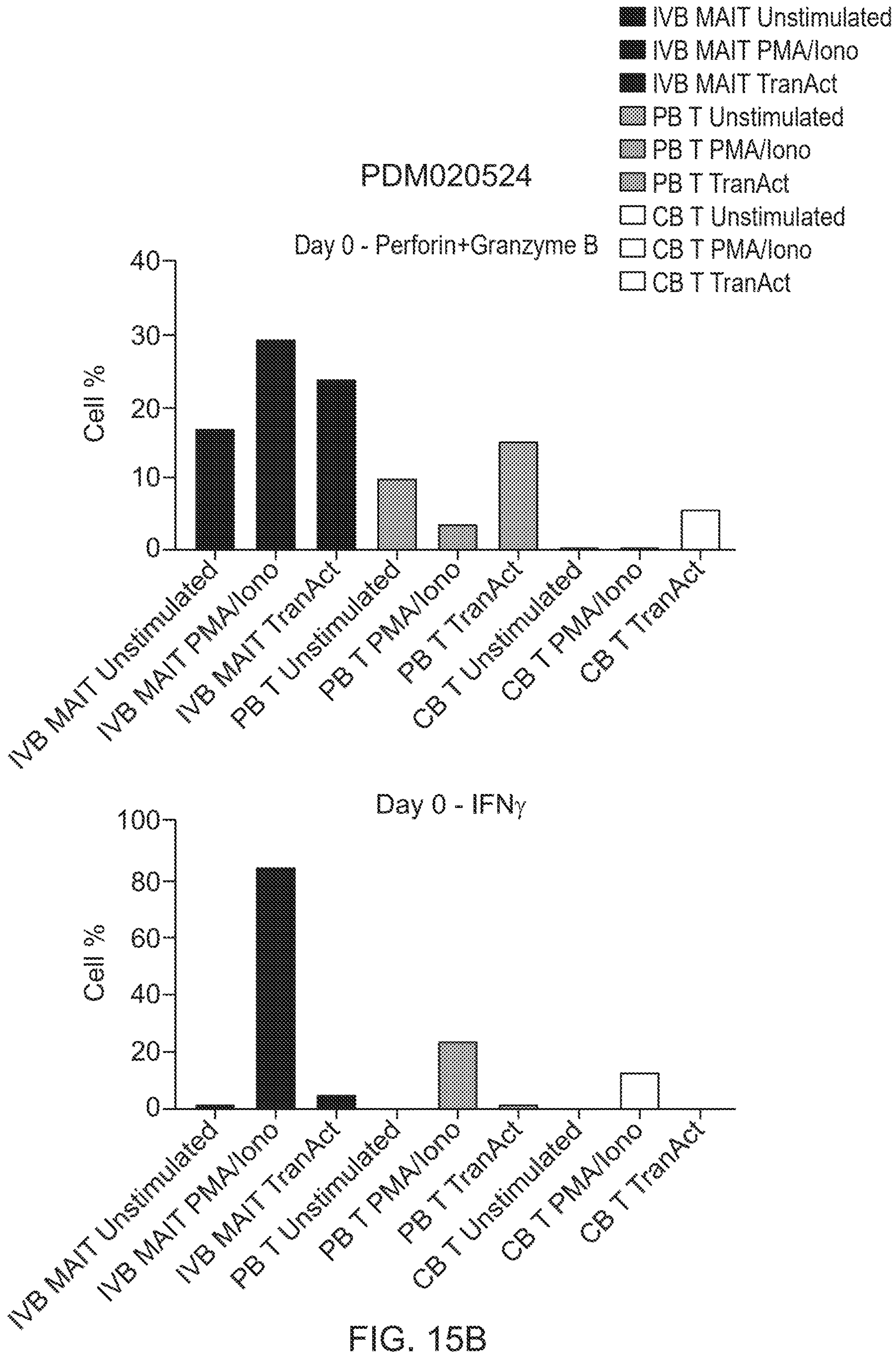
Figure 15C:
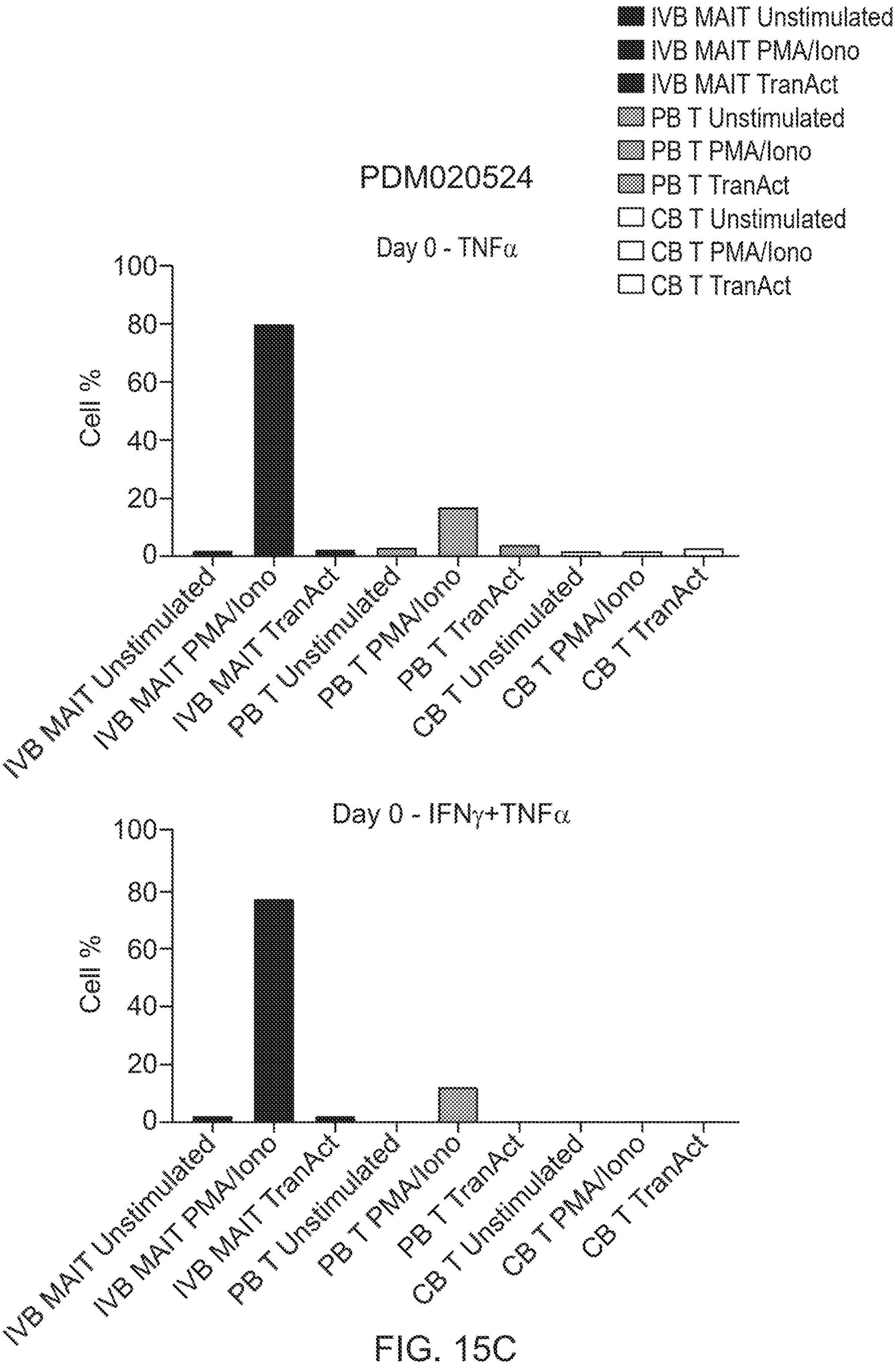
Figure 15D:
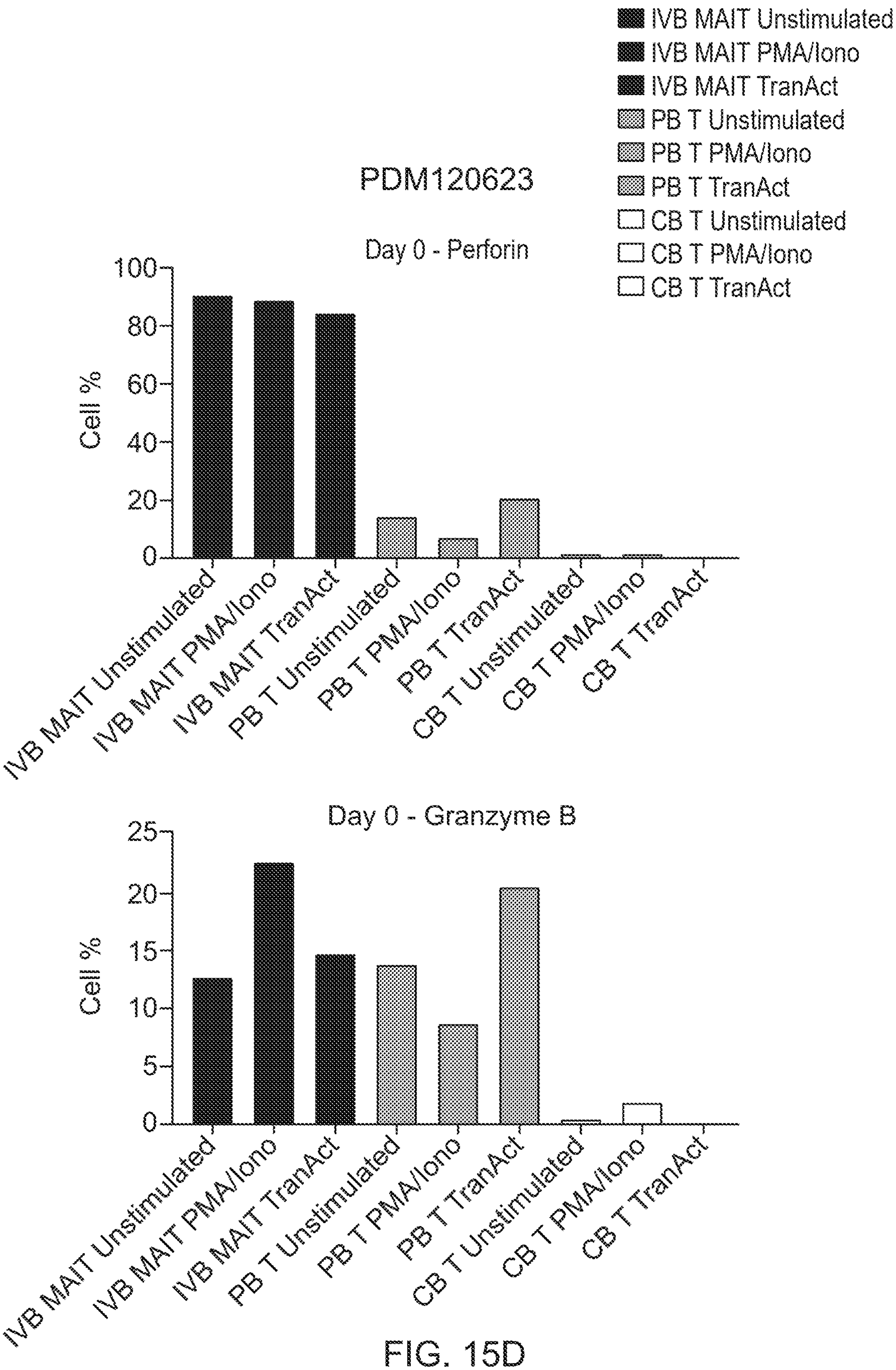
Figure 15E:
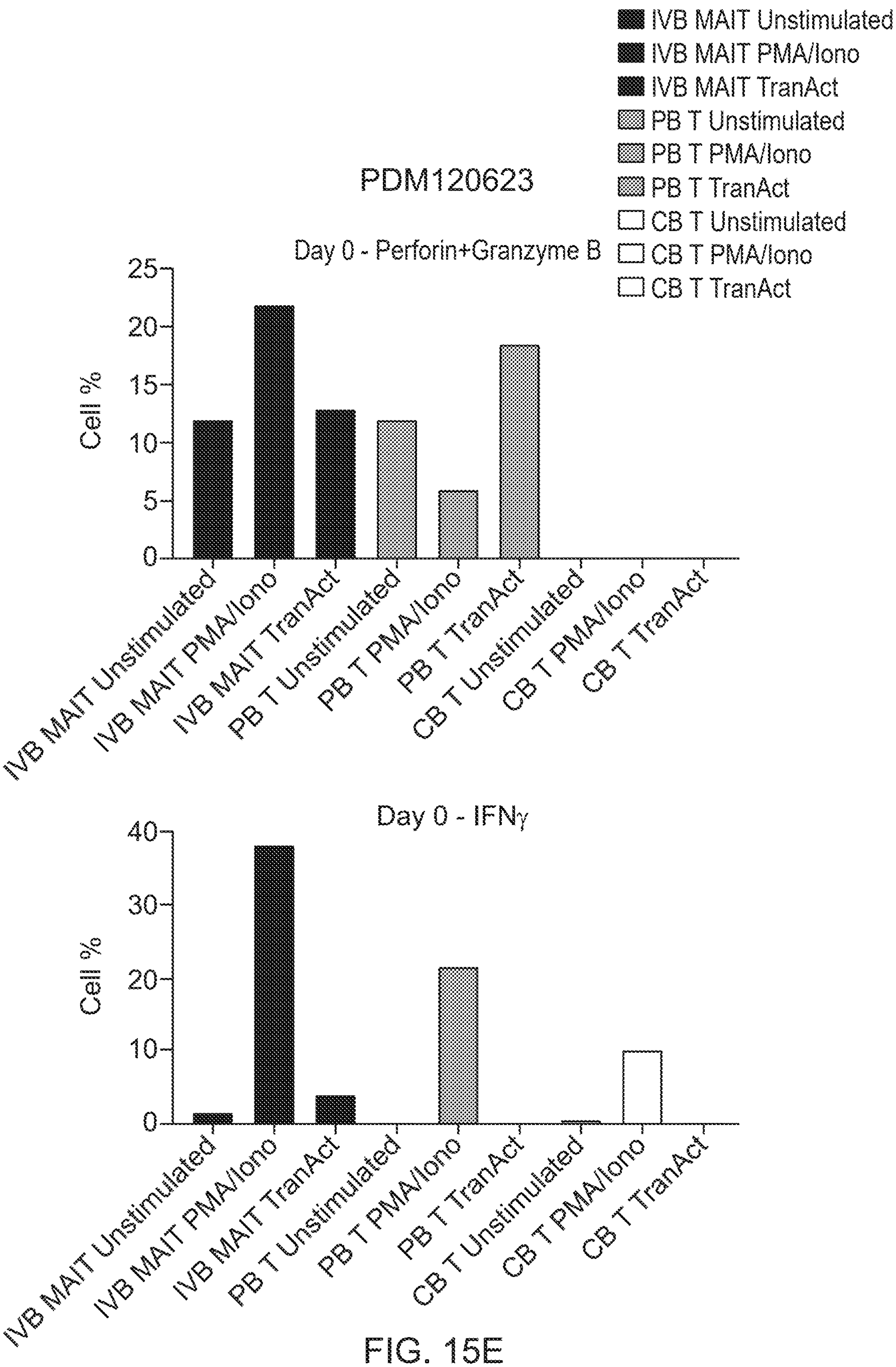
Figure 15F:
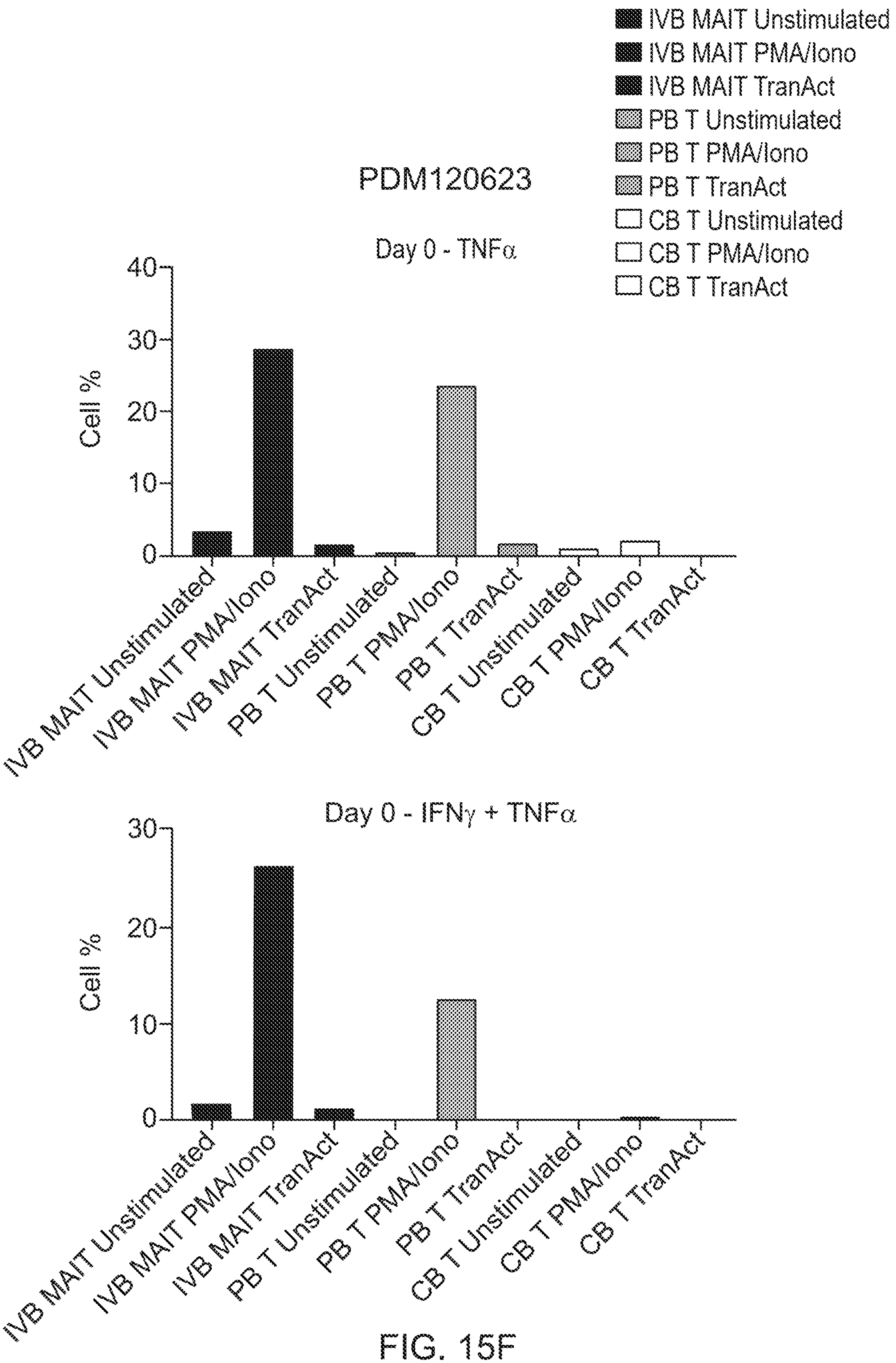

FIGS. 14A-14D show comparison between IVB MAIT cells, peripheral blood (PB) mother T cells, and cord blood (CB) T cells from the same donor (matched blood). To evaluate differences between MAIT cells and T cells and to eliminate donor to donor variability the inventors evaluated functional differences of the different cells originating from the same donor. IVB, PBMCs and CB were collected as described in the methods, and on day zero (0) were activated with T cell activators. Following intra cellular staining protocol, the cells were analyzed for Perforin, Granzyme B, IFN-γ and TNF-α using flow cytometry. FIG. 14A describes the gating strategy of analysis. FIG. 14B is a flow cytometric plot describing the raw data for Perforin and Granzyme B; FIGS. 14C-14D is are a flow cytometric plot describing the raw data for IFN-γ and TNF-α.

As shown, MAIT cells on day 0 possess completely different effector molecules compared to conventional T cells. T cells originating from Cord blood and Peripheral blood have similar characteristics.

FIGS. 15A-15F illustrate a comparison of positive MAIT population originating from IVB, and conventional T cell population originating from peripheral mother blood (MB) and CB cultured using T cell standard activation protocol, according to the gating strategy illustrated in FIGS. 14A-14D. The example is of two donors respectively, from each donor IVB, peripheral mother blood (MB) and cord blood (CB) were obtained.

To evaluate differences between MAIT and T cells and to eliminate donor variability, on day zero (0) IVB, PBMCs and CB were collected as described in the methods and were activated and cultured with T cell activators according to standard protocol. Briefly, T cell expansion is used by activation of the TCR with CD28 and CD3 antibodies or beads (TransAct) with IL2 cytokine. On day ten (10) cells were stained for CD161 and TCR Vα7.2 to evaluate the fraction of MAIT positive population. As observed, only upon following specific MAIT expansion protocol the end population is highly purified as high as >95% MAIT cells out of $CD3^+$ cells. By applying standard T cell expansion protocol the initially detected (pre-expansion, day 0) MAIT cells do not expand, and the detected MAIT population on day 10 is dramatically diluted to as low as <1.2% out of $CD3^+$ cells.

Figure 16A:
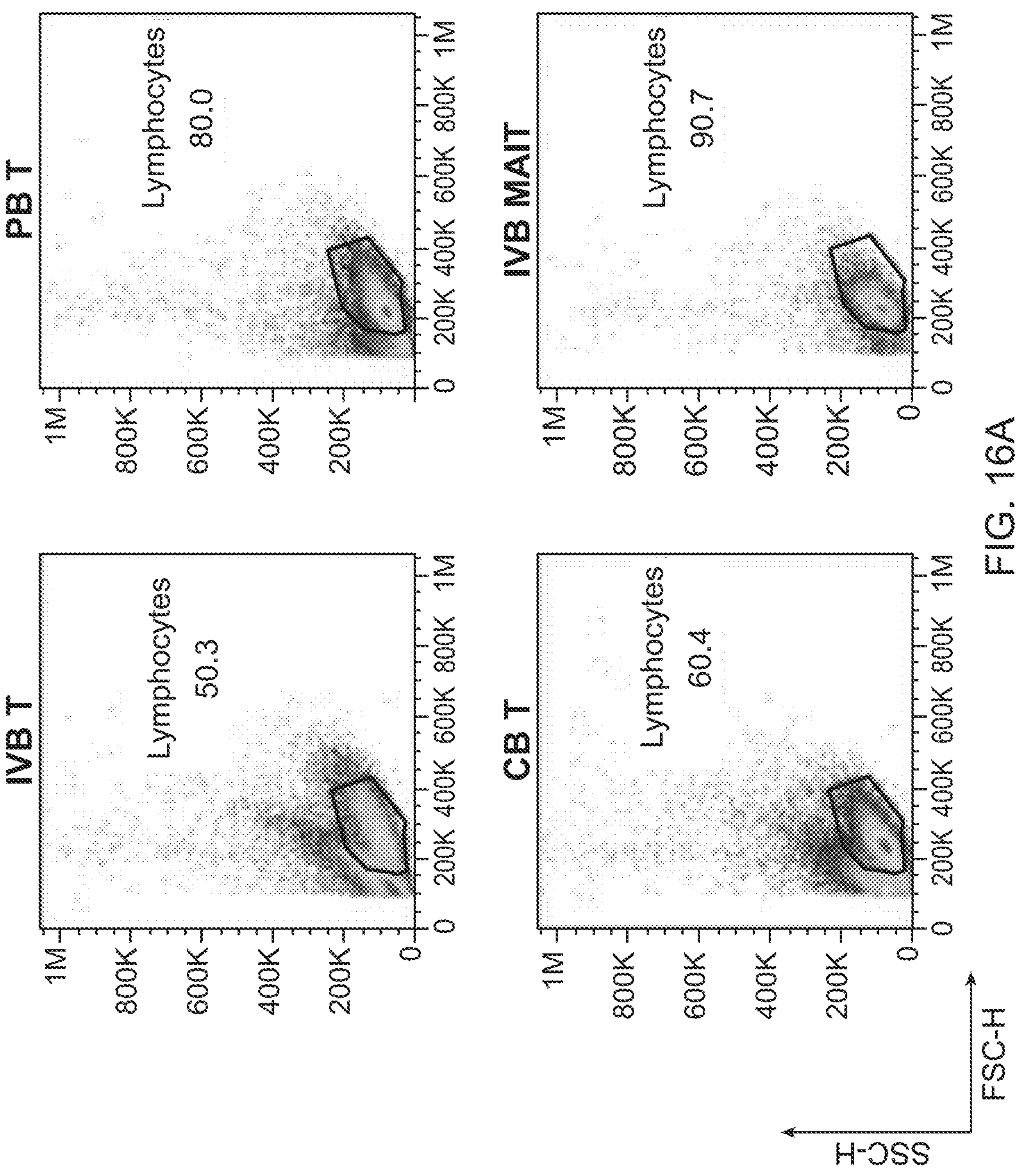
Figure 16B:
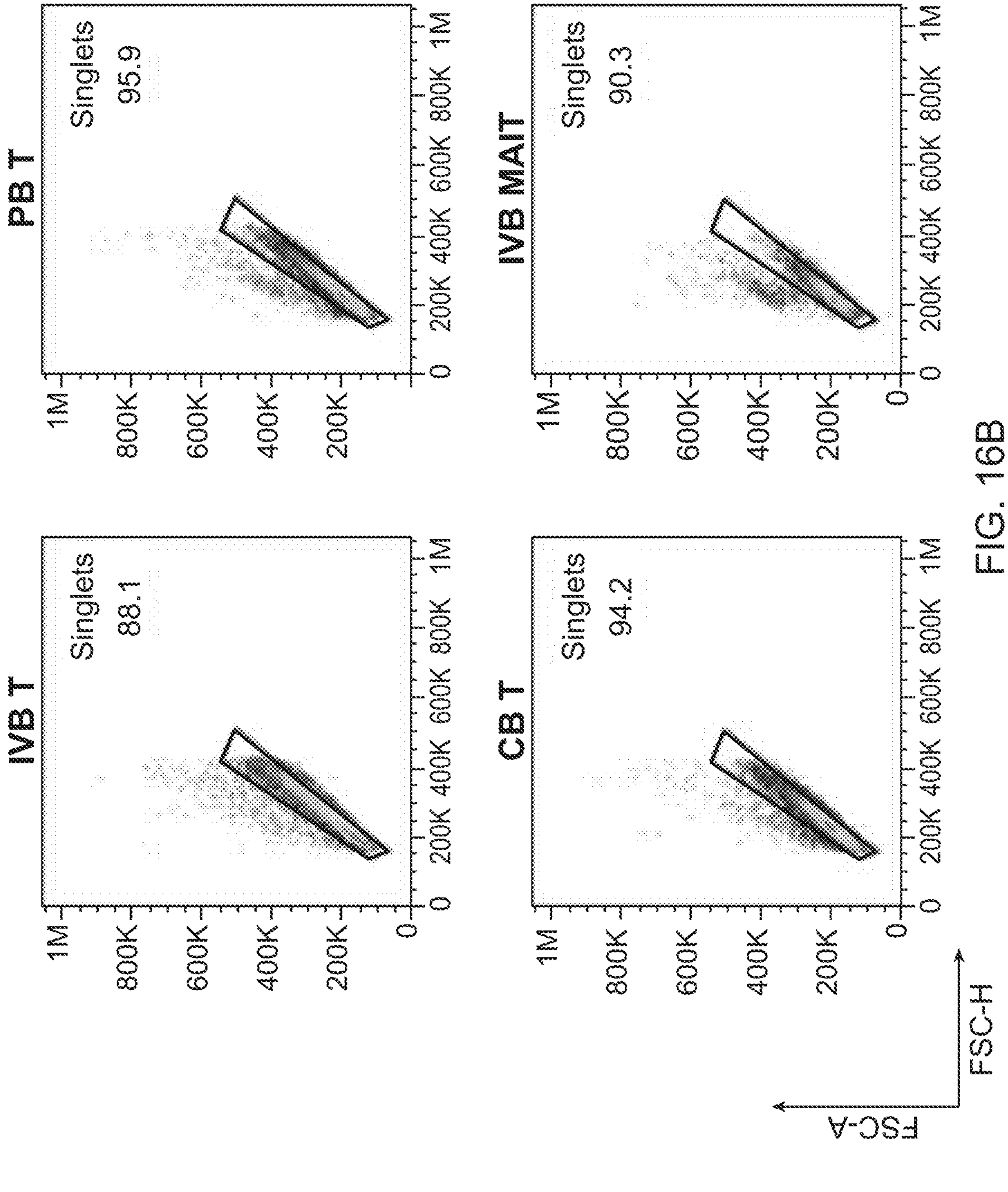
Figure 16C:
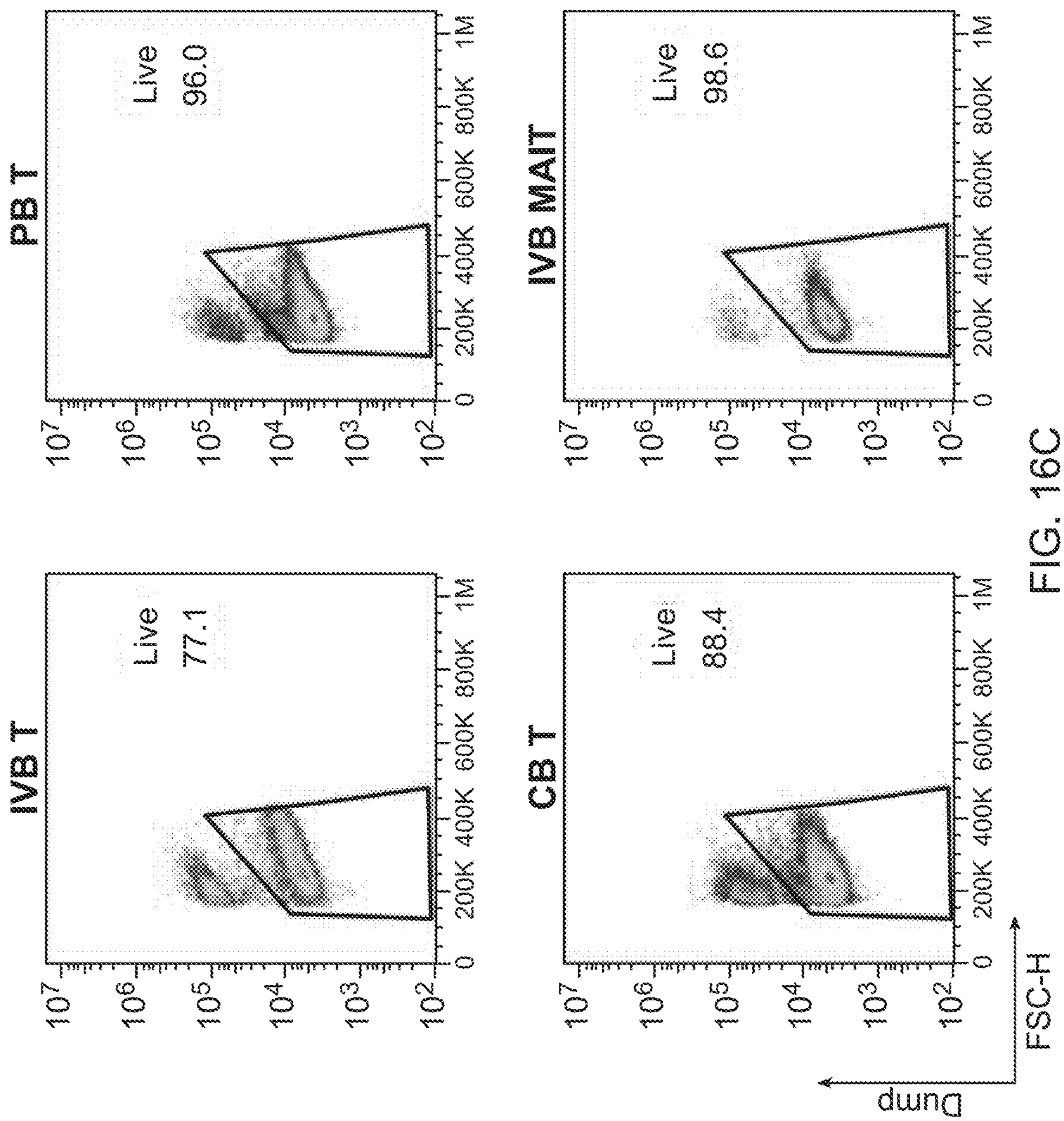
Figure 16D:
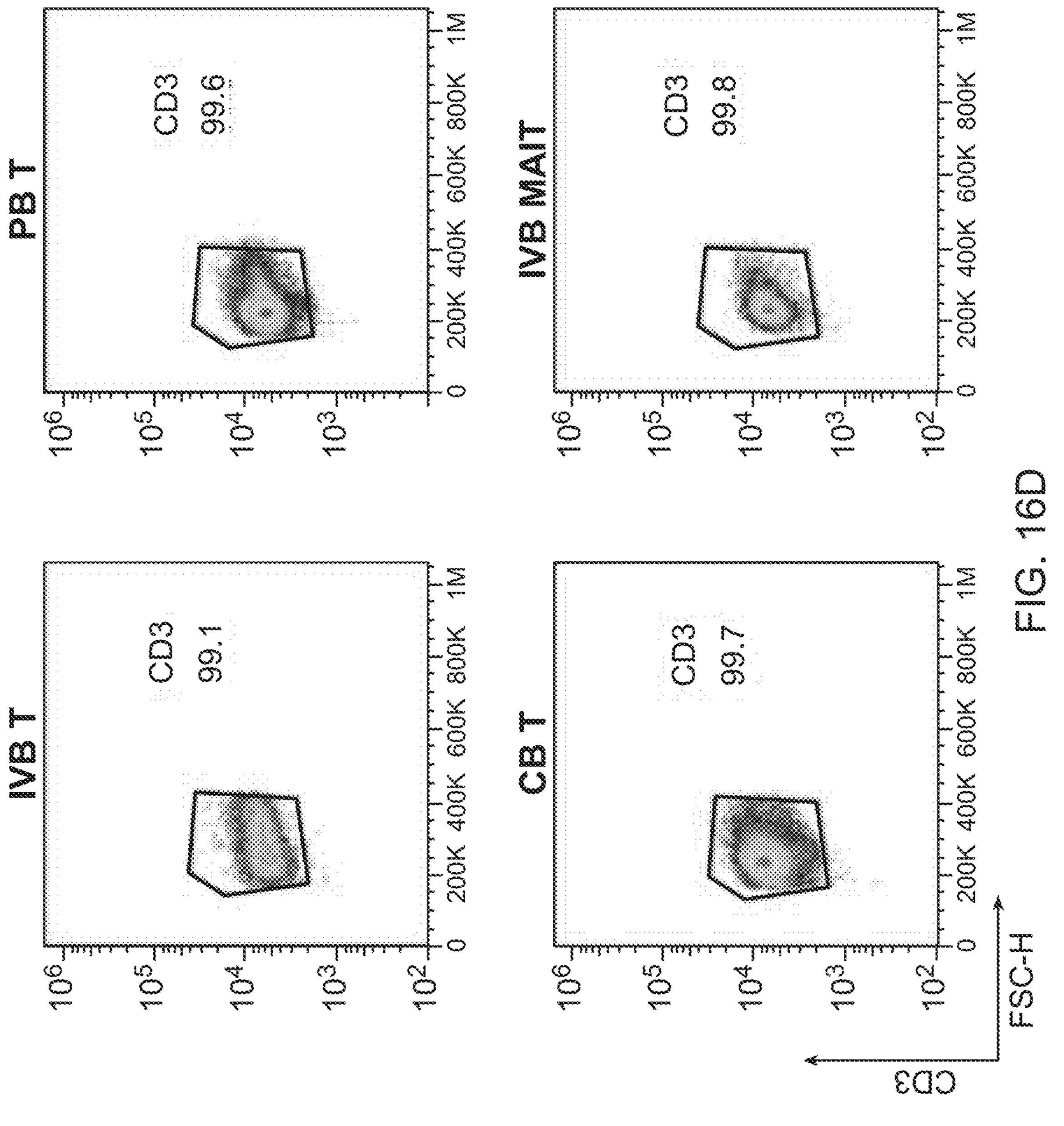
Figure 16E:
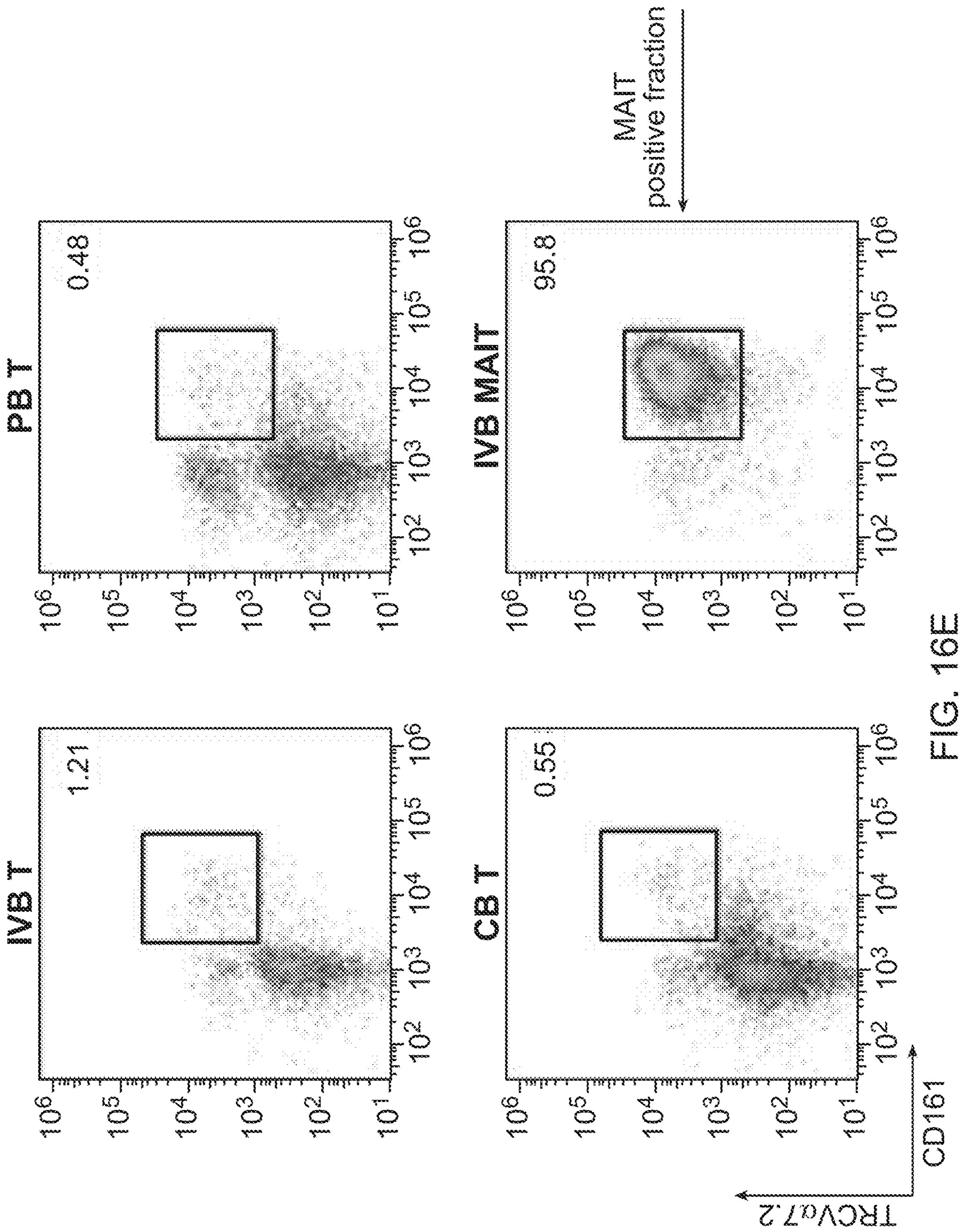
Figure 16F:
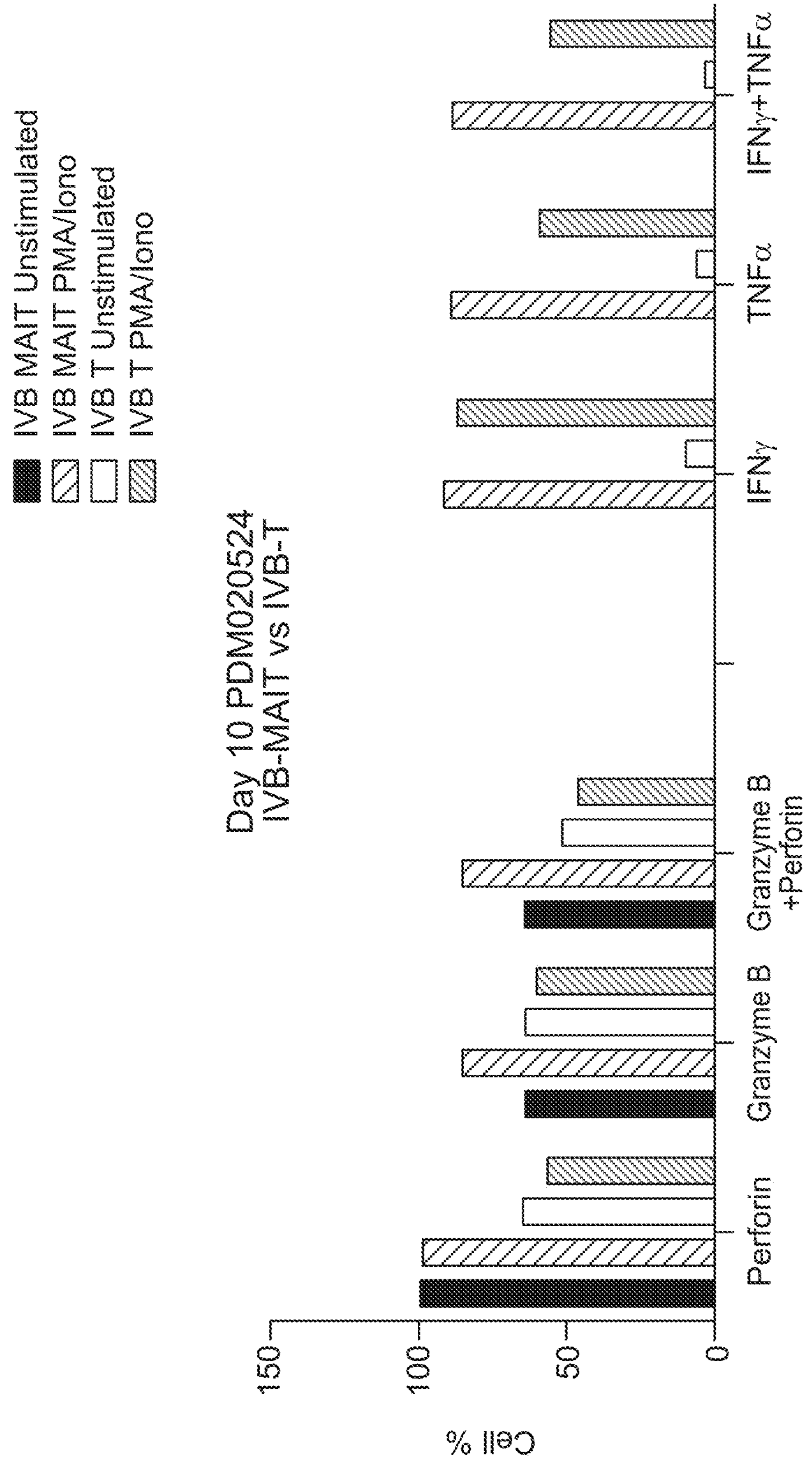

FIGS. 16A-16F are graphic illustrations describing comparison of IVB-MAIT and IVB-T effector function in accordance with examples of the invention. FIG. 16A-16E are graphic illustrations describing comparison of IVB-MAIT and IVB-T effector function. IVB-MAIT were cultured as described in the methods. From the same raw material (IVB cell harvesting) the inventors also cultured T cells using standard conventional T cells protocol with TransAct and IL2. On day ten (10), IVB-MAIT cells and IVB-T cells were stimulated using PMA+Ionomycin or TransAct, stained for effector molecules e.g. IFN-g, TNF-α, Perforin and Granzyme B and analyzed by flow cytometry. FIG. 16F shows that MAIT cells have higher levels of Perforin and TNF-α compared to T cells originating from the same source.

Figures 17A, 17B, 17C:
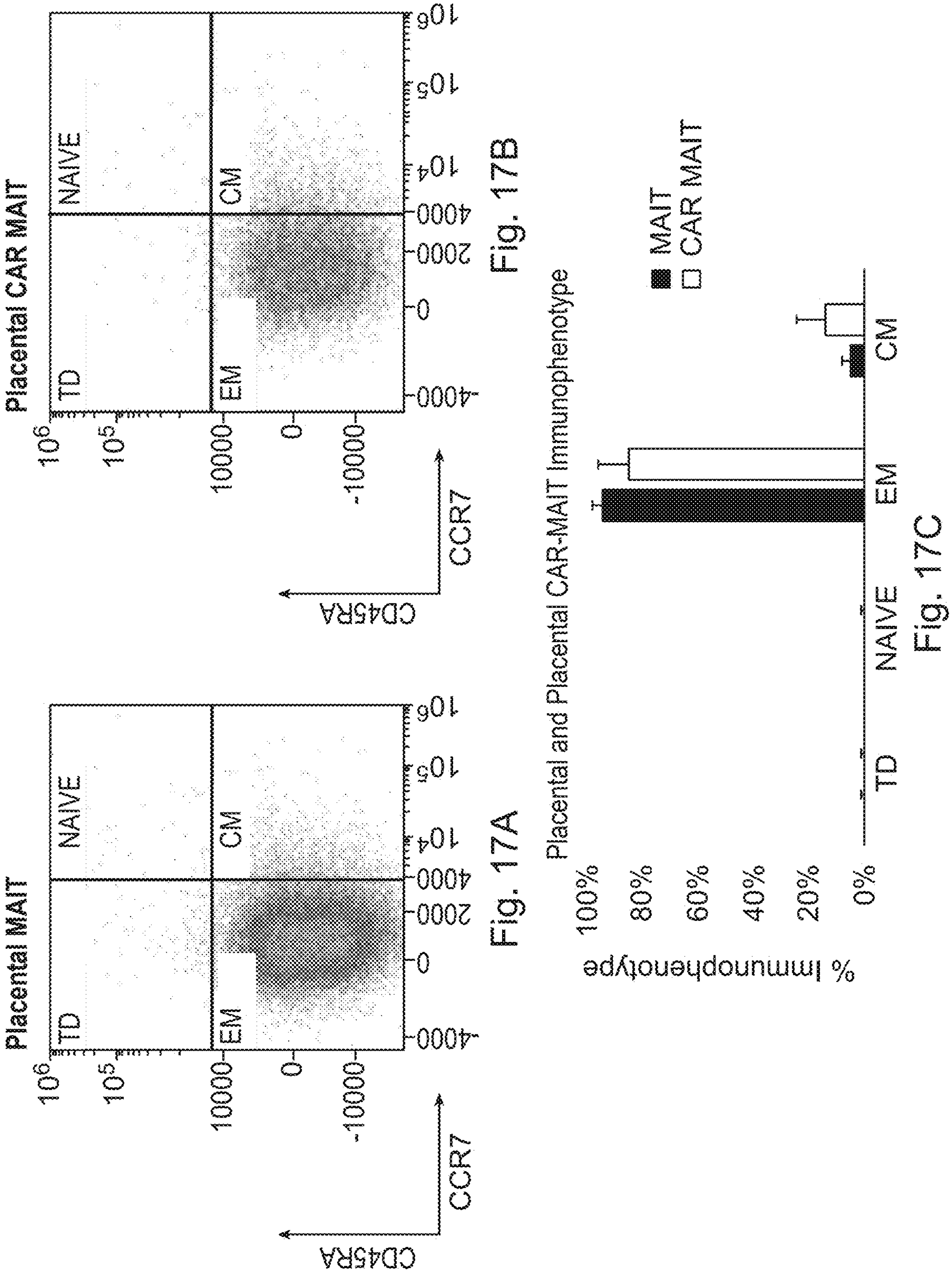

FIGS. 17A-17B are flow cytometry plots of placental MAIT cells and placental CAR-MAIT cells respectively for Immunophenotype comparison of the cell's populations. Cells were expanded for 10 days, stained according to standard cell surface marker protocol, and analyzed via flow cytometry. The gating strategy of CD45RA vs. CCR7 showed a statistically significant increase in "effector memory (EM)" compared to "central memory (CM)" cells. Naïve and terminally differentiated (TD) cells were nearly absent.

FIG. 17C is a graphical illustration of the results representing an average of 3 different donors analyzed on day 10. Results show that over 80% of both MAIT and CAR-MAIT cells were effector memory, while the remaining cells were central memory. Naïve and terminally differentiated cells were less than 1%.

DETAILED DESCRIPTION

Unless otherwise defined, all technical and/or scientific terms used herein have the same meaning as commonly understood by one of ordinary skill in the art to which the engineered mucosal-associated invariant T (MAIT) cells and methods of use thereof pertains. Although methods and materials similar or equivalent to those described herein can be used in the practice or testing of embodiments of the engineered mucosal-associated invariant T (MAIT) cells and methods of use thereof, exemplary methods and/or materials are described below. In case of conflict, the patent specification, including definitions, will control. In addition, the materials, methods, and examples are illustrative only and are not intended to be necessarily limiting. Each literature reference or other citation referred to herein is incorporated herein by reference in its entirety.

The terms "comprise", "comprises", "comprising", "includes", "including", "having" and their conjugates mean "including but not limited to".

As used herein, the singular form "a", "an" and "the" include plural references unless the context clearly dictates otherwise. For example, the term "an enzyme" or "at least one enzyme" may include a plurality of enzymes, including mixtures thereof.

Except where indicated otherwise, the term "population", when used in conjunction with a particular cell attribute or attributes, may encompass a collection of cells, at least 70% of which exhibit the mentioned attribute or attributes. In other embodiments, at least 80%, at least 85%, at least 90%, at least 92%, at least 95%, at least 96%, at least 97%, at least 98%, or at least 99% of the cells in the collection exhibit the mentioned attribute or attributes. In some embodiments, the population is isolated from a cell type distinct from a particular attribute. In some embodiments, a population of placental engineered MAIT cells described herein comprises exogenous attributes.

With reference to placenta-derived cells except, where indicated otherwise, "placenta", "placental", and the like, encompass intervillous blood (IVB) Placenta-derived MAIT cells are obtained from maternal sources of the placenta. In some embodiments, MAIT cells are obtained from intervillous blood of the placenta. In some embodiments, MAIT cells are obtained from decidua parietalis of the placenta. In some embodiments, MAIT cells are obtained from decidua basalis of the placenta. In some embodiments, MAIT cells are not obtained from cord blood.

As used herein, the terms "peripheral blood derived MAIT cells", "peripheral blood MAIT cells", or "peripheral MAIT cells" comprise MAIT cells isolated from peripheral blood (PB). In some embodiments the peripheral blood is obtained from a different donor. In some other embodiments the peripheral blood is matched to the intervillous blood and/or to the cord blood and received from the mother. These terms may be used interchangeably, having all the same qualities and meanings.

As used herein, the terms "intervillous blood (IVB)-derived MAIT cells" or "IVB MAIT cells", "placental intervillous blood MAIT", "placental IVB MAIT" and "placental MAIT" as used herein are all meaning the same and refer to MAIT cells isolated from intervillous blood of placenta, and/or blood obtained from the maternal portion of the placenta.

As used herein, "MAIT cells" would broadly encompass MAIT cells from any source including but is not limited to peripheral blood, cord blood and intervillous blood.

In some embodiments of populations of engineered MAIT cells, the MAIT cells are derived from maternal blood source of the placenta. In some embodiments of populations of engineered MAIT cells, the MAIT cells are derived from maternal blood sources of the placenta. In some embodiments of populations of engineered MAIT cells, the MAIT cells are obtained from intervillous blood of the placenta. In some embodiments of populations of engineered MAIT cells, the MAIT cells are not obtained from cord blood.

Placental cells may be obtained, in various embodiments, from a full-term placenta. A convenient source of placental tissue is a post-partum placenta (e.g., less than 48 hours after birth); however, a variety of sources of placental tissue or cells may be contemplated by the skilled person. In other embodiments, the placenta is used within 24 hours (in some embodiments, while preserved in physiological buffer), 18 hours, 14 hours, 10 hours, 8 hours, within 6 hours, within 5 hours, within 4 hours, within 3 hours, within 2 hours, or within 1 hour of birth. In certain embodiments, the placenta is kept chilled prior to harvest of the cells. In other embodiments, prepartum placental tissue is used. In some embodiments, the donor is 40 years old or younger, in other embodiments 35 years old or younger, while in other embodiments, the donor may be any woman of childbearing age.

Methods for isolating MAIT cells from placental intervillous blood (IVB) are generally known in the art. An exemplary, non-limiting protocol utilizes blood that drips from a placenta lifted with the clamped umbilical cord facing down. Such methods were shown to have a very low rate of cross-contamination between IVB and umbilical cord blood. Those skilled in the art are familiar with methods of checking purity of cell populations and, if necessary, enhancing the purity, using cell sorting and the like.

Mucosal-Associated Invariant T (MAIT) Cells

Mucosal associated invariant T (MAIT) cells, as used herein, comprise non conventional T cells that express a semi-invariant TCR, e.g., V□7.2-J□33 in humans; in some embodiments associated with the β-chains Vβ2/Vβ13. In other embodiments, the aforementioned alpha chain is associated with a beta chain from the TRBV6 or TRBV20 gene families. In some embodiments, the MAIT cells recognize antigen restricted to non-peptide molecules presented in the context of (non-polymorphic) major histocompatibility complex (MHC) class I-like protein MR1. In some embodiments, the engineered MAIT cells disclosed herein are detectable by staining with MR1-Ag tetramer, e.g., loaded with 5-(2-oxopropylideneamino)-6-D-ribitylaminouracil (5-OP-RU); 5-(2-oxoethylideneamino)-6-D-ribitylaminouracil (5-OE-RU); RL-6,7-diMe (PubChem CID 168989); RL-6-Me-7-OH (PubChem CID 440869), or diclofenac (PubChem CID 3033). In other embodiments, one of the following compounds may also be used: 6-(1H-indol-3-yl)-7-hydroxy-8-ribityllumazine or photolumazine III (PLIII); 6-(2-carboxyethyl)-7-hydroxy-8-ribityllumazine or photolumazine I; 5-Hydroxydiclofenac (PubChem CID 3052566); 4-Hydroxydiclofenac (PubChem CID 116545); benzbromarone (PubChem CID 2333); chloroxine (PubChem CID 2722); floxuridine (PubChem CID 5790); galangin (4H-1-benzopyran-4-one,3,5,7-trihydroxy-2-phenyl or 3,5,7-trihydroxyflavone); or mercaptopurine (PubChem CID 667490) (see, e.g., Corbett et al., Antigen Recognition by MR1-Reactive T Cells; MAIT Cells, Metabolites, and Remaining Mysteries. *Front Immunol.* 11:1961 (2020), and the references cited therein).

In certain embodiments, the placental MAIT cells disclosed herein are human MAIT cells. In some embodiments, the MAIT cells disclosed herein are allogeneic with respect to the recipient of a population of the engineered MAIT cells, as described herein.

Methods for isolating and characterizing placental IVB MAIT cells and other leukocyte sub-populations are known in the art. Solely for exemplification, leukocyte sub-populations can be isolated and/or analyzed using the gating strategy as described herein.

There are quantitative and qualitative differences between cord blood and adult blood-derived MAIT cells (see e.g., Youssef et al., Ontogeny of Human Mucosal-Associated Invariant T Cells and Related T Cell Subsets. JEM 215:459-479 (2018)). Vα7.2 and CD161 staining allows identification of circulating stage 3 MAIT cells at birth. However, the Vα7.2+ CD161$^{high}$ fraction in cord blood may also encompass other T cells probably sharing a common developmental pathway. In cord blood, MAIT cells express naïve phenotype (CD45RA$^{+}$/RO$^{-}$) and express the CD8αβ heterodimer, whereas they mostly exhibit memory phenotype and express the CD8αα homodimer in adults. The very low expansion of Vα7.2$^{+}$ CD161$^{high}$ T cells after birth may be related to cell intrinsic characteristics or to limited availability of microbial-derived MR1-ligands. Naïve cord blood Vα7.2$^{+}$ CD161$^{high}$ T cells expressed significantly lower levels of PLZF than adult MAIT cells, suggesting that final maturation of cord blood Vα7.2$^{+}$ CD161$^{high}$ T cells requires an early activation signal after birth. Cord blood Vα7.2+ CD161$^{high}$ T cells strongly proliferate after stimulation by PHA, similar to conventional CD8 T cells, whereas adult Vα7.2+ CD161$^{high}$ T cells proliferate much less efficiently. In contrast to mature MAIT cells in adult blood, cord blood Vα7.2$^{+}$ CD161$^{high}$ T cells are not able to display immediate effector functions toward bacterially infected cells. This data indicate that, although they have intrinsic ability to proliferate, cord blood Vα7.2$^{+}$ CD161$^{high}$ T cells need functional maturation and/or expansion after birth to acquire detectable effector activities after microbe-derived antigen recognition.

Since cord blood Vα7.2$^{+}$ CD161$^{high}$ cells exhibit a naïve phenotype and intermediate PLZF levels, they are unable to rapidly produce cytokines or cytotoxic molecules in response to bacterial ligands, in contrast to mature adult MAIT cells. Neither do cord blood MAIT cells respond to stimulation by exogenous IL-12 and IL-18, despite high expression of the receptors for these cytokines. As further shown in Chen et al., Circulating Mucosal-Associated Invariant T Cells in a Large Cohort of Healthy Chinese Individuals From Newborn to Elderly. Front. Immunol., vol. 10, article 260 (2019), cord blood MAIT cells have naïve phenotype and do not secrete IFN-□, IL17A, and TNF-□ following in vitro stimulation with PMA/Ionomycin. Taken together, these data indicate that cord blood MAIT cells are phenotypically and functionally different from MAIT cells derived from adult subjects.

In some embodiments, MAIT cells disclosed herein comprise CD161$^{+}$Vα7.2$^{+}$, CD4$^{-}$CD3$^{+}$ lymphocytes, which, in further embodiments, also bind to MR1-Ag tetramer. In various embodiments, at least 50% of the cells in the population are CD161$^{+}$Vα7.2$^{+}$, CD4$^{-}$CD3$^{+}$. In some embodiments, at least 60%, at least 70%, at least 80%, at least 85%, at least 90%, at least 95%, at least 97%, at least 98%, or at least 99% of the cells in the population are CD161$^{+}$Vα7.2$^{+}$, CD4$^{-}$CD3$^{+}$.

In yet some embodiments, MAIT subsets are utilized, including but not limited to CD8$^{+}$ cells (more specific embodiments of which are CD8$^{+}$CD4$^{-}$ cells), CD8$^{-}$CD4$^{-}$ cells, or CD4$^{+}$ cells. In various embodiments, at least 50% of the cells in the population are CD8$^{+}$. In other embodiments, at least 60%, at least 70%, at least 80%, at least 85%, at least 90%, at least 95%, at least 97%, at least 98%, or at least 99% of the cells in the population are CD8$^{+}$. In various embodiments, at least 50% of the cells in the population are CD8$^{+}$CD4$^{-}$. In other embodiments, at least 60%, at least 70%, at least 80%, at least 85%, at least 90%, at least 95%, at least 97%, at least 98%, or at least 99% of the cells in the population are CD8$^{+}$CD4$^{-}$. In various embodiments, at least 50% of the cells in the population are CD8$^{-}$CD4$^{-}$. In other embodiments, at least 60%, at least 70%, at least 80%, at least 85%, at least 90%, at least 95%, at least 97%, at least 98%, or at least 99% of the cells in the population are CD8 CD4.

In certain embodiments, the MAIT cells disclosed herein are CD45RA$^{-}$CCR7$^{-}$, also reflecting, in some embodiments, an effector memory phenotype. In other embodiments, CD45RO$^{+}$ is an additional characteristic of effector memory cells. In various embodiments, at least 50% of the cells in the population are CD45RA$^{-}$CCR7$^{-}$; in other embodiments, at least 60%, at least 70%, at least 80%, at least 85%, at least 90%, at least 95%, at least 97%, at least 98%, or at least 99% of the cells in the population are CD45RA$^{-}$CCR7$^{-}$. In various embodiments, at least 50% of the cells in the population are CD45RO$^{+}$; in other embodiments, at least 60%, at least 70%, at least 80%, at least 85%, at least 90%, at least 95%, at least 97%, at least 98%, or at least 99% of the cells in the population are CD45RO$^{+}$.

In certain embodiments, the MAIT cells disclosed herein are CD45RA$^{-}$CCR7$^{-}$CD62L$^{+}$. In various embodiments, at least 50% of the cells in the population are CD45RA$^{-}$CCR7$^{-}$CD62L$^{+}$; in other embodiments, at least 60%, at least 70%, at least 80%, at least 85%, at least 90%, at least 95%, at least 97%, at least 98%, or at least 99%.

In certain embodiments, the MAIT cells disclosed herein are $CD45RA^{-}CCR7^{-}CD62L^{-}$. In various embodiments, at least 50% of the cells in the population are $CD45RA^{-}CCR7^{-}CD62L^{-}$; in other embodiments, at least 60%, at least 70%, at least 80%, at least 85%, at least 90%, at least 95%, at least 97%, at least 98%, or at least 99%.

In certain embodiments, the MAIT cells disclosed herein are $CD45RO^{+}CCR7^{-}CD62L^{+}$. In various embodiments, at least 50% of the cells in the population are $CD45RO^{+}CCR7^{-}CD62L^{+}$; in other embodiments, at least 60%, at least 70%, at least 80%, at least 85%, at least 90%, at least 95%, at least 97%, at least 98%, or at least 99%.

In certain embodiments, the MAIT cells disclosed herein are $CD45RO^{+}CCR7^{-}CD62L^{-}$. In various embodiments, at least 50% of the cells in the population are $CD45RO^{+}CCR7^{-}CD62L^{-}$; in other embodiments, at least 60%, at least 70%, at least 80%, at least 85%, at least 90%, at least 95%, at least 97%, at least 98%, or at least 99%.

In other embodiments, the MAIT cells disclosed herein express interleukin (IL)-18Rα, CD127, α4β7, and/or PD-1. In some embodiments, the MAIT cells express interleukin (IL)-18Rα, CD127, and α4β7. In some embodiments, the MAIT cells express interleukin PD-1. In some embodiments, the MAIT cells express interleukin (IL)-18Rα, CD127, α4β7, and PD-1. In some embodiments, the cells also express the transcription factors promyelocytic leukemia zinc finger (PLZF), RORγt, Helios, Eomesodermin (Eomes), and/or T-box transcription factor (T-bet). In some embodiments, the MAIT cells express the transcription factors promyelocytic leukemia zinc finger (PLZF), RORγt, Helios, Eomesodermin. In some embodiments, the MAIT cells express T-box transcription factor. In some embodiments, the MAIT cells express the transcription factors promyelocytic leukemia zinc finger (PLZF), RORγt, Helios, Eomesodermin, and T-box transcription factor. Alternatively, or in addition, the cells express the surface markers CD26, CD44, CD69, or CD25; or the receptors interleukin 7 receptor (IL-7R), IL-12R, IL-15R, or IL-18R. In some embodiments, the cells express Inducible T-cell costimulator (ICOS). Each of the above proteins, and each combination thereof, represents a separate embodiment.

In some embodiments, the MAIT cells disclosed herein express genes related to tissue repair (e.g., Transforming Growth Factor Beta-1, Platelet Derived Growth Factor Subunit B, or Matrix Metallopeptidase) or angiogenesis (e.g., Granulocyte-Macrophage Colony-Stimulating Factor, Vascular Endothelial Growth Factor, or Hypoxia Inducible Factor 1 Subunit Alpha) upon stimulation with 5-OP-RU.

In certain embodiments, the placental MAIT cells recognize microbial-derived riboflavin precursor derivatives. In some embodiments, the engineered placental CAR-MAIT cells secrete inflammatory cytokines (e.g., interferon-gamma [IFN-g or IFN-γ], tumor necrosis factor alpha [TNF-a or TNF-a], interleukin 17, or colony stimulating factor 2 [CSF2/GM-CSF]) upon activation, e.g., by recognition of MR-1 ligands or, in other embodiments, in an MR1-independent manner. In other embodiments, IL-17A, TNF-a, CSF2 or MIP-1 are all secreted. In other embodiments, IL-26, oncostatin M (OSM), or heparin binding early growth factor (HBEGF) are upregulated upon stimulation with IL-12, IL-18, IL-15, or Tumor necrosis factor-like protein 1A (TL1A). Alternatively, or in addition, the engineered placental CAR-MAIT cells disclosed herein perform granzymeB dependent cytotoxicity of target cells upon activation. In other embodiments, IFN-γ, perforin, or granzyme B are all upregulated.

In certain embodiments, the methods described herein comprise expansion and/or enrichment of the engineered MAIT cells in-vitro and/or ex-vivo before administration to a subject. In various embodiments, expansion or enrichment is performed either before or after engineering the MAIT cell to express the exogenous antigen receptor. In other embodiments, activation or stimulation assays are performed to characterize or determine the quality of the engineered MAIT cells. Typically, however, activation requires stimulation of antigen receptors and coreceptors, in combination with cytokine treatment. Once cells are activated, they can, in some embodiments, be further expanded (without reverting to naïve status) using cytokines alone.

In some embodiments, MAIT cells are in-vitro and/or ex-vivo expanded for at least about 5 days, in other embodiments 5-10 days; in other embodiments at least 10 days; in other embodiments 10-15 days; in other embodiments at least 15 days; in other embodiments 15-20 days; and in some embodiments, at least 20 days.

Throughout this application, various embodiments may be presented in a range format. It should be understood that the description in range format is merely for convenience and brevity and should not be construed as an inflexible limitation on the scope of the engineered MAIT cells and uses thereof. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

Methods for stimulating MAIT cells are known in the art. In one non-limiting embodiment, Hela cells overexpressing the human MR1 protein (Hela-hMR1) are washed and incubated with *Escherichia coli*, Dh5a ATCC strain (typically at a multiplicity of infection of 10-100 bacteria per HeLa cell), in antibiotic-free DMEM, for 30 min at 37° C., washed, then incubated at 37° C. for 2 hours in complete medium with 100 μg/mL gentamicin and 10 μg/mL chloramphenicol. MAIT cells are added for an overnight co-culture, then cells are harvested and stained for FACS analysis.

Additional methods for expanding and/or enriching MAIT cells are known in the art. In a non-limiting embodiment, MAIT cells are incubated with 5 μg/mL CpG, 300 nM 5-(2-oxopropylideneamino)-6-D-ribitylaminouracil (5-OP-RU), and 50 ng/ml human IL-15. In certain embodiments, IL-15 is included to preferentially enhance the expansion of memory T cells.

In some embodiments, sorted or purified or enriched MAIT cells are activated in-vitro and/or ex-vivo by CD3/CD28 stimulation (e.g., using functionalized beads, available commercially under the trademark TransAct™) in the presence of autologous or allogeneic irradiated PBMCs and IL-2, IL-7, IL-12, IL-18, IL-21, IL-15, or analogues thereof, or combinations thereof. In other embodiments, CD3/CD28 beads (commercially available at clinical grade under the trademark ClinEx Vivo™ Dynabeads®) are used with IL-7 and IL-2. A non-limiting exemplary protocol includes incubation for 10-14 days with ClinEx Vivo™ Dynabeads® at a cell:bead ratio of 3:1 in X Vivo-15™ (BioWhittaker®, Walkersville, MD), 100 units/mL IL-2, and 10 ng/ml of IL-7. Once activated, MAIT cells can be further expanded in the presence of cytokines, in various embodiments either with or without the aforementioned ligands.

In other embodiments, MAIT cells are activated in-vitro and/or ex-vivo in the presence of MAIT cell activating ligands, such as 5-OP-RU, 5-amino-4-D-ribitylaminouracil dihydrochloride (5-ARU), 5-(2-oxoethylideneamino)-6-D-ribitylaminouracil (5-OE-RU), 5-amino-6-ribitylamino-2,4-(1H, 3H)-pyrimidinedione (5-A-RU), or other Riboflavin (vitamin B2)-derivatives. In certain embodiments, the ligand (s) are provided in combination with cytokines, e.g., the cytokines mentioned herein. As a non-limiting example, MAIT cells can be expanded in 100 nM 5-OP-RU and 100 IU/mL IL-2, e.g., for 6-17 days. In other embodiments, MAIT cells are expanded and/or activated in-vitro and/or ex-vivo in the presence of MAIT cells activating drug metabolites (e.g., diclofenac metabolites). Once activated, MAIT cells can be further expanded in the presence of cytokines, in various embodiments either with or without the aforementioned ligands.

In some embodiments, MAIT cells are expanded and/or activated in vitro in the presence of IL-12, IL-15, IL-18, and range of 10-1000 nM 5-OP-RU, or IL-12+IL-18 or IL-15+IL-18 as described in the art.

In some embodiments, the engineered MAIT cells disclosed herein produce IL-17 and upregulate the Th17 associated transcription factor RORC (RORγt) upon PMA and Ionomycin stimulation, but not upon after CD3+CD28 stimulation.

In some embodiments, the engineered MAIT cells disclosed herein produce IFN-γ and upregulate T-bet upon PMA/Ionomycin stimulation. In more specific embodiments, these cells are $CD8^+$.

In various embodiments, over 30%, over 40%, over 50%, over 60%, or over 70% of the population of engineered MAIT cells disclosed herein express CD69.

In other embodiments, under 30%, under 20%, or under 10% of the population of MAIT cells disclosed herein express PD-1. In other embodiments, over 10%, over 15%, or over 20% of the population of engineered MAIT cells express and CD25. In other embodiments, any combination of two of the above markers are expressed, whose percentages may be freely combined with one another. In some embodiments, over 50%, over 60%, over 70%, or over 80% of the MAIT cells are $PD\text{-}1^-/LAG\text{-}3^-$, which is indicative of cells not exhibiting T cell exhaustion. In other embodiments, CTLA-4, TIGIT, 2B4, BTLA, CD57, TIM-3, or KLRG-1 are used to detect T-cells exhibiting exhaustion.

In some embodiments, the MAIT cells disclosed herein express CCR2, CCR5, CCR6, CCR9, CXCR4, CXCR3, VLA-4, or CXCR6, or a combination of 2, 3, 4, 5, 6, 7 or all 8 of these receptors. Alternatively, or in addition, the MAIT cells express activating receptors, e.g., NKG2D, NKp30, NKp44 or NKG2D and NKp30 and NKp44. In some embodiments, the MAIT cells express high levels of CXCR4 and moderate levels of CCR9, but low or no expression of CXCR2. Alternatively, or in addition, the MAIT cells also express CXCR3. In some embodiments, the MAIT cells disclosed herein express one or more cytokine receptors such as IL-7R, IL-12R, IL-15R, IL-18R, and IL-21R, or any combination thereof.

Exogenous Antigen Receptor

The term "exogenous antigen receptor" as used herein, comprises an antigen receptor not naturally present on the MAIT cells. Examples of such receptor is a chimeric antigen receptor (CAR). The MAIT cells disclosed herein are engineered to express an exogenous CAR.

In certain embodiments, the exogenous antigen receptor is permanently integrated into the engineered IVB-derived MAIT cells. In other embodiments, the IVB-derived MAIT cells are engineered to transiently express the exogenous antigen receptor gene. The term "permanent" is used herein to denote insertion of exogenous DNA into the genome of the target cells (which may utilize various viral and non-viral technologies generally known in the art). The term "transient" is used to denote engineering the cells to temporarily express the exogenous antigen receptor gene, in some embodiments via mRNA insertion into the cells.

A skilled artisan would appreciate that the exogenous antigen receptor disclosed herein comprises in certain embodiments, antigen binding domains that result in the MAIT cells comprising the exogenous antigen receptors to bind target molecules, i.e., the antigen of interest. As used herein, the terms "antigen" and "target molecule" may be used interchangeably having all the same qualities and meanings.

Chimeric Antigen Receptor (CAR)

As it is generally known in the art, chimeric antigen receptor (CAR) is genetically engineered receptor comprising at least an extracellular antigen binding domain, a hinge domain, a transmembrane domain, a costimulatory domain, and a cytoplasmic signaling domain. This engineered receptor can be readily inserted into and expressed by immune cells, such as placental or IVB-derived MAIT cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell.

In some embodiments, in the engineered placental CAR-MAIT cell described herein, the CAR comprises an engineered immunoreceptor containing (a) an extracellular antigen-binding domain optionally connected to a hinge region; (b) a transmembrane region; and (c) an intracellular signaling domain (e.g., CD3zeta or CD3z). In some embodiments, the extracellular antigen-binding domain comprises a single-chain variable fragment (scFv). In some embodiments, the extracellular antigen-binding domain comprises an antigen binding antibody fragment. In some embodiments, the extracellular antigen-binding domain comprises a single-chain antibody.

In some embodiments, the transmembrane domain may be derived from any of CD4, CD8, or CD3ζ domains, or domains derived from costimulatory molecules, such as CD28.

In some embodiments, the extracellular antigen-binding domain comprises an antigen binding fragment of an antibody. In certain embodiments, a co-stimulatory domain (non-limiting examples of which are 4-1BB/CD137, OX40/CD134, and CD28) is also present and is, in some embodiments, inserted into the CD3zeta domain. In some embodiments, both CD28 and another co-stimulatory domain, e.g., 4-1BB or OX40, are inserted.

In some embodiments, the costimulatory domain of a CAR is designed to provide costimulatory signaling to an activating domain, which then activates at least one of the normal effector functions of the immune cell. Effector function of a T cell may include but are not limited to, cytolytic activity or helper activity including the secretion of cytokines.

In certain embodiments, suitable costimulatory domains include, but are not limited to the costimulatory domain of 4-1BB/CD137, CD2, DAP12, ICOS, GITR, FcRg, CD27, CD28, LFA-1, OX-40, or a combination thereof.

Intracellular signaling or activating domains may also, in some embodiments, be incorporated into a CAR. For example, CD3 is an element of the T cell receptor on native conventional T cells and has been shown to be an important intracellular activating element in CARs. In some embodiments, the CD3 is CD3-zeta or CD3-epsilon.

Target Antigens

In certain embodiments, an exogenous antigen receptor, for example a CAR as described herein, directs the engineered MAIT cells to recognize a tumor antigen, a microbial antigen, a pathogen, a viral antigen, a fungal antigen, a bacterial antigen, an antigen expressed on Treg cells, an antigen expressed on alloreactive lymphocytes, an antigen expressed on senescent cells, an antigen expressed on cells associated with a fibrotic disease or condition, or an antigen expressed on cells associated with an autoimmune disease or disorder.

In some embodiments, a CAR comprised as part of an engineered IVB MAIT cell, directs the engineered MAIT cells to recognize, activate, proliferate, and lyse target cells in response to the CAR driven recognition of an antigen, for example but not limited to tumor-associated antigens (TAA) or viral antigens. In some embodiments, a CAR comprised as part of an engineered placental or IVB MAIT cell, directs the engineered MAIT cells to recognize, activate, proliferate, and lyse target cells in response to an scFv-driven recognition of an antigens, for example but not limited to, a tumor-associated antigens (TAA) or viral antigens. As used herein, the terms "CAR-MAIT" and "CAR-MAIT cells" encompass IVB-derived MAIT cells that have been engineered to express an exogenous CAR, and may be used interchangeably, having all the same qualities and meaning.

As used herein, "viral antigens" comprise antigens expressed by viral proteins, including scenarios in which the antigens are currently expressed by either a viral or a cancer cell (e.g., in the case of an oncogenic protein). Accordingly, in some embodiments, the engineered MAIT cells recognizing a viral antigen are used to treat a viral infection; or, in other embodiments, to treat a malignancy expressing a viral antigen. It will be understood by those skilled in the art that recognition of such antigens is typically MHC-independent, in the case of CAR.

Non-limiting examples of viral antigens include the following: hexon or penton, for example, for treating an adenovirus; HPV E6; HPV E7; immediate early-1 (IE-1) or tegument phosphoprotein of 65 kilodalton (pp65), for example, for treating cytomegalovirus (CMV); EBV nuclear antigen 1 (EBNA1), BZLF1, or products of any of the EBV latent genes LMP1, LMP2, EBNA1, EBNA2, EBNA3A, EBNA3B, or EBNA3C, for example, for treating Epstein-Barr virus (EBV) or lymphoma; VP1 or large T, for example, for treating BK virus (BKV); U11, U14, or U90, for example, for treating human herpesvirus 6 (HHV-6); herpes simplex virus-1 (HSV-1) thymidine kinase (HSV-TK), for example, for treating HSV-1.

In certain embodiments, the CAR target comprises a tumor-associated antigen (TAA) or cancer antigen. The term "tumor-associated antigens" or "cancer antigen", as used herein, comprise tumor-specific antigens, whether originally sourced from a virus or the normal cellular genome. It will be understood by those skilled in the art that recognition of such antigens is typically MHC-independent, in the case of CAR.

Non-limiting examples of suitable cancer antigens include the following: alpha-fetoprotein; Desmoyokin/AHNAK$^{S2580F}$; BCMA (e.g., for Relapsed or Refractory Multiple Myeloma); CD7 (e.g., for treating T-cell leukemia or lymphoma); CD19/20/22 (e.g., for treating Non-Hodgkin lymphoma, acute lymphoblastic leukemia, B-cell leukemia, or B-cell lymphoma); CD30 (e.g., for treating lymphomas, such as Hodgkin lymphoma); CD33; CD38; CD70 (e.g., for treating leukemias, lymphomas or renal cell carcinomas); CD73; CD123 and CD133 (e.g., for treating AML); CS1 (e.g., for treating multiple myeloma); c-MET; DR5; Diasialoganglioside GD2 or IL13ra2 (e.g., for treating neuroblastoma); EGFR V III; Epstein-Barr virus; (e.g., for treating B-cell malignancies); ERBB2$^{H473Y}$ and ERBB2IP$^{E805G}$; HBV surface antigen; HER2 (e.g., for treating glioblastoma); Mesothelin (e.g., for treating Mesothelin-expressing solid tumors); minor H antigen (HA-1); NKG2DL (e.g., for treating solid tumors or colorectal cancer); prostate-specific membrane antigen (PSMA); TPBG (trophoblast glycoprotein) or 5T4 (e.g., for treating solid tumors such as colorectal, ovarian and gastric cancer, and childhood acute lymphoblastic leukemia (ALL)); TGFβRII frameshift antigen; VEGFR-2; Wilms tumor 1 (WT-1); GPC3; ROR1; RAC1-P29S; COL6A3; HA-2; Claudin-18.2; MUC16; GPRC5D; HERV-E; Muc1, Claudin 3, Claudin 4 and Claudin 6.

In certain embodiments, or in addition, the engineered MAIT cells disclosed herein are used to target an MR-1 expressing tumor cell.

In other embodiments, the CAR target is a microbial antigen. Examples of microbial antigens include, but are not limited to, viral antigens, bacterial antigens, fungal antigens, and protozoa antigens. In certain embodiments, the engineered MAIT cells disclosed herein are used to treat a disease or infection caused by the microbe expressing the antigen.

A skilled artisan would appreciate that microbes comprise bacteria, viruses, fungi, and parasites, wherein microorganisms that cause disease are called pathogens. In some embodiments, as used herein the term "microbial antigen" may encompass a pathogenic target, i.e., a pathogenic antigen.

In some embodiments, the exogenous CARs target a bacterial antigen, which is used, in some embodiments, to treat a bacterial infection. In certain embodiments, the targeted bacterium can be selected from *Nitrospira* spp., *Nitrosospira* spp., *Nitrobacter* spp., *Nitrosomonas* spp., *Clostridium* spp., *Bacillus* spp., methanogenic archaea, coliforms, *Salmonella* spp., *Bacteroides* spp., *Staphylococcus* spp., *Streptococcus* spp., *Neisseria* spp., *Haemophilus* spp., *Bordetella* spp., *Listeria* spp., *Mycobacterium* spp., *Shigella* spp., *Pseudomonas* spp., *Brucella* spp., *Treponema* spp., *Mycoplasma* spp., *Yersinia* spp., *Vibrionaceae* spp., *Chlamydia* spp., *Legionella* spp., *Escherichia* spp., *Acinetobacter* spp., *Burkholderia* spp., *Thiobacillus* spp., *Rickettsia* spp., *Sphinomonas* spp., *Francisella* spp., *Campylobacter* spp., and *Helicobacter* spp.

In some embodiments, the exogenous CARs target a fungal antigen, which is used, in some embodiments, to treat a fungal infection. In one embodiment, the fungal infection is a yeast infection.

In some embodiments, the exogenous CARs target molecules expressed on regulatory T cells (Treg), and such targeting may result in depletion of the Treg. Treg-associated molecules are generally known in the art, for example, CCR8.

In some embodiments, the exogenous CARs target molecules expressed on alloreactive T cells. Such targeting would result in selective elimination of alloreactive T cells without depletion of other, non-alloreactive T cells. Depletion of alloreactive T cells is supposed to improve durability of response following patient treatment by allogeneic product. Alloreactive T cell targets include, but are not limited to, CD70.

In some embodiments, the exogenous CARs target molecules expressed in a subject suffering from a fibrotic disease, for example but not limited to cardiac fibrosis, wherein target antigens may encompass fibroblast activation protein (FAB).

In some embodiments, the exogenous CARs target molecules expressed in a subject suffering a senescence-associated disease or condition. Senescence is a chronic "alarm state" in tissues. The scope of such ailments is vast and includes such debilitating conditions as chronic inflammation, fibrotic liver disease, atherosclerosis, and diabetes. Examples of a molecule expressed by senescent cells include but are not limited to urokinase plasminogen activator receptor (uPAR), which can be targeted for by uPAR-specific CAR. Senescence targeting CAR T cells are called "senolytic CAR T". Disclosed herein are "senolytic CAR-MAIT" cells comprising exogenous antigen receptors targeting molecules expressed on the cell surface of senescent cells. In one embodiment, the target of an engineered MAIT cell disclosed here in is uPAR.

In some embodiments, the exogenous CARs target molecules disclosed herein, expressed in a subject suffering having an allogeneic transplantation, target antigen molecules expressed on alloreactive lymphocytes, for example but not limited to CD70.

In some embodiments, the exogenous CARs target molecules disclosed herein, expressed in a subject suffering from an autoimmune disease or disorder, target antigen molecules associated with those diseases of disorders. Example of autoimmune diseases include but are not limited to systemic lupus erythematosus (SLE) including refractory SLE, pemphigus vulgaris, multiple sclerosis, type I diabetes, rheumatoid arthritis, celiac disease, pernicious anemia, inflammatory myopathies, myasthenia gravis, or adrenalitis, or a combination thereof. In some embodiments, exogenous antigen receptors associated with autoimmune diseases or disorders comprise peptide-MHCII chimeric antigen receptor (pMHCII-CAR) with targets pathogenic MHC class II: peptide complex relevant to the autoimmune disorder, chimeric autoantibody receptor (CAAR) such as DSG3-specific CAAR, CD19- and/or CD20-specific CAR, B cell antibody receptors (BARs). In other embodiments, exogenous antigen receptors associated with autoimmune diseases and disorders comprise carboxypeptidase H, chromogranin A, glutamate decarboxylase, Imogen-38, insulin, insulinoma antigen-2 and 2β, islet-specific glucose-6-phosphatase catalytic subunit related protein (IGRP), proinsulin, citrullinated protein, collagen II, heat shock proteins, human cartilage glycoprotein, double-stranded DNA, La antigen, nucleosomal histones, ribonucleoproteins (snRNP), phospholipid-β-2 glycoprotein I complex poly (ADP-ribose) polymerase, Sm antigens of U-1 small ribonucleoprotein complex, a enolase, aquaporin-4, β-arrestin, myelin basic protein, myelin oligodendrocytic glycoprotein, proteolipid protein S100-β; R1-type reticulin, gastric H+/K+-ATPase, 21-hydroxylase, 17-hydroxylase, and the cytochrome P450 side-chain cleavage enzyme, or CD19.

Methods of Uses

Described herein are methods of use of MAIT and engineered MAIT cells described throughout. In some embodiments, the engineered MAIT cells used in the methods disclosed herein comprise engineered placental MAIT cells. In some embodiments, the engineered MAIT cells used in the methods described herein comprise engineered IVB MAIT cells. In some embodiments, the source of the engineered placenta-derived MAIT cells used in the methods disclosed herein is maternal. In some embodiments, the source of the engineered placenta-derived MAIT cells used in the methods disclosed herein is placenta blood from the decidua basalis region. In some embodiments, the source of the engineered placenta-derived MAIT cells used in the methods disclosed herein is placenta blood from the decidua parietalis region. In some embodiments, the source of the engineered placenta-derived MAIT cells used in the methods disclosed herein is placental intervillous blood. In some embodiments, the source of placental MAIT comprises a combination of placental sources described herein. In some embodiments, the source of the placental MAIT used in methods disclosed herein is not cord blood.

In some embodiments, the MAIT cells used in the methods disclosed herein comprise placental MAIT cells. In some embodiments, the MAIT cells used in the methods described herein, comprise IVB MAIT cells. In some embodiments, the source of the placenta-derived MAIT cells used in the methods disclosed herein is maternal. In some embodiments, the source of the placenta-derived MAIT cells used in the methods disclosed herein is placenta blood from the decidua basalis region. In some embodiments, the source of the placenta-derived MAIT cells used in the methods disclosed herein is placenta blood from the decidua parietalis region. In some embodiments, the source of the placenta-derived MAIT cells used in the methods disclosed herein is placental intervillous blood. In some embodiments, the source of placental MAIT comprises a combination of placental sources described herein. In some embodiments, the source of the placental MAIT used in methods disclosed herein is not cord blood.

In some embodiments, the MAIT cells used in the methods disclosed herein are derived from a maternal blood source, a placental source, or a IVB source, or a combination thereof, wherein the MAIT cells may be engineered to express an exogenous antigen receptor or may not be engineered to express an exogenous antigen receptor. In some embodiments, MAIT cells are derived from a maternal blood source, a placental source, or a IVB source, or a combination thereof; and are not derived from cord blood wherein the MAIT cells may be engineered to express an exogenous antigen receptor or may not be engineered to express an exogenous antigen receptor.

In some embodiments of the methods of use described herein, the engineered MAIT cell comprises a CAR-MAIT cell, wherein the MAIT cell is derived from IVB. In some embodiments of the therapeutic methods described herein, a method comprises administering a population of CAR-MAIT cells to a subject in need.

In some embodiments, there is a provided a method of treating a subject having a tumor or malignancy, comprising the step of administering to the subject a population of engineered MAIT cells described herein.

In other embodiments, there is a provided a composition or a pharmaceutical composition comprising a population of engineered MAIT cells described herein for treating a subject having a tumor or malignancy. Those skilled in the art will appreciate, in light of the present disclosure, that tumors, malignancies, and hyperproliferative disorders can be treated with a population of engineered MAIT cells disclosed herein, particularly in cases where cells of the tumor, malignancy, or hyperproliferative disorders comprise (e.g., express, or in other embodiments contain) the recognized antigen. In some embodiments of methods of treating a subject having a tumor or malignancy, the engineered MAIT cells are derived from placental intervillous blood. In some embodiments, when treating a subject having a tumor or malignancy, the engineered MAIT cells are allogeneic to the subject. In some embodiments, when treating a subject having a tumor or malignancy, the engineered MAIT cells comprise an engineered CAR directed to a cancer antigen or tumor associated antigen, for example but not limited to those disclosed herein.

In other embodiments, there is a provided a method of eliminating alloreactive T cells in a subject in need thereof, comprising the step of administering to the subject a population of engineered MAIT cells described herein. In some embodiments, a subject in need of eliminating alloreactive T cells comprises a subject having an allogeneic transplantation. In some embodiments, the engineered MAIT cells are targeted to alloreactive T cells due to expression of the exogenous CARs targeting molecules expressed on alloreactive T cells. In some embodiments, the subject may have a condition related to transplantations such as bone marrow transplantation, solid organ transplantation, or any other allogeneic transplantations. In some embodiments of methods of eliminating alloreactive T cells in a subject, the engineered MAIT cells are derived from placental intervillous blood. In some embodiments, the engineered MAIT cells are allogeneic to the subject. In some embodiments, the engineered MAIT cells target expressed on alloreactive lymphocytes. In some embodiments, the target expressed on alloreactive lymphocytes is CD70.

In other embodiments, there is a provided a method of eliminating regulatory T cells (T regs) as a method of treating cancer or improving anticancer treatment(s) in a subject, comprising the step of administering to the subject a population of engineered MAIT cells described herein. In some embodiments, the engineered MAIT cells are targeted to T regs due to expression of the exogenous CARs targeting molecules expressed on the T regs. In some embodiments, the targeting molecule expressed on Tregs is CCR8.

In some embodiments, there is provided a method of treating a subject infected with a pathogen, comprising the step of administering to the subject a population of engineered MAIT cells described herein. In other embodiments, there is provided a composition or a pharmaceutical composition comprising a population of engineered MAIT cells described herein for treating a subject infected with a pathogen. The pathogen can be a bacterial pathogen, a viral pathogen, or a fungal pathogen generally known in the art. Those skilled in the art will appreciate, in light of the present disclosure, that various infections can be treated with the engineered MAIT cells disclosed herein, particularly in cases where the pathogenic cells comprise (e.g., express, or in other embodiments contain) the recognized antigen. In some embodiments of methods of treating a subject infected with a pathogen, the engineered MAIT cells are derived from placental intervillous blood. In some embodiments, when treating a subject infected with a pathogen with engineered MAIT cells described herein, the engineered MAIT cells are allogeneic to the subject.

In some embodiments, there is provided a method of treating a subject suffering from a fibrotic disease, comprising the step of administering to the subject a population of engineered MAIT cells described herein. In other embodiments, there is provided a composition or a pharmaceutical composition comprising a population of engineered MAIT cells described herein for treating a subject suffering from a fibrotic disease. The fibrotic disease may be any fibrotic disease generally known in the art, for example but not limited to cardiac fibrosis. In some embodiments of methods of treating a fibrotic disease, the engineered MAIT cells target an expressed antigen associated with a fibrotic disease. In some embodiments of methods of treating a fibrotic disease, the engineered MAIT cells target fibroblast activation protein (FAP). In some embodiments of methods of treating a subject suffering from a fibrotic disease, the engineered MAIT cells are derived from placental intervillous blood. In some embodiments, when treating a subject suffering from a fibrotic disease with engineered MAIT cells described herein, the engineered MAIT cells are allogeneic to the subject.

In some embodiments, there is provided a method of treating a subject suffering from a senescence-associated disease or condition, comprising the step of administering to the subject a population of engineered MAIT cells described herein. In other embodiments, there is provided a composition or a pharmaceutical composition comprising a population of engineered MAIT cells described herein for treating a subject suffering from a senescence-associated disease or condition. The senescence-associated disease or condition may be any senescence-associated disease or condition generally known in the art, for example but not limited to chronic inflammation, fibrotic liver disease, atherosclerosis, or diabetes, or a combination thereof. In some embodiments of methods of treating a senescence-associated disease or condition, the engineered MAIT cells target an expressed antigen associated with a senescence-associated disease or condition. In some embodiments of methods of treating a senescence-associated disease or condition, the engineered MAIT cells target urokinase plasminogen activator receptor (uPAR). In some embodiments of methods of treating a subject suffering from a senescence-associated disease or condition, the engineered MAIT cells are derived from placental intervillous blood. In some embodiments, when treating a subject suffering from a senescence-associated disease or condition with engineered MAIT cells described herein, the engineered MAIT cells are allogeneic to the subject.

In some embodiments, there is provided a method of treating a subject suffering from an autoimmune disease or disorder, comprising the step of administering to the subject a population of engineered MAIT cells described herein. In other embodiments, there is provided a composition or a pharmaceutical composition comprising a population of engineered MAIT cells described herein for treating a subject suffering from an autoimmune disease or disorder. The autoimmune disease or disorder may be any autoimmune disease or disorder generally known in the art, for example but not limited to systemic lupus erythematosus (SLE), refractory SLE, pemphigus vulgaris, multiple sclerosis, type I diabetes, rheumatoid arthritis, celiac disease, pernicious anemia, inflammatory myopathies, myasthenia gravis, or adrenalitis, or a combination thereof. In some embodiments of methods of treating an autoimmune disease or disorder, the engineered MAIT cells target an expressed antigen associated with an autoimmune disease or disorder. In some embodiments of methods of treating an autoimmune disease or disorder, the engineered MAIT cells target a pathogenic MHC class II: peptide complex associated with said autoimmune disease, an autoantibody, a B cell antibody targeted by B cell antibody receptors (BAR), carboxypeptidase H, chromogranin A, glutamate decarboxylase, imogen-38, insulin, insulinoma antigen-2 and 2B, islet-specific glucose-6-phosphatase catalytic subunit related protein (IGRP), pro-insulin, citrullinated protein, collagen II, heat shock proteins, human cartilage glycoprotein, double-stranded DNA, La antigen, nucleosomal histones and ribonucleoproteins (snRNP), phospholipid-β-2 glycoprotein I complex poly (ADP-ribose) polymerase, Sm antigens of U-1 small ribonucleoprotein complex, a enolase, aquaporin-4, β-arrestin, myelin basic protein, myelin oligodendrocytic glycoprotein, proteolipid protein S100-β, R1-type reticulin, gastric H+/K+-ATPase, 21-hydroxylase, 17-hydroxylase, cytochrome P450 side-chain cleavage enzyme, CD19, wherein said engineered MAIT cells bind said pathogenic MHC class II: peptide complex associated with said autoimmune disease, an autoantibody, a B cell antibody targeted by B cell antibody receptors (BAR), carboxypeptidase H, chromogranin A, glutamate decarboxylase, imogen-38, insulin, insulinoma antigen-2, 2β, islet-specific glucose-6-phosphatase catalytic subunit related protein (IGRP), pro-insulin, citrullinated protein, collagen II, heat shock proteins, human cartilage glycoprotein, double-stranded DNA, La antigen, nucleosomal histones, ribonucleoproteins (snRNP), phospholipid-β-2 glycoprotein I complex poly (ADP-ribose) polymerase, Sm antigens of U-1 small ribonucleoprotein complex, a enolase, aquaporin-4, β-arrestin, myelin basic protein, myelin oligodendrocytic glycoprotein, proteolipid protein S100-β, R1-type reticulin, gastric H+/K+-ATPase, 21-hydroxylase, 17-hydroxylase, cytochrome P450 side-chain cleavage enzyme, or CD19. In some embodiments of methods of treating a subject suffering from an autoimmune disease or disorder, the engineered MAIT cells are derived from placental intervillous blood. In some embodiments, when treating a subject suffering from an autoimmune disease or disorder with engineered MAIT cells described herein, the engineered MAIT cells are allogeneic to the subject.

In some embodiments, method of treating a subject in need comprising use of any of the engineered MAIT cells described herein, comprise treating a subject having a tumor or malignancy, a subject infected with a pathogen, a subject suffering from a fibrotic disease or condition, a subject suffering from a disease or condition associate with senescence, a subject having an allogeneic transplant, or a subject suffering from an autoimmune disease or disorder.

In certain embodiments, methods of treating a subject in need comprise use of placental MAIT cells that have not been engineered to express an exogenous antigen receptor. In some embodiments, there is provided a method of treating a subject infected with a pathogen, comprising administering to said subject a composition comprising a population of MAIT cells derived from placenta, wherein said MAIT cells do not comprise an engineered MAIT cell expressing an exogenous antigen receptor. In other embodiments, there is provided a composition or a pharmaceutical composition comprising a population of MAIT cells described herein for treating a subject infected with a pathogen. In certain embodiments, methods of use treating a subject infected with a pathogen comprise treating an infectious condition that is limited to a specific site or organ. In some embodiments, an infection limited to specific sites and or organs comprises a post-surgical infection. In some embodiments, of methods treating a subject infected with a pathogen, the MAIT cells are allogeneic to said subject.

In some embodiments, the pathogen is a bacterial pathogen, a viral pathogen, or a fungal pathogen. In some embodiments, a bacterial pathogen comprises an antibiotic resistant bacteria or bacterial treatment resistant bacteria. In some embodiments, said bacterial pathogen comprises a *Mycobacterium tuberculosis* bacteria. In some embodiments, a fungal pathogen comprises an invasive *Aspergillus*. In some embodiments, a viral pathogen comprises a cytomegalovirus, a hepatitis B virus, or a hepatitis C virus. In some embodiments of methods of treating a subject infected with a pathogen, the MAIT cells are derived from placental intervillous blood. In some embodiments, when treating a subject infected with a pathogen with MAIT cells described herein, the MAIT cells are allogeneic to the subject.

Pharmaceutical Compositions

In some embodiments, a composition comprises an engineered MAIT cell expressing an exogenous antigen receptor. In some embodiments, a composition comprises an MAIT cell not expressing an exogenous antigen receptor. As used herein, the terms "composition", "cell composition", and "pharmaceutical composition" may in some embodiments be used interchangeably having all the same qualities and meanings. In some embodiments, disclosed herein is a pharmaceutical composition for the treatment of a condition or disease as described herein.

In some embodiments, disclosed herein is a pharmaceutical composition comprising a pharmaceutically acceptable carrier and a population of engineered MAIT cells described herein. In some embodiments, disclosed herein is a pharmaceutical composition comprising a pharmaceutically acceptable carrier and a population of MAIT cells described herein, that have not been engineered to express an exogenous antigen receptor.

A skilled artisan would appreciate that a "pharmaceutical composition" may encompass a preparation of one or more of the active ingredients described herein with other chemical components such as physiologically suitable carriers and excipients. The purpose of a pharmaceutical composition is to facilitate administration of a compound to an organism.

A skilled artisan would appreciate that the phrases "physiologically acceptable carrier", "pharmaceutically acceptable carrier", "physiologically acceptable excipient", and "pharmaceutically acceptable excipient", may be used interchangeably may encompass a carrier, excipient, or a diluent that does not cause significant irritation to an organism and does not abrogate the biological activity and properties of the administered active ingredient.

Techniques for formulation and administration of drugs or pharmaceutical compositions are found in "Remington's Pharmaceutical Sciences," Mack Publishing Co., Easton, PA, latest edition, which is incorporated herein by reference.

In some embodiments, the composition or pharmaceutical composition disclosed herein is an injectable composition that is manufactured by adding one or more excipients, e.g., stabilizers and aqueous buffers, to the population of engineered MAIT cells described herein. In some embodiments, the composition or pharmaceutical composition disclosed herein is an injectable composition that is manufactured by adding one or more excipients, e.g., stabilizers and aqueous buffers, to the population of MAIT cells that have not been engineered to express an exogenous antigen receptor.

Alternatively or in addition, the engineered MAIT cells described herein have been expanded at least 100 fold, in other embodiments at least 200 fold, in other embodiments at least 400 fold, in other embodiments at least 600 fold, in other embodiments at least 1000 fold, in other embodiments at least 1500 fold, in other embodiments at least 2000 fold, in other embodiments at least 3000 fold, and still in other embodiments at least 5000 fold compared to day 0 of expansion, before administration to a patient.

In some embodiments, the method of preparing the pharmaceutical composition comprising the engineered MAIT cells described herein includes steps for freezing, e.g., cryopreserving, the cells, either before or after isolation, incubation, and/or engineering. Examples of suitable freezing agents are generally known in the art.

In other embodiments, for injection, the engineered MAIT cells disclosed herein may be formulated in aqueous solutions, preferably in physiologically compatible buffers such as Hank's solution, Ringer's solution, or physiological salt buffer, optionally in combination with medium containing cryopreservation agents.

In other embodiments, there is provided a pharmaceutical composition, comprising the engineered MAIT cells disclosed herein, wherein the composition is indicated for treating or ameliorating any of the diseases, disorders, and complications mentioned herein, each of which represents a separate embodiment.

One may, in various embodiments, administer the pharmaceutical composition disclosed herein in a systemic manner as generally known in the art. Alternatively, one may administer the pharmaceutical composition locally, for example, via injection of the pharmaceutical composition directly into a tissue region of a patient, such as, in non-limiting embodiments, an atrophied muscle. In other embodiments, the engineered MAIT cells are administered intramuscularly, intravenously, subcutaneously, or intraperitoneally, each of which is considered a separate embodiment. In this regard, "intramuscular" administration comprises administration into the muscle tissue of a subject; "subcutaneous" to administration just below the skin; and "intravenous" comprises administration into a vein of a subject. In some embodiments, the pharmaceutical composition is administered intralymphatically as previously described in the art.

Effective dosages and schedules for administering the compositions may be determined empirically, and making such determinations is within the skill in the art. The dosage can be adjusted by the individual physician in the event of any counterindications.

Depending on the severity and responsiveness of the condition to be treated, dosing can be of a single or, in other embodiments, a plurality of administrations, until alleviation of the disease state is achieved.

In certain embodiments, the treatment methods described herein further includes lymphodepleting, or in other embodiments immunosuppressing, the recipient prior to treatment. In other embodiments, reversible lymphodepletion or immunosuppression extends the biological half-life of the transplanted cells. Methods for lymphodepletion and immunosuppression of patients are known in the art. In some embodiments, lymphodepletion or immunosuppression is not necessary for administration of the engineered MAIT cells disclosed herein, at least in part because of their low immunogenicity.

In various embodiments, engraftment of the engineered MAIT cells in the host is not required for the cells to exert the described therapeutic effects, each of which is considered a separate embodiment. In other embodiments, engraftment is required for the engineered MAIT cells to exert the effect(s).

In certain embodiments, the subject treated by the methods and compositions described herein has a tumor. In other embodiments, the subject has a bacterial infection. In some embodiments, the subject has a viral infection. In some embodiments, the subject has a fungal infection. In some embodiments, the subject is a human.

Also disclosed herein are kits and articles of manufacture that are drawn to reagents that can be used in practicing the methods disclosed herein. The kits and articles of manufacture can include any reagent or combination of reagent discussed herein or that would be understood to be required or beneficial in the practice of the disclosed methods, including lymphoid cells. In another aspect, the kits and articles of manufacture comprise a label, instructions, and packaging material, for example for treating a disorder or therapeutic indication mentioned herein.

It is appreciated that certain features of the engineered MAIT cells and methods of use thereof, which are, for clarity, described in the context of separate embodiments, may also be provided in combination in a single embodiment. Conversely, various features of the engineered MAIT cells and methods of use thereof, which are, for brevity, described in the context of a single embodiment, may also be provided separately or in any suitable sub-combination or as suitable in any other described embodiment of the engineered MAIT cells and methods of use thereof.

Additional Materials and Methods

IVB Collection

Placenta donors were recruited after C-sections at various medical centers in Israel, with written informed consent obtained from the maternity patients. The umbilical cord was clamped with two clips to prevent the mixing of fetal and maternal blood. The placenta was placed on a large plate with the fetal side down and the amnion membrane was removed to expose the cotyledons. Small X-shaped incisions were made only in the upper part of the cotyledons made by surgical scissors. The placenta was then flipped with the fetal side facing up, and PBS was injected into the decidua basalis at different points away from the fetal blood vessels. All the maternal intravenous blood (IVB) flowing out of the placenta was collected. Mononuclear cells were then isolated using Lymphoprep (a density gradient column), and an intermediate cell stock was subsequently frozen.

RNAseq and Legend Screen

Blood and Intervillous blood (IVB) donors: PBMCs were obtained from healthy donors recruited at the Blood Transfusion lab at the Sheba Medical Center, Tel-Hashomer, Israel. IVB samples were harvested from human term placentas that were collected from healthy individuals giving birth through planned elective caesarean sections following healthy pregnancies (from the Bnai Zion Medical Center, Haifa, Israel). Written informed consent was obtained from the patients.

MAIT Cells and PBMCs Processing

PBMCs and IVB Human mononuclear cells (MNCs) were isolated by Lymphoprep density gradient centrifugation. Cells were frozen in 90% FBS+10% DMSO.

MAIT Cells Processing for RNAseq

Cryopreserved PBMCs/IVB MNCs were thawed and cultured at a concentration of $2\times10^6$/ml in 24 well plate with full OpTmizer CTS medium (Gibco) supplemented with Optimizer CTS T cell expansion supplement (Gibco), 2.5% CTS Immune cell SR (Gibco), 2 mM Glutamax 100× (Gibco), 100 U/mL Pen/Strep 100× (Gibco), IL-15 (50 ng/ml, Peprotech) and 250 nM 5-OP-RU [prepared by mixing of 5-A-RU (Cayman chemical) and Methylglyoxal (Merck)]. Every 2-3 days the medium was replenished by re-culturing the expanded cells at concentration of 0.5-1×$10^6$/ml with fresh medium containing 50 ng/ml IL-15. On day 7 expanded cells were MACS-sorted via biotin-conjugated anti-TCR Vα7.2 REAfinity antibody (Miltenyi biotech) and anti-Biotin MicroBead (Miltenyi biotech) labeling to enrich MAIT cells.

PBMCs Processing

PBMCs were obtained from healthy donors recruited at the Blood Transfusion lab at the Sheba Medical Center, Tel-Hashomer, Israel. Written informed consent was obtained from the patients. PBMCs were isolated by Lymphoprep density gradient centrifugation, cryopreserved in CryoStor CS10 (BioLife Solutions) and stored in liquid nitrogen vapor phase.

CAR-T Preparation

Thawed PBMCs were cultured overnight at a density of 1×$10^6$/ml in OpTmizer CTS medium (Gibco) supplemented with Optimizer CTS T cell expansion supplement (Gibco), 2 mM Glutamax 100× (Gibco), 100 U/mL Pen/Strep 100× (Gibco), IL-2 IS premium grade (Miltenyi Biotech) and with TransAct anti-CD3/anti-CD28 polymeric nanomatrix (Miltenyi Biotech). Transduction was performed on the next day (Day 1) with LV MSLN-Flag CAR vector (VectorBuilder) at MOI of 1:10 for the transduced culture, or with no vector as a non-transduced control (NTD ctrl). No transduction enhancers (such as Retronectin or Polybrene) were used. On day 4, cells were transferred to 24 or 6 wells G-Rex culture (Wilson Wolf, MN, USA) containing 1% HI human AB serum (IMBH), IL-2 IS premium grade was added to the culture every other day. Culture was harvested on day 12-13. Samples were pulled on day 8 and 12-13 for cell fold expansion calculation and for MSLN-CAR expression testing by CytoFLEX V5-B5-R3 Flow Cytometer (Beckman) using Whitlow/218 Linker (E3U7Q) Rabbit mAb (Cell signaling technology).

CAR-MAIT Preparation

Frozen White blood cells from IVB source were thaw and cultured overnight in OpTmizer CTS medium (Gibco) full media containing Fetal Bovine Serum (FBS) and IL-15. On the following day, the cells were activated using 5-OP-RU (a known activator of MAIT cells) for 48 hours. On day 3, cells were counted and OpTmizer CTS medium was refreshed. On day 5, cells were collected and separated using LS column with antibodies against Vα7.2 and magnetic micro-beads (Miltenyi Biotech). Pure MAIT cells fraction (after separation) was incubated for three hours following by transduction with LV MSLN-Flag CAR vector (VectorBuilder) at MOI of 1:10. Transduction was performed on plates covered with Retronectin (Takara) that were spinoculated for 2 hours with the viruses and overnight incubation with pure MAIT cells. Removal of viruses was performed by 4 washes followed by pure MAIT cells counting and culture until day 10-12. Full OpTmizer medium enriched with IL-15 was added to the culture every other day.

Cell Surface Staining—Flow Cytometry

Cells were placed in a 96-well microplate and washed with a staining buffer containing FBS and EDTA. Cells were then stained with a cocktail of fluorescently labeled antibodies for CD3, TCR Vα7.2 and CD161 to detect MAIT cells and additional antibodies as indicated. Cells were incubated for 20 min at 4° C., washed and resuspended in the staining buffer containing 7-AAD viability dye. Stained cells were analyzed on CytoFlex flow cytometer; results were then analyzed on FlowJo or Kaluza software.

Intracellular Staining—Flow Cytometry

Cells were placed in a 96-well microplate in T cell medium supplemented with Phorbol 12-myristate 13-acetate (PMA) and ionomycin to induce T cell activation, and with brefeldin A and monensin (BD) to inhibit protein secretion. Cells were incubated at 37° C. for 4 hrs, then washed with staining buffer and stained with fixable viability dye followed by staining with cell surface antibodies as above. Cells then were fixed and permeabilized with the Cytofix/Cytoperm solution (BD) for 30 min at room temperature, washed with the Perm/Wash buffer (BD) and stained for 30 min at 4° C. in the Perm/Wash buffer containing fluorescently labeled antibodies for intracellular proteins (IFNγ, TNFα, perforin and Granzyme B). Cells were washed and analyzed as described above.

Luciferase Killing Assay

Luc-labeled target cells were seeded in 96-well plates (1.0E4 per well) and CAR-T or CAR-MAIT cells were added after 4 hours in duplicates. Following 18 hours incubation the luciferase activity was determined with the Bio-Glo Luciferase Assay system (Promega). Viability was normalized to the maximum RLU signal for a given effector. EC50 was estimated using GraphPad Prism (Sigmoidal (4PL)).

EXAMPLES

Example 1—Isolation, Enrichment and Expansion of MAIT Cells From Intervillous Blood (IVB)

Placenta (100) is an organ that is composed of a fetal side (101) that comprises umbilical cord connecting the fetus to the mother (102) and a maternal side (104) that is covered with amnion membrane (105). For isolation of MAIT cell from IVB, the umbilical cord is first clamped for example, by using a clip (103), to prevent mixing of fetal blood with mother (IVB) blood. IVB collection begins with the removal of the amnion membrane surrounding the maternal side, exposing cotyledons (106). Superficial cuts are made in the cotyledons using scissors or any other suitable cutting tool. The placenta is then flipped such that the fetal side faces upward, and Phosphate buffer saline (PBS) is injected into the decidua basalis, away from the fetal blood vessels. All the maternal blood that flows out of the placenta is collected. Mononuclear cells are then isolated from the collected maternal blood using Lymphoprep (a density gradient column), and an intermediate cell stock is subsequently frozen (FIGS. 1A-1D).

FIGS. 2A-2T presents flow cytometric plots of MAIT cell's activation and proliferation for 10 days in a packed bed bioreactor in accordance with embodiments of the invention. Intervillous blood (IVB)'s mononuclear cells were seeded into packed bed bioreactor containing ECM-coated Fibra-Cel® carriers which mimic the natural environment and facilitate the attachment of antigen presenting cells (APCs). MAIT cells activation was induced by 5-OP-RU (250 ng/ml) and IL-15 (50 ng/ml). The activation and proliferation of MAIT cells were assessed at several time points: days 0, 5, 7 and 0. MAIT cells population was detected by the expression of CD3, Vα7.2, and CD161 markers. The results presented an increase in the proportion of MAIT cells starting with 22.63% on day 0 and up to 96.26% on day 10. Furthermore, the expression of activation markers CD69 and CD25 was elevated from day 0 to day 7 and slightly decreased by day 10.

FIGS. 2U-2AN presents flow cytometric plots of MAIT cells growth following transition of the cells from a first bioreactor to a second bioreactor on day 10 and additional 7 days growth in the second bioreactor in accordance with embodiments of the invention. Cells that had reached maximal growth capacity by day 10 in the first bioreactor were harvested, and approximately 30% of these cells were then seeded into a second bioreactor, which was similar in design to the first one. The cells were grown for an additional 7 days. Flow cytometry results demonstrated that MAIT percentages were similar during most of the time but presented a decrease from >90% at day 14 to 82% at day 17. CD69 marker expression was upregulated from 30% to 87% on day 17 indicating that MAIT cells maintained their activation signal, while CD25 gradually reduced as expected, indicating that the MAIT cells have recently been activated, but have not reached their full proliferative and functional state, suggesting their ability to be reactivated and functional upon future target encounter. As can be seen from the results MAIT cells are generally more abundant among placental intervillous blood (IVB) mononuclear cells than among peripheral blood mononuclear cells (PBMC).

FIGS. 3A-3B shows the results of placental IVB MAIT cells activation and expansion in accordance with some optional examples of the invention. To obtain a population enriched with MAIT cells, IVB derived mononuclear cells were seeded in tissue culture plates and MAIT cells activation was induced by 5-OP-RU (250 ng/ml) and in the presence of IL-15 (50 ng/ml). On days 3 and 5 post-activation, cells were counted and analyzed by flow cytometry for MAIT percentage, and fresh medium and IL-15 was added. After 7 days in culture, MAIT cells represented between 78% to 93% of cells in the CD3+ population, depending on the donor. On day 7, cells were separated with magnetic beads and anti-TCR Vα7.2 antibody, to further enrich for MAIT population. Cells were cultured for another 3 days (day 10) in the presence of IL-15.

The results show that MAIT percentage increase and MAIT fold expansion (increase in MAIT absolute numbers relative to the starting numbers throughout the culture period.

FIGS. 4A-4B show MAIT cells percentage among placenta intervillous blood (IVB) mononuclear cells compared to Peripheral Blood Mononuclear Cells (PBMC) gated on CD3+ cells from 10 and 11 (respectively) unrelated donors. p=0.0159.

As shown, although MAIT % varies significantly between donors in both peripheral blood and placenta, on average, there are significantly more MAIT cells among the CD3+ cells in IVB vs peripheral blood.

Example 2—Immunophenotype of Placental IVB MAIT Cells Compared to Peripheral Blood MAIT Cells The phenotypes of MAIT cells from placental IVB and from peripheral blood were analyzed using CD45RA and CD62L markers. FIGS. 5A-5O show immunophenotype analysis of placental IVB MAIT cells compared to PB MAIT cells collected from 6 different donors and analyzed on day 0.

Cells were stained according to standard cell surface marker staining protocol and analyzed by flow cytometry. Cell surface markers for CD45RA and CD62L were used to characterize the cells. As shown. Placental IVB MAIT cells have a statistically significant more "effector" memory" and less "terminally differentiated" cells compared to PB-MAIT cells. Gating strategy for phenotyping is listed on the right panel. Statistical analysis was done using GP Prism, t-test comparison. *p<0.05, p<0.01, *p<0.001.

Notably, MAIT cells derived from IVB had a significantly higher proportion of effector memory cells than MAIT cells derived from peripheral blood. Accordingly, they had less terminally differentiated effector cells than peripheral blood derived-MAIT cells. Effector memory cells might be a preferable phenotype for engineered MAIT cells, since they are more long-lived than terminal effectors, while they have better effector function and capabilities of migrating to peripheral tissues as compared to naïve and central memory cells.

Example 3—Chemokine Receptor Expression Analysis in Placental IVB MAIT Compared to Peripheral Blood MAIT Cells Chemokine receptors mediate migration of engineered MAIT cells to peripheral tissues and to secondary lymphoid organs; they can also be important for infiltration of engineered-MAIT cells into the tumor. The expression of chemokine receptors on MAIT cells from IVB vs MAIT from peripheral blood was analyzed.

FIGS. 6A-6AA show Chemokine receptor analysis of placental IVB MAIT cells and PB MAIT cells in accordance with examples of the invention. To evaluate the chemokine receptor profile of MAIT population IVB MAIT cells and PB MAIT cells were collected from six (6) different donors each and analyzed on day zero (0) for chemokine receptor expression. Cell surface markers for CCR6, CCR5, CXCR4 and CXCR6 were used to characterize the cells. Cells were stained according to standard cell surface marker staining protocol and analyzed by flow cytometry. Statistical analysis was done using GP Prism, t-test comparison. *p<0.05,  p<0.01, * p<0.001.

As observed in FIGS. 6A-6K IVB MAIT cells have higher expression of CCR5 and CCR6 chemokine receptors compared to PB MAIT cells. In addition, FIGS. 6L-6AA show that IVB MAIT cells have statistically significantly lower levels of CXCR4 and comparable levels of CXCR6 compared to PB MAIT cells.

The results obtained further exemplify that the two MAIT cell populations derived from IVB and from PB are different, and that IVB MAIT cells contain more cells of "effector memory" phenotype and less "terminally differentiated effector" cells compared to PB MAIT cells.

Example 4—Granzyme B and Perforin Expression in Placental IVB MAIT Compared to Peripheral Blood MAIT Upon Thawing Perforin and granzyme B are molecules essential for cytotoxic function of effector lymphocytes such as MAIT cells. Perforin creates holes in the target cells, while granzyme B enters the target cells through these holes and induces apoptosis. In a comparative analysis, it was found that compared with peripheral blood MAIT cells, IVB MAIT cells express significantly higher levels of both molecules upon stimulation with PMA/ionomycin. FIG. 7A shows a representative sample for both cell types, while FIG. 7B shows MAIT cells from placenta IVB and from peripheral blood.

Cells from 6 donors each, were stimulated with PMA/Ionomycin for 4 hours and analyzed for intracellular expression of granzyme B and perforin. As shown, placental IVB MAIT cells have statistically significantly higher levels of Granzyme B compared to peripheral blood MAIT cells indicating an increased effector and lytic capacity of the placental IVB MAIT. Cells were gated on MAIT cells. p=0.0001.

Example 5—Intervillous Blood (IVB) MAIT Compared to Cord Blood (CB) MAIT

MAIT cells were collected from intervillous (IVB) and cord blood (CB) for frequency and immunophenotypic comparison between the two specimens by flow cytometry.

FIGS. 8A-8B present flow cytometric plots of MAIT cells percentage among placental IVB and matched (same donor) CB, and a table summarizing the results obtained in the flow cytometric plots (FIG. 8C).

Cells from 3 different donors were taken as previously described. IVB cells and CB cells were activated similarly. As shown, CB has very few MAIT cells on day 0 compared to IVB, and their percentage is decreasing over time on days 6/7. In more detail, IVB MAIT and matched CB MAIT cells were collected according to protocols as described in the material and methods above. The cells were stained on day 0 and on days 6/7 for CD161 and TCR Vα7.2 which represent MAIT positive gating strategy. Squared gates represent the percentage of MAIT cells. The table describes the actual cell counts. As observed, Intervillous blood (IVB) has much more MAIT cells compared to cord blood (CB).

FIG. 9 shows flow cytometric plots of placental IVB MAIT cells and CB MAIT cells expression of CD8αα+ in accordance with examples of the invention. Our results show that placental IVB MAIT cells express high frequency of CD8aa+ at a 3 times higher frequency (41.2%) compared to CB MAIT cells (14.2%), indicating on a more "antigen experienced" phenotype compared to the immature/naïve state present in the CB MAIT cells.

CD8α is a cell surface glycoprotein that can be expressed either as a disulfide-linked heterodimer together with CD8β or as a homodimer. In contrast to CD8αβ, CD8αα is never expressed on naïve T cells but readily induced on strongly activated T cells receptor (TCR). In addition, CD8αα may act like other "tuning" molecules to aid survival, in a manner analogous to expression of KIRs or other NK cell associated receptors on T. MAIT cells from IVB and CB were stained for the two CD8 subunits, CD8α and CD8β and frequency was measured by flow cytometry. The results clearly indicate that IVB MAIT cells have higher frequency of CD8αα indicating on a more "antigen experienced" phenotype compared to naïve state presented in the CB MAIT cells.

FIGS. 10A-10B show flow cytometric plots of placental IVB MAIT cells and CB MAIT cells for effector memory phenotype using CD45RO, CD27, CD45RA, CCR7 and CD62L.

IVB MAIT and matched CB MAIT were collected according to methods described in the material and methods below. Cell surface markers for CD45RA, CD27, CCR7$^-$ CD62L and CD45RO were used to determine the cells immunophenotyping, where CD45RA−/CCR7−, CD45RA−/CD62L−, CD45RA−/CD45RO+ and CD27−/CD45RO− represent an effector memory cell, activated effector memory cells and effector memory phenotype respectively. As clearly shown in the flow cytometric plots, IVB MAIT cells defer from CB MAIT cells as IVB MAIT cells possess an effector memory phenotype whereas CB MAIT cells present a naïve phenotype.

In summary, comparing the percentages of MAIT cells in CB or IVB showed that the frequency of MAIT cells in CB is significantly lower than that in IVB. Furthermore, a lower frequency of CD8αα-expressing MAIT cells in CB indicates that the CB MAIT cells are in an immature state relative to the MAIT cells in IVB.

Example 6—Transcriptome Analysis of IVB MAIT Cells and PB MAIT Cells

Transcriptome analysis of IVB MAIT cells and PB MAIT cells showing a set of top 50 significantly expressed genes was made (FIG. 11, names of genes listed in the figure). In order to understand transcriptomic differences between MAIT cells derived from different tissues, i.e. PBMCs and IVB, cells were extracted and expanded as previously described, and an RNAseq analysis was performed. IVB and PB MAIT cells were collected from three (3) different donors each and analyzed on day seven (7) for RNAseq transcriptome analysis. Cells were harvested according to the description in methods. Heatmaps of significantly (|log 2FC|>1) and BH padj<0.01) differentially expressed protein coding genes between IVB and PB cell types. The clustering was performed applying the Pearson correlation calculation on the normalized values of the count data. The color scheme represents the z-scores.

As shown from the results, MAIT cells originating from IVB possess a unique and distinctive transcriptome landscape compared to peripheral blood MAIT cells, meaning that the two MAIT populations are highly distinctive from one another.

Example 7—Granzyme B and Perforin Expression in Placental IVB MAIT Cells Compared to Peripheral Blood MAIT Cells Following Expansion Granzyme B is a serine protease found in granules of lytic cells. It is secreted along with the pore forming protein Perforin to mediate apoptosis of target cells. Comparison between IVB MAIT cells and PB MAIT cells for Granzyme B secretion is illustrated in FIGS. 12A-12E.

Placental IVB MAIT cells and PB MAIT cells were collected from 4 donors each and expanded using a standard protocol as previously described in the Methods. On day 8 cells were activated with Phorbol Myristate Acetate (PMA) plus Ionomycin and analyzed for Granzyme B and Perforin secretion, using a standard intra-cellular staining protocol.

In order to evaluate the basal potential of MAIT cells originating from IVB or PB, the collected cells were stimulated with PMA and Ionomycin and stained for intracellular Granzyme B secretion.

As shown, stimulated IVB MAIT cells produce significantly higher levels of Granzyme B compared to PB MAIT cells indicating on an increased effector and lytic capacity of the cells originated from IVB. Statistical analysis was done using GP Prism, t-test comparison. *p<0.05, p<0.01, *p<0.001.

Example 8—Efficacy of Placental Derived CAR-MAIT Cells

Functional killing characteristics of placental IVB CAR-MAIT cells was analyzed and the results are illustrated in FIG. 13. For that purpose, CAR-MAIT cells were produced according to the standard protocol described in the Methods and co-cultured with NSCLC targets over expressing MSLN and Luciferase. Killing was measured by luminescence readout.

As shown in the graph, the different effectors have different levels of CAR$^+$ fraction. Co-culture with target cells was at a range of effector:target (E:T) ratio determined by the CAR$^+$ fraction. All different culture conditions of CAR- MAIT cells resulted in robust efficacy against the target cells, indicating on high and dose dependent efficacy of the placental CAR-MAIT cells.

Example 9—Comparison Between Intervillous Blood (IVB) MAIT Cells, Peripheral Blood (PB) T Cells and Cord Blood (CB) T Cells Derived from Matched Donors Comparison between IVB MAIT cells, peripheral blood (PB) mother T cells, and cord blood (CB) T cells from the same donor (matched blood) was made, to evaluate differences between MAIT cells and T cells and to eliminate donor to donor variability. The inventors evaluated functional differences of the different cells originating from the same donor. IVB, PBMCs, and CB were collected as described in the methods, and on day 0 were activated with T cell activators. Following intra cellular staining protocol, the cells were analyzed for Perforin, Granzyme B, IFN-γ and TNF-α using flow cytometry. FIGS. 14A-14B are a flow cytometric plot describing the raw data for Perforin and Granzyme B, while FIGS. 14C-14D are a flow cytometric plot describing the raw data for IFN-γ and TNF-α.

As shown in the results, IVB MAIT cells on day 0 possess completely different expression levels of effector molecules compared to conventional T cells, whereas T cells originating from Cord blood and Peripheral blood have similar expression levels of these effector molecules. Graphical summary of the results is illustrated in FIGS. 15A-15F which represent results from two donors. In this drawing percentage of cells from MAIT population from IVB, conventional T cell population from peripheral mother blood (MB) and CB (cultured using T cell standard activation protocol) are shown. The analysis was performed according to the gating strategy illustrated in FIGS. 14A-14D. The example is of two donors respectively, from each donor IVB, peripheral mother blood (MB) and cord blood (CB) were obtained. As shown in the results of two independent donors, IVB MAIT cells on day 0 possess increased percentage of Perforin$^+$, Granzyme B$^+$, Perforin$^+$+GranzymeB$^+$ (double positive), IFNg$^+$, TNFa$^+$, IFNg$^+$+TNFa$^+$ (double positive) compared to conventional T cells.

Example 10—Placental IVB MAIT and Placental IVB T Effector Function Analysis Day 0 matched IVB, PB and CB mononuclear cells from the same donor were thawed, activated and cultured with T cell activators according to standard protocol. Briefly, T cell expansion is used by activation of the TCR with CD28 and CD3 antibodies or beads (TransAct) with IL2 cytokine.

On day 10 cells were stained for CD161 and TCR Vα7.2 to evaluate the fraction of MAIT positive population. As observed, specific MAIT expansion protocol resulted in highly enriched >95% MAIT cells, whereas standard T cell expansion protocol resulted in negligible MAIT population <1.2%.

FIGS. 16A-16F are graphic illustrations describing comparison of IVB-MAIT and IVB-T effector function. IVB-MAIT were cultured as described in the methods. From the same raw material (IVB cell harvesting) the inventors also cultured T cells using standard conventional T cells protocol with TransAct and IL2. On day 10, IVB-MAIT cells and IVB-T cells were stimulated using PMA+Ionomycin or TransAct, stained for effector molecules e.g. IFN-g, TNF-a, Perforin and Granzyme B and analyzed by flow cytometry (FIGS. 16A-16E). Graphical summary of the results is illustrated in FIG. 16F that shows that MAIT cells have higher levels of Perforin and TNF-a compared to T cells originating from the same source namely placental IVB, indicating that placental IVB MAIT cells have higher effector functions compared to placental IVB T cells.

Example 11—Placental MAIT and Placental CAR-MAIT Immunophenotype

The immunophenotype of MAIT cells and CAR-MAIT cells from placenta was evaluated on day 10 using flow cytometry staining with CD45RA and CCR7 using standard cell surface marker protocol. As shown in FIGS. 17A-17B respectively. White blood cells were isolated from the placenta's intravenous blood and decidua basalis, activated with 5-OP-RU, and expanded until day 5. After separating the MAIT cells, they were transduced using lentivirus and expanded until day 10.

Both the MAIT cells and the engineered CAR-MAIT cells were expanded for 10 days, staining was performed and analyzed via flow cytometry was made. The gating strategy of CD45RA vs. CCR7 showed a statistically significant increase in "effector memory (EM)" compared to "central memory (CM)" cells. Naïve and terminally differentiated (TD) cells were nearly absent. The Results represent an average of 3 different donors analyzed on day 10 (FIG. 17C). Results showed that over 80% of both MAIT and CAR-MAIT cells were effector memory phenotype, while the rest of the cells were central memory phenotype. Naïve and terminally differentiated cells were less than 1%. CD62L staining showed either high or low expression. CD69 staining showed consistently increased expression following MAIT activation and throughout the expansion period.

Example 12—Anti-Bacterial Activity of Placental MAIT Cells-Inhibition of Bacterial Growth by Placental MAIT Secretions IVB-derived MAIT cells are obtained from placentas and co-cultured with MR-1-expressing cells (monocytes, macrophages, B cells, cell lines, etc.), loaded with MR-1 ligand (5-OP-RU, 5-OE-RU, etc.) or fixed bacteria, in antibiotic-free culture media. After 24-72 hours, the medium which contains the MAIT secretome is collected, and mixed with live antibiotic-resistance or antibiotic-sensitive bacteria (gram negative, such as carbapenem-resistant *Escherichia coli*, or KPC-producing *Klebsiella pneumoniae*, or gram positive, such as Methicillin-resistant *Staphylococcus aureus*, beta-lactam-resistant *Streptococcus pneumoniae*, or multi-drug-resistant *Mycobacterium tuberculosis*). After incubation of the bacteria with the collected medium for different time points (from several minutes to 24 hours), in the presence or absence of antibiotics, the bacteria are diluted and seeded on agar plates. Bacterial Colony Forming Unit (CFU) is counted after 24 hours from plating on agarose plates. The number of colonies is compared to the number of colonies grown after 24 hours following incubation of the bacteria with fresh antibiotic-free culture medium, in the presence or absence of antibiotics.

Example 13—Anti-Bacterial Activity of Placental MAIT-Killing of Cells Infected by Antibiotic Resistant Bacteria MR-1-expressing cells (monocytes, macrophages, B cells, HeLa cells, etc.) are infected with live bacteria (gram negative, such as carbapenem-resistant *Escherichia coli*, or KPC-producing *Klebsiella pneumoniae*, or gram positive, such as Methicillin-resistant *Staphylococcus aureus*, beta-lactam-resistant *Streptococcus pneumoniae*, or multi-drug-resistant *Mycobacterium tuberculosis*), in antibiotic-free culture media for 3 hours. The infected cells are washed and incubated with antibiotics for 1 hour to kill extracellular bacteria. IVB-derived MAIT cells are obtained from placentas, labeled with fluorescent dye (Cell Proliferation Dye eFluor™ 450, etc.) and added to the bacteria-infected cells in different effector to target ratios for 3 hours with addition of Caspase-3/7 Detection Reagent (CellEvent™ Caspase-3/7 Detection Reagents, etc.) for the last 30 minutes. Following incubation, the target cells are collected and analyzed by flow cytometry for activated caspase-3/7 and compared to the percentage of activated caspase-3/7 in bacteria-infected target cells alone. To assess the killing of intracellular bacteria, cell lysates of bacteria-infected target cells after co-culture with IVB-derived MAIT are diluted and seeded on agar plates. Bacterial CFU is counted after 24 hours from plating on agarose plates. The number of colonies is compared to the number of colonies grown after 24 hours following incubation of cell lysates of bacteria-infected target cells alone.

The invention claimed is:

1. A cell composition comprising a population of selected placental mucosal-associated invariant T (MAIT) cells engineered to express an exogenous chimeric antigen receptor (CAR), wherein said selected placental MAIT cells are derived from intervillous blood of placental tissue, and wherein said cell composition comprises at least $10^9$ viable engineered placental MAIT cells, wherein at least 90% of said viable engineered placental MAIT cells express TCRV$\alpha$7.2$^+$, and wherein at least 30% of said selected placental MAIT cells exhibit a CD45RA$^-$/CD62L$^-$ effector memory phenotype.

2. The cell composition of claim 1, wherein said at least $10^9$ viable engineered placental MAIT cells, of which at least 90% are TCRV$\alpha$7.2$^+$, further have CD161 expression in at least 70% of the cells.

3. The cell composition of claim 1, wherein said cell composition contains $10^9$-$10^{11}$ viable cells of said engineered placental MAIT cells.

4. The cell composition of claim 1, wherein said CAR expressed by said engineered placental MAIT cells recognize at least one tumor antigen.

5. The cell composition of claim 4, wherein said at least one tumor antigen is Mesothelin (MSLN).

6. The cell composition of claim 4, wherein said at least one tumor antigen is selected from the group consisting of CD19, B7-H6, CD20, CD22, CD33, CD38, CD70, CD123, BCMA, CLL1, CD7, CS1, CEA, AFP, PSMA, GPC3, GD2, EGFRVIII, CXCR5, NKG2D, HER2, Mesothelin, Claudin 3, Claudin 4, Claudin 6, Claudin 18.2, ROR1, ROR3, Muc1, or Muc16.

7. The cell composition of claim 1, wherein said CAR expressed by said engineered placental MAIT cells comprises:

an antigen-binding domain configured to specifically recognize a tumor-associated antigen;

a transmembrane domain that anchors said CAR in the cell;

at least one costimulatory domain that enhances cell signaling and T-cell activation; and an intracellular signaling domain responsible for initiating T-cell activation upon antigen recognition.

8. The cell composition of claim 7, wherein said antigen-binding domain of said CAR expressed by said engineered placental MAIT cells comprises a single-chain antibody, a single-chain variable fragment (scFv), a VHH fragment, or combinations thereof, wherein said single-chain antibody, said single-chain variable fragment (scFv), said VHH fragment, or said combinations thereof is configured to recognize at least one designated tumor-associated antigen.

9. The cell composition of claim 7, wherein said antigen binding domain of said CAR expressed by said engineered placental MAIT cells specifically binds to one or more antigens selected from the group consisting of: CD19, B7-H6, CD20, CD22, CD33, CD38, CD70, CD123, BCMA, CLL1, CD7, CS1, CEA, AFP, PSMA, GPC3, GD2, EGFRVIII, CXCR5, NKG2D, HER2, Mesothelin, Claudin 3, Claudin 4, Claudin 6, Claudin 18.2, ROR1, ROR3, Muc1, or Muc16.

10. The cell composition of claim 7, wherein said at least one costimulatory domain of said CAR expressed by said engineered placental MAIT cells comprises one or more functional signaling domain derived from OX40, CD2, CD27, CD28, CDS, ICAM-1, LFA-1 (CD11a/CD18), ICOS (CD278), or 4-1BB (CD137).

11. The cell composition of claim 7, wherein said intracellular signaling domain of said CAR expressed by said engineered placental MAIT cells comprises one of the intracellular signaling domain of CD3 zeta, FcR gamma, or a functional fragment thereof, each configured to initiate or maintain T-cell activation upon antigen recognition.

12. The cell composition of claim 1, wherein said CAR expressed by said engineered placental MAIT cells is encoded by a genetic construct selected from the group consisting of: a monocistronic construct, a bicistronic construct, or a tricistronic construct; wherein at least one additional element in the bicistronic or tricistronic construct is selected from the group consisting of cytokines, constitutively active tyrosine kinases, wherein said cytokines are either unmodified or modified, and/or secreted, conditionally active, constitutively active, or expressed in a membrane-bound form.

13. The cell composition of claim 1, wherein at least 30% of said selected placental MAIT cells co-express CCR5 and CCR6, and less than 50% of said selected placental MAIT cells express CXCR4.

14. The cell composition of claim 1, wherein at least 30% of said selected placental MAIT cells are capable of expressing Granzyme B following stimulation with PMA and Ionomycin.

15. The cell composition of claim 1, wherein at least 70% of said selected placental MAIT cells are capable of expressing Perforin following stimulation with PMA and Ionomycin.

16. The cell composition of claim 1, wherein at least 30% of said selected placental MAIT cells are capable of co-expressing Perforin and Granzyme B following stimulation with PMA and Ionomycin.

17. The cell composition of claim 1, wherein at least 70% of said selected placental MAIT cells are capable of expressing TNF$\alpha$ following stimulation with PMA and Ionomycin.

18. The cell composition of claim 1, wherein at least 70% of said selected placental MAIT cells are capable of co-expressing IFN$\gamma$ and TNF$\alpha$ following stimulation with PMA and Ionomycin.

19. The cell composition of claim 1, wherein at least 40% of said selected placental MAIT cells express CD8$\alpha$+ CD8$\beta$−.

20. A method of treating a cancer using an immunotherapeutic composition, the method comprising:

administering a therapeutic amount of the cell composition of claim 1 to a subject having a tumor or malignancy.

21. The method according to claim 20, wherein said tumor is selected from the group consisting of: blood cancer, melanoma, breast cancer, colon cancer, kidney cancer, liver cancer, lung cancer, ovary cancer, pancreatic cancer, prostate cancer, uterine cancer, cervical cancer, bladder cancer, stomach cancer, head and neck cancer, brain cancer, skin cancer and sarcoma.

22. The method according to claim 20, wherein said engineered placental MAIT cells are allogeneic to said subject.

23. The method according to claim 20, wherein said engineered placental MAIT cells are partly histocompatible with said subject, or not histocompatible with said subject.

24. A cell composition comprising a population of selected placental mucosal-associated invariant T (MAIT) cells engineered to express an exogenous chimeric antigen receptor (CAR), wherein said selected placental MAIT cells are derived from intervillous blood of placental tissue, and wherein said cell composition comprises at least $10^9$ viable engineered placental MAIT cells, wherein at least 90% of said viable engineered placental MAIT cells express TCRV$\alpha$7.2", and wherein at least 70% of said selected placental MAIT cells are capable of expressing TNF$\alpha$ following stimulation with PMA and Ionomycin.

* * * * *